(12) United States Patent
Popov et al.

(10) Patent No.: US 8,883,763 B2
(45) Date of Patent: Nov. 11, 2014

(54) USE OF ISOQUINOLONES FOR PREPARING DRUGS, NOVEL ISOQUINOLONES AND METHOD FOR SYNTHESISING SAME

(75) Inventors: Andrei Popov, Voreppe (FR); Aurélie Juhem, Grenoble (FR); Jean-Claude Florent, Gif sur Yvette (FR); Chi-Hung N'Guyen, Antony (FR)

(73) Assignees: Universite Joseph Fourier, Grenoble (FR); Centre National de la Recherche Scientifique, Paris (FR); Institut Curie, Paris (FR)

( * ) Notice: Subject to any disclaimer, the term of this patent is extended or adjusted under 35 U.S.C. 154(b) by 0 days.

(21) Appl. No.: 13/581,830

(22) PCT Filed: Mar. 1, 2011

(86) PCT No.: PCT/FR2011/050431
§ 371 (c)(1),
(2), (4) Date: Dec. 17, 2012

(87) PCT Pub. No.: WO2011/107709
PCT Pub. Date: Sep. 9, 2011

(65) Prior Publication Data
US 2013/0096083 A1   Apr. 18, 2013

(30) Foreign Application Priority Data
Mar. 1, 2010   (FR) ...................................... 10 00829

(51) Int. Cl.
| | | |
|---|---|---|
| *C07D 217/24* | (2006.01) | |
| *C07D 401/04* | (2006.01) | |
| *A61K 31/472* | (2006.01) | |
| *A61K 31/337* | (2006.01) | |
| *C07F 7/10* | (2006.01) | |
| *A61K 31/695* | (2006.01) | |
| *C07D 217/22* | (2006.01) | |
| *A61K 31/4709* | (2006.01) | |
| *C07D 215/233* | (2006.01) | |
| *A61K 31/4704* | (2006.01) | |
| *A61K 31/4725* | (2006.01) | |
| *A61K 31/5377* | (2006.01) | |
| *A61K 31/4375* | (2006.01) | |
| *C07D 413/04* | (2006.01) | |

(52) U.S. Cl.
CPC ............... *C07D 217/24* (2013.01); *C07F 7/10* (2013.01); *A61K 31/695* (2013.01); *C07D 401/04* (2013.01); *C07D 217/22* (2013.01); *A61K 31/4709* (2013.01); *C07D 215/233* (2013.01); *A61K 31/472* (2013.01); *A61K 31/4704* (2013.01); *A61K 31/4725* (2013.01); *A61K 31/5377* (2013.01); *A61K 31/4375* (2013.01); *A61K 31/337* (2013.01); *C07D 413/04* (2013.01)

USPC .......... 514/63; 514/235.2; 514/307; 514/309; 514/310; 544/128; 546/14; 546/141; 546/143; 546/144

(58) Field of Classification Search
None
See application file for complete search history.

(56) References Cited

FOREIGN PATENT DOCUMENTS

| | | |
|---|---|---|
| EP | 1724262 A1 | 11/2006 |
| EP | 1854792 A1 | 11/2007 |
| WO | 9203419 A1 | 3/1992 |
| WO | 2006-058201 A2 | 6/2006 |
| WO | 2008028427 A1 | 3/2008 |
| WO | 2008036540 A2 | 3/2008 |
| WO | 2008-063548 A2 | 5/2008 |

OTHER PUBLICATIONS

Alvarez e al, Science of Synthesis (2005), vol. 15, pp. 839-906.*
Jordan et al., "Microtubules as a Target for Anticancer Drugs", Nature Reviews, Cancer, 2004, vol. 4, pp. 253-265.
Jordan et al., "Mechanism of Inhibition of Cell Proliferation by Vinca Alkaloids", Cancer Research, 1991, vol. 51, pp. 2212-2222.
Derry et al., "Substoichiometric Binding of Taxol Suppresses Microtubule Dynamics", Biochemistry, 1995, vol. 34, pp. 2203-2211.
Li et al., "Antitumor Agents. 150. 2',3',4',5',5,6,7-Substituted 2-Phenyl-4-quinolones and Related Compounds: Their Synthesis, Cytotoxicity, and Inhibition of Tubulin Polymerization", Journal of Medicinal Chemistry, 1994, vol. 37, No. 8, pp. 1126-1135.
Li et al., "Antitumor Agents 155. Synthesis and Biological Evaluation of 3',6,7-Substituted 2-Phenyl-4-quinolones as Antimicrotubule Agents", Journal of Medicinal Chemistry, 1994, vol. 37, No. 20, pp. 3400-3407.
Chang et al., "Design and Synthesis of 2-(3-Benzo[b]thienyl)-6,7-methylenedioxyquinolin-4-one Analogues as Potent Antitumor Agents that Inhibit Tubulin Assembly", Journal of Medicinal Chemistry, 2009, vol. 52, pp. 4883-4891.
Le et al., "Phase I and pharmacokinetic study of fostriecin given as an intravenous bolus daily for five consecutive days", Investigational New Drugs, 2004, vol. 22, pp. 159-167.
Meijer et al., "Biochemical and cellular effects of roscovitine, a potent and selective inhibitor of the cyclin-dependent kinases cdc2, cdk2 and cdk5", Eur. J. Biochem. 1997, vol. 243, pp. 527-536.
Berndt et al., "Roles and regulation of serine/threonine-specific protein phosphatases in the cell cycle", Progress in Cell Cycle Research, 2003, vol. 5, pp. 497-510.
Alonso et al., "Protein Tyrosine Phosphatases in the Human Genome", Cell, 2004, vol. 117, pp. 699-711.

(Continued)

*Primary Examiner* — Zinna Northington Davis
(74) *Attorney, Agent, or Firm* — Young & Thompson

(57) ABSTRACT

The use of isoquinolones for preparing drugs, including novel isoquinolones as well as their synthesis method. In particular, isoquinolone derivatives used in the treatment of pathological angiogenesis, and more particularly of cancer.

34 Claims, 16 Drawing Sheets

(56) References Cited

OTHER PUBLICATIONS

Stewart et al., "Synthesis and biological evaluation of norcantharidin analogues: Towards PP1 selectivity", Biorganic & Medicinal Chemistry, 2007, vol. 15, pp. 7301-7310.
Andreassen et al., "Differential Subcellular Localization of Protein Phosphatase-1α, γ1, and δ Isoforms during Both Interphase and Mitosis in Mammalian Cells", The Journal of Cell Biology, 1998, vol. 141, no. 5, pp. 1207-1215.
Trinkle-Mulcahy et al., "Mitotic phosphatases: no longer silent partners", Current Opinion in Cell Biology, 2006, vol. 18, pp. 623-631.
Berndt et al., "Constitutively active protein phosphatase 1α causes Rb-dependent G1 arrest in human cancer cells", Current Biology, 1997, vol. 7, No. 6, pp. 375-386.
Margolis et al., "PP1 control of M phase entry exerted through 14-3-3-regulated Cdc25 dephosphorylation", The EMBO Journal, 2003, vol. 22, No. 21, pp. 5734-5745.
Goto et al., "Aurora-B phosphorylates Histone H3 at serine28 with regard to the mitotic chromosome condensation", Genes to Cells, 2002, vol. 7, pp. 11-17.
Meraldi et al., "Centrosome cohesion is regulated by a balance of kinase and phosphatase activities", Journal of Cell Science, 2001, vol. 114, No. 20, pp. 3749-3757.
Tang et al., "A Novel ATM-Dependent Pathway Regulates Protein Phosphatase 1 in Response to DNA Damage", Molecular and Cellular Biology, 2008, vol. 28, No. 8, pp. 2559-2566.
Emanuele et al., "Aurora B kinase and protein phosphatase 1 have opposing roles in modulating kinetochore assembly", The Journal of Cell Biology, 2008, vol. 181, No. 2, pp. 241-254.
Wu et al., "PP1-mediated dephosphorylation of phosphoproteins at mitotic exit is controlled by inhibitor-1 and PP1 phosphorylation", Nature Cell Biology, 2009, vol. 11, No. 5, pp. 644-651 and Supplementary Information pp. 1-4.
Thompson et al., "Identification of Protein Phosphatase 1 as a Mitotic Lamin Phosphatase", The Journal of Biological Chemistry, vol. 272, No. 47, 1997, pp. 29693-29697.
Ross et al., "Systematic variation in gene expression patterns in human cancer cell lines", Nature Genetics, 2000, vol. 24, 227-235.
Hsu et al., "Gene amplification and overexpression of protein phosphatase 1a in oral squamous cell carcinoma cell lines", Oncogene, 2006, vol. 25, pp. 5517-5526.
McConnell et al., "Targeting Protein Serine/Threonine Phosphatases for Drug Development", Molecular Pharmacology, 2009, vol. 75, pp. 1249-1261.
Kaur et al., "Growth Inhibition with Reversible Cell Cycle Arrest of Carcinoma Cells by Flavone L86-8275", Journal of the National Cancer Institute, vol. 84, No. 22, pp. 1736-1740, (1992).
Pinna et al., "Inhibitors of Protein Kinases and Protein Phosphatases", HEP, 2005, vol. 167, pp. 295-317.
Denekamp, J., "Endothelial Cell Proliferation as a Novel Approach to Targeting Tumour Therapy", Br. J. Cancer, 1982, vol. 45, pp. 136-139.
Tozer et al., "Disrupting Tumor Blood Vessels", Nature Review, Cancer, 2005, vol. 5, pp. 423-435.
Landuyt et al., "In Vivo Antitumor Effect of Vascular Targeting Combined with Either Ionizing Radiation or Anti-Angiogenesis Treatment", Int. J. Radiation Oncology, Biology, Physics, 2001, vol. 49, No. 2, pp. 443-450.
Siemann et al., "Targeting the Tumor Blood Vessel Network to Enhance the Efficacy of Radiation Therapy", Seminars in Radiation Oncology, 2003, vol. 13, No. 1, pp. 53-61.
Berge et al., "Pharmaceutical Salts", Journal of Pharmaceutical Sciences, 1977, vol. 66, No. 1, pp. 1-19.
Pinkel, Daniel, "Cancer cells, chemotherapy and gene clusters", 2000, Nature Genetics, vol. 24, pp. 208-209.
Hasani et al., "Classification and Toxicities of Vascular Disrupting Agents", Clinical Lung Cancer, 2011, vol. 12, No. 1, pp. 18-25.
Phister et al., "Problem in the Use of Anticancer Drugs in the Elderly", Practical Therapeutics, Drugs, 1989, vol. 37, pp. 551-565.
Repetto, Lazzaro, "Greater Risks of Chemotherapy Toxity in Elderly Patients With Cancer", The Journal of Supportive Oncology, 2003, vol. 1, Suppl. 2, pp. 18-24.
Pasquier et al., "ENMD-1198, a New Analogue of 2-Methoxyestradiol, Displays Both Antiangiogenic and Vascular-Disrupting Properties", Molecular Cancer Therapeutics, 2010, vol. 9, pp. 1408-1418.
Salmon et al. "Monitoring the treatment efficacy of the vascular disrupting agent CA4P", European Journal of Cancer, 2007, vol. 43, pp. 1622-1629.
Spaide, Richard F., "Intravitreal Bevacizumab (Avastin) Treatment of Proloferative Diabetic Retinopathy Complicated by Vitreous Hemorrhage", Retina, The Journal of Retinal and Vitreous Diseases, 2006, vol. 26, No. 3, pp. 275-278.
Nahm et al., "Sustained ability for fibroblast outgrowth from stored neonatal foreskin: a model for studying mechanisms of fibroblast outgrowth", Journal of Dermatological Science, 2002, vol. 28, pp. 152-158.
Benham et al., "Alkaline phosphatase activity in human bladder tumor cell lines", Journal of the Histochemical Society, 1977, vol. 25, No. 4, pp. 266-274.
Desai et al., "The Use of *Xenopus* Egg Extracts to Study Mitotic Spindle Assembly and Function in Vitro", Methods in Cell Biology, vol. 61, pp. 385-412, (1999).
Castoldi et al., "Purification of brain tubulin through two cycles of polymerization—depolymerization in a high-molarity buffer", Protein Expression and Purification, 2003, vol. 32, pp. 83-88.
Laemmli et al., "Cleavage of Structural Proteins during the Assembly of the Head of Bacteriophage T4", Nature, 1970, vol. 227, pp. 680-685.
Schwabacher et al., "Desymmetrization Reactions: Efficient Preparation of Unsymmetrically Substituted Linker Molecules", J. Org. Chem., 1998, vol. 63, pp. 1727-1729.
Mannekens et al., "Efficient Synthesis of 1-Benzyloxypheny-3-phenylacetonse", Synthesis, 2000, No. 9, pp. 1214-1216.
Kyu-Ho Han et al., "Modulation of drug resistance by α-tubulin in paclitaxel-resistant human lung cancer cell lines", European Journal of Cancer, 2000, vol. 36, pp. 1565-1571.
Winter et al., "Carrageenin-Induced Edema in Hind Paw of the Rat as an Assay for Antiinflammatory Drugs", Inactivation of Penicilins by Staphylococci, pp. 544-547, (1962).
Bisagni et al., "A convenient way to dibenzo [c,h]-1,5-naphthyridines (11-aza-benzo[c] phenanthridines)", Tetrahedron, 1996, vol. 52, No. 31, pp. 10427-10440.
Cho et al., "Molecular Modeling of 3-Arylisoquinoline Antitumor Agents Active Against A-549. A Comparative Molecular Field Analysis Study", Bioorganic & Medicinal Chemistry, 2002, vol. 10, pp. 2953-2961.
Cho et al., "Synthesis and Biological Evaluation of 3-Arylisoquinolines as Antitumor Agents", Bioorganic & Medicinal Chemistry Letters, 1998, vol. 8, pp. 41-46.
Cho et al., "Synthesis of New 3-Arylisoquinolinamines: Effect on Topoisomerase I Inhibition and Cytotoxicity", Bioorganic & Medicinal Chemistry Letters, 2003, vol. 13, pp. 4451-4454.
Croisy-Delcey et al., "Diphenyl quinolines and isoquinolines: synthesis and primary biological evaluation", Bioorganic & Medicinal Chemistry, 2000, vol. 8, No. 11, pp. 2629-2641.
Cho et al., "Synthesis and Comparative Molecular Field Analysis (CoMFA) of Antitumor 3-Arylisoquinoline Derivatives", Bioorganic & Medicinal Chemistry, 1998, vol. 6, pp. 2449-2458.
Kitamura et al., "Photolysis of Vinyl Halides. Reaction of Photogenerated Vinyl Cations with Cyanate and Thiocyanate Ions", Journal of Organic Chemistry, 1990, vol. 55, No. 6, pp. 1801-1805.
International Search Report, dated May 9, 2011, from corresponding PCT application.
French Search Report, dated Jan. 18, 2011, from corresponding FR application.

* cited by examiner

A
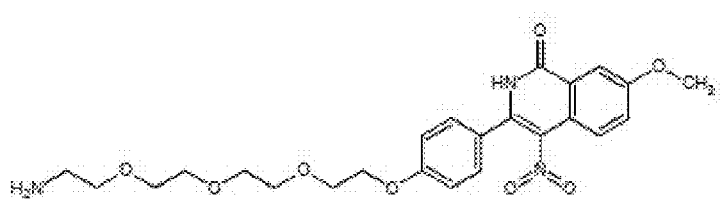
B
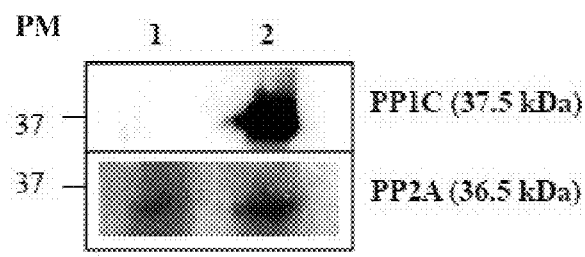
Figure 12

USE OF ISOQUINOLONES FOR PREPARING DRUGS, NOVEL ISOQUINOLONES AND METHOD FOR SYNTHESISING SAME

CONTINUING DATA

This application is a 371 of PCT/FR11/50431 filed Mar. 1, 2011.

The invention relates to the use of isoquinolones for preparing drugs, including novel isoquinolones.

The invention also relates to these novel isoquinolones as well as their synthesis method.

In particular, the invention relates to isoquinolone derivatives used in the treatment of pathological angiogenesis, and more particularly cancer.

Chemotherapy, together with surgery and radiotherapy, remains one of the most used approaches for the treatment of cancer. Although some tens of anticancer compounds have been approved for clinical use, there is still a constant need for more selective, more effective and less toxic novel therapeutics.

Chemotherapy drugs are many and various both as regards their action mechanism and as regards their cell target. The majority of these drugs come within the following categories: alkylating agents, anti-metabolites, plant alkaloids, topoisomerase inhibitors, antitumour and antimitotic antibiotics. Most antimitotic compounds interact with the microtubule cytoskeleton. These compounds act directly on tubulin and/or microtubules, either depolymerizing the microtubules, like vinblastine and vincristine, or stabilizing them like Taxol and its derivatives (Jordan M A and Wilson L, Nat Rev Cancer. 2004, v4(4): pp 253-65). These depolymerizing or stabilizing molecules act mainly on mitosis, and their anti-proliferative activity is due to the suppression of the "physiological" dynamics of the microtubules (Jordan M A et al., Cancer Res. 1991, v51(8): pp 2212-22; Derry W B, Wilson L and Jordan M A, Biochemistry. 1995; 34(7): pp 2203-11). The inhibition of the microtubule dynamics leads to the formation of an aberrant spindle, which maintains the mitotic checkpoint activated, and induces the arrest of cells in metaphase. Prolonged mitotic arrest triggers mitotic catastrophe and therefore cell death (Jordan M A and Wilson L, Nat Rev Cancer. 2004 April; v4(4): pp 253-65). This action mechanism constitutes the basis for the therapeutic use of these compounds, as rapidly dividing cancer cells are particularly sensitive to disturbances of the microtubule dynamics, and are therefore preferentially targeted relative to most of the somatic cells of the organism.

The best-known stabilizing compounds are Taxol and its derivatives, which are widely used for the treatment of breast or ovarian cancer. The compounds destabilizing the microtubules include vinca alkaloids such as vinblastine and the vincristine, preferentially used for haematological tumours but also for certain solid tumours such as lung and testicular cancer.

Also, products of low molecular weight, such as 2-phenyl-4-quinolones (Led et al., J. Med. Chem., 1994, v37: pp 1126-35 and pp 3400-07; 2009, 52, 4883-4891) or 1,2,3,4-tetrahydro-2-phenyl-4-quinolones (Led et al., J. Med. Chem., 1998, v41, pp. 1155-62) have also shown tubulin polymerization inhibition properties (anti-tubulin compounds).

However, although anti-tubulin molecules are effective on a large number of cancers, and widely used clinically, the peripheral neurotoxicity and resistance phenomena developed by mammals, in particular humans, demonstrate the need to seek novel anti-mitotic agents acting on new targets.

By "mammal", is meant in particular a domestic animal.

Another large class of anticancer drugs is represented by enzyme inhibitors, such as methotrexate (dihydrofolate reductase (DHFR) inhibitor), fluorouracile (thymidylate synthase inhibitor) Gleevec and BMS-354825 (Bcr-Abl tyrosine kinase activity inhibitors), erlonitib (epidermal growth factor receptor (EGFR) inhibitor), PALACI-1040 and PD0325901 (mitogen-activated protein kinase (MAPKK) inhibitors, PALA (aspartate transcarbamoylase inhibitor), flavopiridol (Kaur G et al., J Natl Cancer Inst. 1992, v84(22): pp 1736-40) and R-roskovitine (Meijer L et al., Eur J. Biochem. 1997, v243(1-2): pp 527-36), cyclin-dependent kinase inhibitors.

Among the enzyme inhibitors, in vitro pre-treatment with benzopyrone derivatives, poly-ADP ribose polymerase (pADPRT) inhibitors and in particular with the compound 5-iodo-6-amino-1,2-benzopyrone ($INH_2BP$) of E-ras-transformed cow endothelial cells and human prostate adenocarcinoma DU145 cells has demonstrated a tumourigenicity inhibition activity (on these pre-treated cells) in the nude mouse xenograft model.

Other pADPRT inhibitory compounds, such as isoquinolinone, are described in international application WO 98/51307 (Octamer), for the treatment of inflammation and inflammatory diseases, arthritis and heart attack.

Protein phosphorylation is defined by the transfer of a high-energy phosphate from ATP (adenosine triphosphate) molecules to a protein via a protein kinase. Its removal by a protein phosphatase is called dephosphorylation. More than 98% of the phosphate attached to the proteins is bound via a serine or threonine (Berndt, Progress in Cell Cycle Res. 2003, (5): pp 497-510).

The reversible phosphorylation of proteins represents the most important phenomenon for the rapid regulation of the activities of proteins in eukaryotic cells. It is involved in the regulation (activation/inactivation) of various cell activities, such as for example gene expression, the cell cycle and cell differentiation.

The phosphorylation/dephosphorylation cycles are ensured by a large number of kinases (518) and phosphatases (more than 130) (Alonso et al., Cell. 2004 (117): pp 699-711). The latter include the PPP (Phospho-Protein Phosphatase) family comprising: PP1, PP2A, PP2B, PP4, PPS, PP6 and PP7. And, within this family, the two protein phosphatases PP1 and PP2A are responsible for more than 90% of the intracellular serine/threonine phosphatase activity (Stewart et al., Bioorg. Med. Chem., 2007 (15): pp 7301-10). PP1 and PP2A are enzymes formed by a catalytic sub-unit associated with one or more regulatory sub-units. These regulatory parts regulate the catalytic part and determine the intracellular localization of the holoenzyme and its specificity. In this way, the catalytic sub-units can act on a large panel of substrates.

The catalytic domain of protein phosphatase 1 (PP1C) exists in three isoforms: alpha, beta (also called delta) and gamma. In mitosis, these are found on the mitotic spindle, to be precise at the level of the centrosome, kinetochores, microtubules and chromosomes (Andreassen P R et al., J. Cell Biol. 1998, 141(5): pp 1207-15; Trinkle-Mulcahy L and Lamond A I, Curr Opin Cell Biol. 2006, (6): pp 623-31).

The PP1 participates, via the regulatory sub-units controlling its subcellular localization, in numerous physiological processes such as protein synthesis, cell division, glycogen metabolism, apoptosis, calcium transport or also muscle contraction.

Numerous articles have shown that PP1 is involved in regulation of the cell cycle:
(i) PP1 blocks entry into S phase, stopping the cells in G1 (Berndt N et al., Curr Biol 1997, v7: pp 375-86).
(ii) PP1 activity is necessary for entry into M phase (Margolis S S et al., EMBO J. 2003, 22(21): pp 5734-45).

(iii) PP1 is necessary for dephosphorylation of histone H3 and is opposed to the activity of Aurora-B kinase (Goto H et al., Genes Cells. 2002, 7(1): pp 11-7).
(iv) PP1 is involved in the cohesion of the centrioles forming the centrosome (Meraldi P and Nigg E A, J Cell Sci. 2001, 114 (Pt 20): pp 3749-57).
(v) PP1 activity participates at the checkpoint associated with DNA damage (Tang X et al., 2008, Mol Cell Biol., 28(8): pp 2559-66).
(vi) PP1 is indispensable for inhibition of the spindle checkpoint and disassembly of the kinetochores on leaving the M phase (Emanuele M J et al., J. Cell Biol. 2008, 181(2): pp 241-54).
(vii) The dephosphorylation of the phosphoproteins by PP1 is indispensable for leaving the M phase (Wu J Q et al. Nature Cell Biol, 2009, v11(5): pp 644-51).
(viii) PP1 plays a role in M/G1 transition by contributing to the reassembly of the nuclear envelope on completion of mitosis by dephosphorylating the B lamins (Thompson L J et al., 1997, J Biol. Chem. 1997, 272(47): pp 29693-7).

All the above elements (i) to (viii) suggest that selective PP1 inhibition would have a profound effect on cell cycle regulation, particularly with regard to the M phase. And the use in chemotherapy of anti-proliferative drugs having an effect on the progression of the cell cycle, makes PP1 a target of choice for the development of novel anti-cancer molecules.

Furthermore, PP1 is involved in cancer progression. In fact, analysis of transcripts of 60 cancer cell lines (NCI-60: http://genome-www.stanford.edu/nci60/) has shown that the different isoforms of PP1 were overexpressed in cancers of the colon, breast, lung and central nervous system (Ross D T et al., 2000; Nat. Genet., v24(3): pp 227-35).

Furthermore, gene amplification on chromosome band 11q13 is frequently observed in orophangeal squamous cell carcinomas (OSCC), and this gene amplification would be under the control of the PP1CA gene (encoding the catalytic sub-unit of PP1, alpha isoform). Other studies suggest that PP1CA is involved directly in tumourigenicity and/or tumour progression in this type of cancer (Hsu L C et al., Oncogene, 2006, v25 (40): pp 5517-26).

There are numerous molecules inhibiting the activity of PP1, most not being selective and preferentially targeting PP2A.

For example, PP1 and PP2A are inhibited by a large number of natural toxins, such as okadaic acid, calyculin A, tautomycin, tautomycetin, or fostriecin (McConnell J L and Wadzinski B E, Mol Pharmacol, 2009, v75: pp 1249-61). Among these toxins, fostriecin exhibits a strong selectivity for PP2A (40,000 times), whereas tautomycin and tautomycetin (which are more PP1-specific) show a weak selectivity for PP1 relative to PP2A (4 times and 40 times respectively). Phosphatidic acid exhibits a selectivity for PP1 100 times greater than for PP2A, but this window remains closed for a PP1-specific study with inhibitors (Stewart S G et al., Bioorg. Med. Chem. 2007 (15): pp 7301-10).

The discovery of a PP1-selective inhibitor would make it possible to separate the effects of PP1 inhibition from those of PP2A inactivation.

Although the potential of the protein phosphatase inhibitors as anticancer drugs has been recognized for a long time, only fostriecin and cantharidin have been clinically evaluated. Fostriecin, a PP2A-selective inhibitor, has been tested in a phase I clinical trial, in which it has proved inactive due to its structural instability (Lê L H et al., Invest New Drugs. 2004, v22(2): pp 159-67). Similarly, trials with cantharidin (non-selective PP2A and PP1 inhibitor) have also been discontinued due to too-high nephrotoxicity (Honkanen; "Serine/Threonine Protein Phosphatase Inhibitors with Antitumor Activity", in Inhibitors of Protein Kinases and Protein Phosphatases, Berlin: Springer-Verlag, 2005, v167, ISBN 3-540-21242-6: pp 295-317).

The idea of destroying tumour neovessels in order to treat cancer, put forward by J. Denekamp in 1982, gave rise to a new class of anticancer molecules, "VDAs", or Vascular-disrupting Agents (Denekamp J, Br J Cancer. 1982, 45(1): pp 136-9; Tozer G et al., Nature Rev. 2005, v5: pp 423-35). These compounds are clearly different from anti-angiogenic agents which interfere with the appearance and growth of the new vessels.

The VDA molecules act on the endothelial cells constituting tumour neovessels and cause a collapse of the vascular system, stopping the blood flow and rapidly leading to necrosis of the tumour mass.

Most of the vascular-disrupting agents (VDAs) are capable of depolymerizing the microtubules of the endothelial cells constituting the neovessels. This depolymerization causes a rounding of the cell and a veritable collapse of the vessel, which thus prevents the blood from flowing.

Among the anti-tubulin VDAs, there may be mentioned: ZD6126 (ANG453; AZD6126), CA4 (Combretastatin A-4), CA4P (Zybrestat, OXi2021, Fosbretabulin, Combretastatin A-4 disodium phosphate), $BNC_1 05$, MN-029 (Denibulin), CYT997, AVE8062 (AC7700, Ombrabulin), NPI-2358 (Diketopiperazine), EPC2407 (MX-116407, MX-2407), TZT-1027 (Auristatin PE, Soblidotin, NSC-654663), MPC-6827 (Azixa), ABT751, Trisenox (Arsenic trioxide), OXi4503 (CA1P), 2-Methoxyestradiol (Panzem, NSC-659853; 2-ME).

There is also another category of VDAs which do not act on tubulin, which include: SU6668 (VEGFR, PDGFR, FGFR inhibitor), PTK787 (ZK222584; VEGFR1, 2, 3 inhibitor), ZD6474 (VEGFR2 and EGFR inhibitor), and Exherin (ADH-1, Adherex; N-cadherin inhibitor), ASA404 (DMXAA, AS1404; inducer of cytokines such as TNF and INF) and FAA (Flavone Acetic Acid, NSC 347512, LM975).

The selectivity associated with these agents is mainly due to a higher sensitivity of the immature endothelial cells (more fragile and more permeable) forming the walls of the new vessels (Tozer G et al., Nature Reviews. 2006, v5: pp 423-35).

Significantly, antitumour drugs in the VDA class are more active on large tumours with aggressive growth, rather than on small tumours, probably because the latter are less vascularized than large neoplasias (Landuyt W., Intl J of Rad Oncol Biol Phys. 2001, v49(2): pp 443-50; Sieman D W and Shi W, Sem in Rad Oncol. 2003, v13(1): pp 53-61).

The VDAs therefore seem to be particularly suitable for the treatment of pathological angiogenesis. The latter, characterized by the excessive and/or abnormal formation of blood vessels, is involved in a large number of diseases, especially the proliferative diseases, particularly those dependent on the growth of the vessels. Excessive and/or abnormal angiogenesis is observed in cancer, psoriasis, infectious diseases (the pathogens can themselves express angiogenic factors, induce the expression of such factors by the host, or can transform endothelial cells), autoimmune diseases (with activation of the leucocytes and/or mastocytes).

Furthermore, in adipose tissue, angiogenesis can be induced by eating too much fat (the use of angiogenesis inhibitors induces weight loss).

Retinal neovascularization, a major cause of blindness, is a complication of a large number of diseases, including diabetic retinopathy, age-related macular degeneration, and vascular occlusions.

One of the purposes of the invention is to provide selective PP1 inhibitors, additionally possessing VDA activity, and/or microtubule depolymerization activity, for preparing a drug intended for the prevention or treatment of pathological angiogenesis and/or benign or malignant (cancerous) tumours, irrespective of their origin or size, within the context of a first-line treatment or in mammals, in particular humans, resistant to conventional treatments.

Another purpose of the invention is to provide pharmaceutical compositions containing PP1-selective inhibitors, additionally possessing VDA activity, and/or a microtubule depolymerizing activity, for the prevention or treatment of pathological angiogenesis and/or of benign or malignant tumours.

The present invention relates to the use of at least one compound of general formula (I) below as a protein phosphatase 1 and/or tubulin polymerization, and/or vascular-disrupting agent (VDA) inhibitor, for preparing a drug intended for the prevention and/or treatment of patients suffering from pathological angiogenesis, in particular retinopathies, benign tumours, or malignant (cancerous) tumours.

The present invention relates to the use of at least one compound of general formula (I) below:

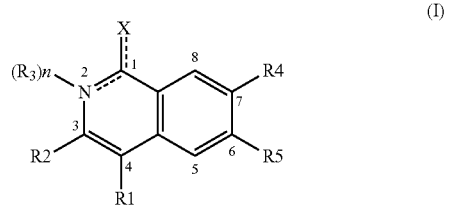

(I)

in which:
1) the bond between carbon 1 and the X group is single or double, the bond between nitrogen 2 and carbon 1 can be single or double
 it being understood that:
  a) when the bond between X and said carbon 1 is double, then the bond between nitrogen 2 and carbon 1 is single:
 and,
  b) when the bond between X and said carbon 1 is single, then the bond between nitrogen 2 and carbon 1 is double and formula I corresponds to an aromatic system of formula I-A

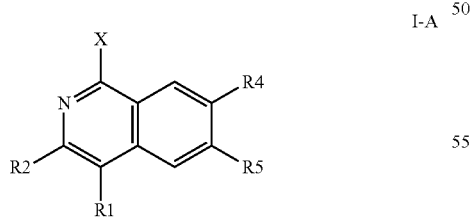

I-A 2) n represents 0 or 1,
3) X represents:
  a) when n=1:
   O, S, NH, N—($C_1$-$C_6$)alkyl,
  b) when n=0:
   OH, $OPO_3H_2$, OPO—(O—($C_1$-$C_2$)alkyl)$_2$, the alkyl being optionally substituted by one or more fluorines,
   O—($C_1$-$C_6$)alkyl, in particular $OCH_3$, the alkyl being optionally substituted by one or more fluorines, O($C_3$-$C_6$)cycloalkyl, $NH_2$, NH—($C_1$-$C_6$)alkyl, N—[($C_1$-$C_6$)alkyl]$_2$, NH—($C_3$-$C_6$)cycloalkyl, N—[($C_3$-$C_6$)cycloalkyl]$_2$, SH, S—($C_1$-$C_6$)alkyl, the alkyl being optionally substituted by one or more fluorines, in particular $SCH_3$, S($C_3$-$C_6$)cycloalkyl, $SO_3H$, NH—$CH_2$-aryl or heteroaryl,
   OPh, SPh, $OCH_2$Ph, $SCH_2$Ph, the phenyl of these four groups being able to be substituted or not by one or more ($C_1$-$C_6$)alkyls, the alkyl being optionally substituted by one or more fluorines,

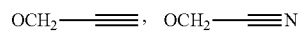

$OCH_2$——≡, $OCH_2$——≡N

4) R1 represents:
  H, a halogen, OH, $OPO_3H_2$, OPO—(O—($C_1$-$C_2$)alkyl)$_2$, the alkyl being optionally substituted by one or more fluorines,
  $CF_3$, $CH_2OR'$, R' representing H or ($C_1$-$C_6$)alkyl, the alkyl being optionally substituted by one or more fluorines, CHO,
  $CO_2R''$, R'' representing H, ($C_1$-$C_6$)alkyl, the alkyl being optionally substituted by one or more fluorines,
  $CONR_cR_d$, $CH2SO_2NR_cR_d$, $CH2NHSO_2Rc$, $R_c$ and $R_d$ representing independently of each other: H, a $C_1$-$C_6$ alkyl, and $NR_cR_d$ represents an amino acid bound by its function amine, in particular a serine or a threonine, a $C_3$-$C_6$ cycloalkyl, or $R_c$ and $R_d$ represent together a $C_2$-$C_6$ alkyl,
  $NO_2$, $N_3$, ≡, CN, C(=N)$NH_2$, $SO_3H$, $SO_2NH_2$, $SO_2NHCH_3$, $NHSO_2CH_3$, $CH_2SO_2NR_cR_d$, $CH_2NHSO_2Rc$, $SO_2$—NRaRb, $SO_2$-imidazole, $NR_aR_b$, where:
   $R_a$ and $R_b$ represent independently of each other: H, a $C_1$-$C_6$ alkyl, a $C_3$-$C_6$ cycloalkyl, or
   Ra is H, a $C_1$-$C_6$ alkyl, a $C_3$-$C_6$ cycloalkyl, and Rb=$COR_f$, $COOR_f$ or $CONR_eR_f$ and $R_f$ representing H, a $C_1$-$C_6$ alkyl, a $C_3$-$C_6$ cycloalkyl or an amino acid chain (such as CH($CH_2OH$)$NH_2$ for serine) $R_a$ and $R_b$ represent together a $C_2$-$C_6$ alkyl,
   $R_a$ and $R_b$ can form a $C_5$ to $C_7$ ring, in particular a pyrrolidine, a piperazine, a morpholine, a thiomorpholine,
   a heteroaryl, substituted or not, in particular a pyridine, an imidazole, an oxazole, a triazole, a pyrrole, a tetrazole.
5) R2 represents:
a phenyl substituted or not by one to three substituents chosen from:
a halogen, an OH, NHRa,
ORe, Re representing a benzyl, a methylene triazole, substituted or not, in particular by a $C_1$-$C_6$ alkyl,
$OPO_3H_2$, OPO—(O—($C_1$-$C_2$)alkyl)$_2$, the alkyl being optionally substituted by one or more fluorines, an $NH_2$,
an NH—CORc group in which Rc represents H, a $C_1$-$C_6$ alkyl, a $C_3$-$C_6$ cycloalkyl or an amino acid chain (such as CH($CH_2OH$)$NH_2$ for serine),
an O—($C_1$-$C_6$)alkyl, in particular $OCH_3$, the alkyl being optionally substituted by one or more fluorines,
an O—COR1 where R1 represents O—($C_1$-$C_6$)alkyl, or NRiRii, Ri and Rii being able to be $C_1$-$C_6$ alkyl,
a $C_2$-$C_4$ alkyl group, the alkyl group being optionally substituted by one or more fluorines, a $C_2$-$C_4$ alkenyl group, substituted or not, a $C_2$-$C_4$ alkynyl group, substituted or not, in particular by a trimethylsilyl, a tert-butyl, a hydroxy-2-propyl or an isopropyl a heteroaryl, substituted or not, in particular a pyridine, an imidazole, an oxazole, a triazole, a pyrrole, a benzofuran, a thiophene, a benzothiophene, an indole, a cyclohexyl, a piperazine, a morpholine, a thiomorpholine, a piperidine, a 4-($NH_2$—($CH_2$—$CH_2O$)p)Ph group in which p is an integer from 1 to 6

6) R3 represents:

H, ($C_1$-$C_6$)alkyl, the alkyl being optionally substituted by one or more fluorines, ($C_3$-$C_6$)cycloalkyl, OH, $OPO_3H_2$, OPO—(O—($C_1$-$C_2$)alkyl)$_2$, $OSO_3H$, $SO_3H$, O—($C_1$ to $C_6$)alkyl, $NH_2$, NH—($C_1$-$C_6$)alkyl, N—[($C_1$-$C_6$)alkyl]$_2$, NH—($C_3$-$C_6$)cycloalkyl, N—[($C_3$-$C_6$)cycloalkyl]$_2$, a propargyl group, $CH_2CN$, $(CH_2)_p$OH, p varying from 1 to 6, $CH_2OPO_3H_2$, $CH_2$OPO—(O—($C_1$-$C_2$)alkyl)$_2$, $CH_2CH_2F$, $CH_2CHF_2$, $CH_2CF_3$, 7) R4 and R5 represent independently of each other:

H, OH, $OPO_3H_2$, OPO—(O—($C_1$-$C_2$)alkyl)$_2$, the alkyl being optionally substituted by one or more fluorines, an O—($C_1$-$C_6$)alkyl, in particular $OCH_3$, the alkyl being optionally substituted by one or more fluorines, a $C_1$-$C_6$ alkyl, the alkyl being optionally substituted by one or more fluorines, a $C_3$-$C_6$ cycloalkyl, a halogen, R4 and R5 represent together a ($C_1$-$C_2$)dioxy alkenyl optionally substituted by one or more fluorines, and pharmaceutically acceptable salts, as vascular-disrupting agents, for preparing a drug intended for the prevention and treatment in the case of mammals, in particular humans, suffering from pathological angiogenesis, in particular retinopathies, or benign or malignant (cancerous) tumours.

In this embodiment, general formula (I) and the dotted lines can therefore correspond to three structures a), b) and c) respectively:

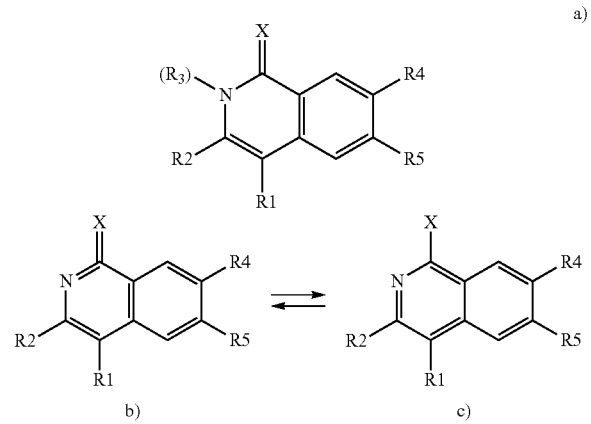

The different terms defined below have the same meaning throughout the description:

n=0 signifies that there is no substituent R3 and as a result, the formula corresponds to b) or c) above.

n=1 signifies that there is a substituent R3 which can be either H or the other substituents defined above and the formula therefore corresponds to a) above.

The term halogen denotes: bromine (Br), chlorine (Cl), fluorine (F) and iodine (I), The term alkyl denotes linear or branched hydrocarbon-containing radicals which derive from alkanes by loss of a hydrogen. Unless otherwise specified, they comprise from 1 to 10 carbon atoms and include all possible positional isomers.

The term cycloalkyl corresponds to a cyclized alkane and comprises from 3 to 10 carbon atoms.

An amino acid bound by its acid function denotes any natural or non-natural amino acid which is bound by an amidic bond (NH—CO) between an amine of the molecule and the main acid function or of the side chain in the case of acidic amino acids such as the aspartic or glutamic acid of the amino acid.

The term substituted phenyl denotes a phenyl group which can comprise from 1 to 5 substituents, said substituents being able to be independently of each other, a halogen, a hydroxy, a thiol, a cyano, an azido, a nitro, an amino optionally substituted by a mono- or di($C_{1-4}$)alkyl, a ($C_{1-4}$)alkyl, a ($C_{3-6}$) cycloalkyl, a ($C_{2-4}$)alkenyl, a ($C_{2-4}$)alkynyl, ($C_{1-4}$)alkyloxy or a phenyl.

The term substituted heteroaryl denotes an aromatic ring comprising at least one heteroatom such as O, N or S, and which can comprise one or more substituents, independently of each other, as defined above.

The $R_4$ and $R_5$ groups defined above can also represent a heteroaryl or a phenyl, optionally substituted by the substituents defined above, but also by a phosphate group.

In the same way, the $R_1$ group defined above, when it corresponds to a phenyl, substituted or not, or a heteroaryl, substituted or not, can also be substituted by a phosphate group.

The expression "and the pharmaceutically acceptable salts" denotes the salts of the molecules of the invention which possess a salifiable function such as:

a carboxylic, or phosphoric ($OPO_3H$) or sulphonic ($SO_3H$) or sulphuric ($OSO_3H$) acid function, or a phenol function, said salt being obtained with organic or mineral bases, in order to lead for example to alkali metal salts, such as lithium, sodium or potassium salts.

an amine function, substituted or not, said salt being obtained by reaction of an inorganic acid, an organic acid or an alkyl halide, on the amine in order to produce a quaternary ammonium.

Examples of inorganic acids making it possible to obtain pharmaceutically acceptable salts include, but are not limited to, hydrochloric acid, hydrobromic acid, nitric acid, carbonic acid, formic acid, monohydrogen carbonic acid, phosphoric acid, monohydrogen phosphoric acid, dihydrogen phosphoric acid, perchloric acid, sulphuric acid, monohydrogen sulphuric acid, hydriodic acid.

Examples of organic acids making it possible to obtain pharmaceutically acceptable salts include, but are not limited to, acetic acid, lactic acid, propionic acid, butyric acid, isobutyric acid, palmic acid, maleic acid, glutamic acid, hydroxymaleic acid, malonic acid, benzoic acid, succinic acid, glycolic acid, suberic acid, fumaric acid, mandelic acid, phthalic acid, salicylic acid, benzenesulphonic acid, p-toluenesulphonic acid, citric acid, tartaric acid, methanesulphonic acid, hydroxynaphthhoic acid.

The salts of amino acids, such as the arginates and their equivalents are also included as well as the salts of organic acids such as glucuronic acid or galacturonic acid and their equivalents (see, for example, Berge et al., "Pharmaceutical Salts", Journal of Pharmaceutical Science, 1977, 66, 1-19).

The alkyl halides making it possible to obtain pharmaceutically acceptable salts include, but are not limited to, the alkyl bromides, iodide, fluoride or chloride in which said alkyl residue is saturated or non-saturated, linear or branched, with 1 to 20 carbon atoms, or an O-cycloalkyl group of 3 to 8 carbon atoms.

The term (abnormal) pathological angiogenesis denotes a pathological process consisting of a proliferation, and then the persistence of said proliferation, of the blood vessels in "abnormal" tissues, for example and without being limited to the latter, in tumour tissues, or in healthy tissues but "in abnormal positions" or exhibiting "abnormal morphology".

The expression "treatment of pathological angiogenesis" signifies that mammals, in particular humans, suffer from a diagnosed angiogenesis/pathological vascularization and will be treated with a drug in order to bring about the disappearance of said angiogenesis/vascularization.

The expression "prevention of pathological angiogenesis" signifies that a mammal, in particular a human, has not been diagnosed, i.e. is not suffering from a pathological angiogenesis, but is likely to develop one, and that taking or administering a drug of the invention prevents the development or appearance of a pathological angiogenesis.

The prevention of pathological angiogenesis can be envisaged for a mammal, in particular a human, already suffering from a pathological angiogenesis, within the context of a therapy aimed at limiting the expansion or prolongation of the pathological angiogenesis process.

This pathological angiogenesis process is observed in numerous pathologies such as retinopathy which denotes all the diseases of the retina, in particular the diabetic, hypertensive or pigmentary retinopathies, macular degeneration, rubeosis, neovascular glaucoma, or retinopathy of prematurity.

Pathological angiogenesis is also characteristic of, but not limited to, skin lesions in psoriasis or myocardial angiogenesis, atherosclerosis, coronary collateral angiogenesis, cerebral collateral angiogenesis, arteriovenous malformations, angiogenesis in limb ischaemia, angioplasty or arteriovenous shunt, DiGeorge syndrome, vascular malformations, hereditary hemorrhagic telangiectasia, cavernous or cutaneous haemangioma, lymphatic malformations, arteriopathy, neovascularization of atherosclerotic plaques, haemangioma, haemangiopericytoma, kaposiform haemangio-endothelioma, angiokeratoma, capillary haemangioma, lymphangioma, acoustic neuroma, neurofibromas, angiofibroma, pyogenic granuloma, phakomatoses, Rendu-Osler-Weber disease.

The term "tumour" denotes a neoformation of body tissues ("neoplasia"), linked to a deregulation of cell growth of benign or malinant type.

The expression "benign tumours" denotes slow growing, well delimited tumours whatever their origin or size, formed by a homogeneous tissue with well differentiated cells, with low mitotic activity, without metastases.

The expression "cancerous tumours" or "malignant tumours" denotes rapidly growing and invasive, poorly delimited tumours, irrespective of their origin or size, formed by a heterogeneous tissue with non-differentiated cells described as immature, with significant cell division, often with metastases.

The expressions "cancerous tumours" or "malignant tumours" also denote without being limited thereto: primary tumours, tumour metastases, solid tumours, hematopoietic cancers, leukaemias, lymphomas, carcinomas, adenocarcinomas, sarcomas, melanoma, head and neck carcinoma, cancer of the oesophagus, oral cancer and cancer of the pharynx, cancer of the larynx, cancer of the bladder, colorectal cancer, ovarian cancer, cancer of the uterus, cancer of the penis, cancer of the vulva and of the vagina, cervical cancer, prostate cancer, renal cancer, skin cancer, bone cancer, cancer of the joints and joint cartilages, testicular cancer, stomach cancer, gastrointestinal cancer, genitourinary cancer, lung cancer, thymoma, mesothelioma, teratoma, brain cancer, liver cancer, pancreatic, glioma, glioblastoma, oligoastrocytoma, meningioma, adenoma of the hypophysis, glioblastoma multiforme, medulloblastoma, ependymoma, anaplastic astrocytoma, oligodendroglioma, thyroid cancer, anaplastic thyroid cancer, haemangiosarcoma, Kaposi's sarcoma, lymphangiosarcoma, malignant ganglion and extra-ganglion lymphomas, Hodgkin's lymphoma, indolent lymphomas non-hodgkin's lymphomas, retinoblastoma.

One of the advantages of the molecules of the invention is that they possess vascular-disrupting properties rapidly causing necrosis of the tumour by mechanical rupture of the blood network in the tumour. Furthermore, by disrupting the blood flow, the molecules of the invention (as well as other anticancer products administered beforehand or simultaneously with the molecules of the invention) are retained in the tumour, rather than being eliminated by the blood circulation which leads to increased efficiency.

According to another aspect, the present invention relates to the use of at least one compound of general formula (I) defined above as a protein phosphatase 1 inhibitor.

The expression "protein phosphatase 1" denotes both the catalytic domain of the protein phosphatase 1C (PP1C) in one of its three isoforms and the catalytic sub-unit of myosin light chain phosphatase (MLCP).

The expression "protein phosphatase 1" also denotes protein phosphatase 1 holoenzyme to the extent that it contains one of its three isoforms (alpha, beta/delta and gamma) of the catalytic part of the protein phosphatase 1.

It is known that the different isoforms of PP1 are overexpressed in the cell lines originating from several types of cancers, such as cancer of the colon, breast, lung and CNS (Ross et al., Nature Genet. 2000; v24(3): pp 208-9). Furthermore, the gene amplification of the chromosome band 11q13 is often observed in squamous mouth cancer. The PPP1CA gene (catalytic sub-unit of PP1, alpha isoform) is associated with this amplification of 11q13, which is in turn correlated with the overexpression of PP1 alpha. Reduction in the level of PP1 alpha with siRNAs makes it possible to stop the proliferation of squamous mouth cancer cells in vitro (Hsu et al., Oncogene. 2006, v25(40): pp 5517-26). As a result, a PP1-selective inhibitor would allow the treatment of this type of cancer.

A second advantage of the molecules of the invention is that they possess selective inhibition of protein phosphatase 1 as opposed to protein phosphatase 2A which gives them an advantage over the non-specific inhibitors by limiting the toxic effects.

In an advantageous embodiment, the present invention relates to the use of at least one compound of general formula (I) defined above, as a vascular-disrupting agent, protein phosphatase 1 inhibitor, and antiproliferative agent, for preparing a drug intended for the prevention and treatment in the case of mammals, in particular humans, suffering from pathological angiogenesis, in particular retinopathies, or benign or malignant (cancerous) tumours.

By "antiproliferative" agent is meant a drug which interferes with the proliferation of cells irrespective of the phase of the cell cycle affected by said agent.

The interference of a PP1 inhibitor with the cell cycle (as detailed above) is equivalent to the antiproliferative effect.

Another advantage of the molecules of the invention is that they possess both vascular-disrupting properties and selective inhibition of protein phosphatase 1.

In an advantageous embodiment, the present invention relates to the use of at least one compound of general formula (I) defined above, as a vascular-disrupting agent and protein phosphatase 1 inhibitor and antiproliferative agent, but devoid of tubulin polymerization inhibiting activity. The tubulin polymerization inhibiting activity can be harmful in the case where mammals, in particular humans, are likely to develop a peripheral neuropathy (Clinical Lung Cancer, Volume 12, Number 1/January 2011, pages 18-25).

The tubulin polymerization inhibiting activity can also cause inhibition of haematopoieisis.

As a result, one of the advantages of this type of compound is that they can target a population of mammals, in particular humans, likely to develop a peripheral neuropathy without causing the inhibition of haematopoieisis and in particular they can treat aged mammals, in particular humans.

The anti-PP1 compounds are capable of exhibiting toxicity lower than or at least very different from that of the anti-tubulin agents, which cause peripheral neurotoxicity effects, especially in aged mammals, in particular humans, (Phister J E et al., Drugs, 1989, 37[4] pp. 551-65; Repetto L., J Support Oncol., 2003, 1 [4 Suppl 2]: pp 18-24).

In an advantageous embodiment, the present invention relates to the use of at least one compound of general formula (I) defined above, as a vascular-disrupting agent, tubulin polymerization inhibitor, and antiproliferative agent, for preparing a drug intended for the prevention and treatment in the case of mammals, in particular humans, suffering from pathological angiogenesis, in particular retinopathies, or benign or malignant (cancerous) tumours.

In this embodiment, the compound of the invention possesses little or no PP1 inhibiting activity.

A further advantage of the molecules of the invention is that they possess the ability to depolymerize the microtubules in the cells, thus conferring an anti-mitotic effect upon the molecules of the invention, thus allowing a cell proliferation inhibiting action via a mechanism independant of PP1 inhibition.

In an advantageous embodiment, the present invention relates to the use of at least one compound of general formula (I) defined above, as a protein phosphatase 1 and tubulin polymerization inhibitor, vascular-disrupting agent and antiproliferative agent, for preparing a drug intended for the prevention and treatment in the case of mammals, in particular humans, suffering from pathological angiogenesis, in particular retinopathies, or benign or malignant (cancerous) tumours.

Another advantage of the molecules of the invention is that they possess, in addition to the vascular-disrupting properties and PP1 inhibition described above, the ability to depolymerize the microtubules in the cells, thus conferring an anti-mitotic effect upon the molecules of the invention.

The molecules of the invention, due to their PP1 inhibiting activity and their activity of depolymerization of the microtubules in the cells, resulting in an antiproliferative effect, in addition to their VDA activity, are capable of being active on tumours irrespective of the size and origin of these tumours. The necrosis of the tumour caused by this triple activity is rapid and takes place within 24 hours or less making it possible to more particularly target large tumours and also makes it possible to target inoperable mammals, in particular humans.

The presence of the four activities (anti-PP1, anti-tubulin and anti-proliferative and VDA) mentioned above confers extremely useful properties upon the molecules of the invention and in particular the possibility of carrying out a therapy on mammals, in particular humans, without their developing resistance.

Another advantage of the molecules of the invention is that they are active after administration by parenteral or oral route.

Yet another advantage of the molecules of the invention, is that that they do not exhibit toxicity in vivo, the maximum tolerated oral dose being able to be estimated between 200 and 400 mg/kg in a nude mouse.

The compounds of the invention are very active in vitro on human umbilical vein endothelial cells (HUVEC) as well as on human mammary epithelial cells (HMEC), with a concentration inhibiting cell proliferation by half (GI50) much lower than that of cancer cell lines or that of primary skin fibroblasts (FIGS. 7 and 8 and Table I).

The results obtained with the HMEC cells are representative of the VDA activity.
(Pasquier E., et al., Mol Cancer Ther; 9(5) 2010. Pp 1408-18: ENMD-1198, a new analogue of 2-methoxyestradiol, displays both antiangiogenic and vascular-disrupting properties).

The compounds of the invention are capable of preferentially targeting endothelial tumour cells and distinguising the "mature" endothelial cells of healthy tissues, from "young" endothelial tumour cells recently conveyed into the tumour by the blood flow, i.e. having an action only on the "young" cells and not on the "mature" endothelial cells.

In an advantageous embodiment, the present invention also relates to the use of at least one compound of formula (I), in which:
when at least one of the X, R2, R4 and R5 groups represents a phosphate group: $OPO_3H_2$, alkyl phosphate: $OPO-(O-(C_1-C_2)alkyl)_2$, and/or
the R3 group represents a $CH_2OPO_3H_2$ or $CH_2OPO-(O-(C_1-C_2)alkyl)_2$ group,
and/or
at least one of R1 and R2 groups represents a peptide or an amino acid bound by its acid function, in particular a serine.

In this case the molecules of the invention are considered as prodrugs, i.e. the active molecule will be released into the organism by hydrolysis using an enzyme, for example a phosphatase, or due to the pH, in order to produce a free OH function or $CH_2OH$, and/or by hydrolysis using an aminopeptidase in order to produce a free $NH_2$ function, after administration of the prodrug. It should be noted here, that the abnormal environment of the tumour vessels is associated with the increased expression of alkaline phosphatase at the surface of the endothelial cells, which allows the dephosphorylation of the prodrugs, such as CA4P (Combretastatin A4 Disodium Phosphate).

In an advantageous embodiment, the invention relates in particular to the use of at least one of the compounds of general formula (I) defined above or of their pharmaceutically acceptable salts, as a protein phosphatase 1 and/or tubulin polymerization inhibitor, and/or vascular-disrupting agent and/or antiproliferative agent, for preparing a drug intended for the prevention and/or treatment in the case of mammals, in particular humans, suffering from benign or malignant (cancerous) tumours, said mammals, in particular humans, suffering from tumours resistant to the conventional treatments or not being capable of developing resistance after treatment with said drug.

By "conventional treatment" is meant any antitumour treatment well known to a person skilled in the art, such as but without being limited to: surgery, radiotherapy, chemotherapy, so-called "targeted" therapy, gene therapy, therapy with bioproduits, including passive or active immunization products.

By "chemotherapy" is meant a method of treatment with chemical substances in order to treat a disease, in particular tumours. By "chemical substance for chemotherapy", is meant the following compounds, without being limited thereto, such as 5-fluorouracil, gemcitabine, hydroxyurea, alkylating agents, cisplatin, paclitaxel, the vinca alkaloids such as vinblastine or vincristine, methotrexate, the camptothecins, etoposide, daunorubicin and doxorubicin, and other compounds well known to a person skilled in the art.

By "targeted therapy" is meant a therapeutic product or strategy, with a focussed strategy, which acts on a well-defined target or biological signalling pathway, which, once inactivated, leads to the regression or destruction of the cancer. By "substance for targeted therapy" is meant substances of chemical or protein/peptide origin, without being limited thereto, such as imatinib mesylate (Gleevec®), gefinitib (Iressa®), bevacizumab (Avastin®), trastuzumab (Herceptin®), cetuximab (Erbitux®), iodine[131]-tositumomab (Bexxar®), rituximab (Rituxan®), alemtuzumab (Campath®), ibritumomab tiuxetan (Zevalin®) or gemtuzumab ozogamicin (Mylotarg®); anti-hormone products such as anastrozole, leuprolide, bicalutamide.

By "radiotherapy" is meant a method for locoregional treatment of tumours, using radiation to destroy the tumour cells by blocking their ability to multiply.

The expression "mammals, in particular humans, . . . being resistant to the conventional treatments" denotes mammals, in particular humans, having been resistant to conventional treatments from the start or having become resistant to the conventional treatments after being treated.

For example, the compounds of the invention can be used for:
- the prevention of resistance to chemotherapy in mammals, in particular humans, having never been treated with a chemotherapeutic agent,
- the treatment of resistance to chemotherapy in mammals, in particular humans, already resistant to a chemotherapeutic agent,
- the treatment of resistance to chemotherapy in mammals, in particular humans, already resistant to a chemotherapeutic agent by means of the combination of a product of the invention with a chemotherapy agent identical to or different from that to which the mammals, in particular the humans, are resistant.

The modulation or treatment of chemoresistance, in particular chemoresistance to paclitaxel, with the compounds of the invention, in particular compound 6, or a combination of a compound of the invention with a chemotherapy agent identical to or different from that to which the mammals, in particular the humans, are resistant, can be evaluated by the protocol of Example 14.

The presence of the three activities mentioned above therefore also confer upon the molecules of the invention the possibility of targeting mammals, in particular humans, resistant to conventional treatments.

In an advantageous embodiment, the present invention also relates to the use of at least one compound of formula (I), as a tubulin polymerization inhibitor and/or vascular-disrupting agent and antiproliferative agent, for preparing a drug intended for the prevention and treatment in the case of mammals, in particular humans, suffering from pathological angiogenesis, in particular retinopathies, or benign or malignant (cancerous) tumours, said mammals, in particular humans, suffering from benign or malignant tumours, being resistant to the conventional treatments or not being capable of developing resistance after treatment with said drug.

In an advantageous embodiment, the present invention also relates to the use of at least one compound of formula (I), as a tubulin polymerization inhibitor, vascular-disrupting agent and antiproliferative agent, for preparing a drug intended for the prevention and treatment in the case of mammals, in particular humans, suffering from pathological angiogenesis, in particular retinopathies, or benign or malignant (cancerous) tumours, said mammals, in particular humans, suffering from benign or malignant (cancerous) tumours being resistant to the conventional treatments or not being capable of developing resistance after treatment with said drug.

In an advantageous embodiment, the present invention also relates to the use of at least one compound of formula (I), as a protein phosphatase 1 inhibitor and/or vascular-disrupting agent and antiproliferative agent, for preparing a drug intended for the prevention and treatment in the case of mammals, in particular humans, suffering from pathological angiogenesis, in particular retinopathies, or benign or malignant (cancerous) tumours, said mammals, in particular humans, suffering from benign or malignant (cancerous) tumours being resistant to the conventional treatments or not being capable of developing resistance after treatment with said drug.

In an advantageous embodiment, the present invention also relates to the use of at least one compound of formula (I), as a protein phosphatase 1 inhibitor, vascular-disrupting agent and antiproliferative agent, for preparing a drug intended for the prevention and treatment in the case of mammals, in particular humans, suffering from pathological angiogenesis, in particular retinopathies, or benign or malignant (cancerous) tumours, said mammals, in particular humans, suffering from benign or malignant (cancerous) tumours being resistant to the conventional treatments or not being capable of developing resistance after treatment with said drug.

In an advantageous embodiment, the present invention also relates to the use of at least one compound of formula (I), as a protein phosphatase 1 and/or of tubulin polymerization inhibitor and antiproliferative agent, for preparing a drug intended for the prevention and treatment in the case of mammals, in particular humans, suffering from pathological angiogenesis, in particular retinopathies, or benign or malignant (cancerous) tumours, said mammals, in particular humans, suffering from benign or malignant (cancerous) tumours being resistant to the conventional treatments or not being capable of developing resistance after treatment with said drug.

In an advantageous embodiment, the present invention also relates to the use of at least one compound of formula (I), as a protein phosphatase 1 and tubulin polymerization inhibitor and antiproliferative agent, for preparing a drug intended for the prevention and treatment in the case of mammals, in particular humans, suffering from pathological angiogenesis, in particular retinopathies, or benign or malignant (cancerous) tumours said mammals, in particular humans, suffering from benign or malignant (cancerous) tumours being resistant to the conventional treatments or not being capable of developing resistance after treatment with said drug.

In an advantageous embodiment, the present invention also relates to the use of at least one compound of formula (I), as a protein phosphatase 1 and tubulin polymerization inhibitor and vascular-disrupting agent and antiproliferative agent, for preparing a drug intended for the prevention and treatment in the case of mammals, in particular humans, suffering from pathological angiogenesis, in particular retinopathies, or benign or malignant (cancerous) tumours, said mammals, in particular humans, suffering from benign or malignant (cancerous) tumours being resistant to the conventional treatments or not being capable of developing resistance after treatment with said drug.

In an advantageous embodiment, the present invention relates to one of the uses defined above, of at least one compound of general formula (I), for preparing a drug intended for the prevention and treatment in the case of mammals, in particular humans, suffering from pathological angiogenesis, in particular retinopathies, or benign or malignant (cancerous) tumours, irrespective of their size or their origin.

In an advantageous embodiment, the molecules defined above are used for preparing a drug intended for the prevention and/or treatment in the case of mammals, in particular humans, suffering from benign or malignant (cancerous) tumours chosen from the following: large-cell lung carcinoma, renal cell carcinoma, epithelial adenocarcinoma of the uterus, prostate carcinoma, glioblastoma, breast carcinoma, colorectal carcinoma and colorectal adenocarcinoma.

In an advantageous embodiment, the present invention relates to the use of at least one compound of formula (I) defined above, in which the R1 group of general formula (I) is chosen from H, $NO_2$ or pyrrole.

The compounds of this embodiment essentially possess a VDA activity and are PP1 inhibitors.

In an advantageous embodiment, the present invention relates to the use of at least one compound of formula (I) defined above, in which the R1 group of general formula (I) is as defined above, with the exclusion of $NO_2$ and/or R2 corresponds to a substituted phenyl.

The substituents are for example chosen from, but not limited to, an OH, $OPO_3H_2$, a $C_2$-$C_3$ alkyl, an O—($C_1$-$C_3$) alkyl.

The compounds of this embodiment possess a VDA activity, but little or no PP1 inhibiting activity and possess a tubulin-inhibiting activity.

By the expression "little or no PP1 inhibiting activity, is meant an IC50≥50 μM as measured by the method described in Example 9.

In an advantageous embodiment, the present invention relates to the use of at least one compound of formula (I) defined above, in which the R2 group of general formula (I) represents in particular a substituted phenyl.

The substituents are for example chosen from, but not limited to, a $C_2$-$C_4$ alkynyl group substituted by a trimethylsilyl, a tert-butyl, a hydroxy-2-propyl or an isopropyl.

The compounds of this embodiment essentially possess a VDA activity, but little or no PP1 inhibiting activity and possess little or no tubulin-inhibiting activity.

By the expression "little or no tubulin-inhibiting activity", is meant an inhibition percentage of less than 5%, as determined by the test of Example 6.

In an advantageous embodiment, the present invention relates to the use of at least one compound of formula (I) defined above, as a tubulin polymerization inhibitor, vascular-disrupting agent and antiproliferative agent, or as a protein phosphatase 1 and tubulin polymerization inhibitor, vascular-disrupting agent and antiproliferative agent, in which the R2 group of general formula (I) represents a phenyl substituted in the para position by a group chosen from ORe, Re being as defined above, a halogen, a $C_2$-$C_4$ alkyne group, substituted or not, in particular by a trimethylsilyl, a tert-butyl, a hydroxy-2-propyl or an isopropyl.

The compounds of this embodiment essentially possess a VDA activity and possess a tubulin-inhibiting activity.

In an advantageous embodiment, the present invention relates to the use of at least one compound of formula (I) defined above, as a vascular-disrupting agent, or
as a protein phosphatase 1 inhibitor and vascular-disrupting agent and antiproliferative agent, or
as a tubulin polymerization inhibitor, vascular-disrupting agent and antiproliferative agent,
in which the R1 group of general formula (I) is chosen from H, $NO_2$ or pyrrole and the R2 group of general formula (I) represents a phenyl substituted by a group of high steric hindrance.

The compounds of this embodiment belong to two categories of compounds:
those essentially possessing a VDA activity, which are PP1 inhibitors and or not possessing a tubulin-inhibiting activity, and those essentially possessing a VDA activity, having little or no PP1-inhibiting activity and possessing little or no tubulin-inhibiting activity.

In an advantageous embodiment, the present invention relates to the use of at least one compound of formula (I) defined above,
as a vascular-disrupting agent, or
as a protein phosphatase 1 inhibitor and vascular-disrupting agent and antiproliferative agent, or
as a tubulin polymerization inhibitor, vascular-disrupting agent and antiproliferative agent, or
as a protein phosphatase 1 and tubulin polymerization inhibitor, vascular-disrupting agent and antiproliferative agent,
in which the R1 group of general formula (I) is chosen from H, $NO_2$ or pyrrole and the R2 group of general formula (I) represents a phenyl substituted in the para position by a group chosen from ORe, Re being as defined above, a halogen, a $C_2$-$C_4$ alkyne group, substituted or not, in particular by a trimethylsilyl, a tert-butyl, a hydroxy-2-propyl or an isopropyl.

The compounds of this embodiment belong to two categories of compounds:
those essentially possessing a VDA activity, which are PP1 inhibitors, and possessing or not possessing a tubulin-inhibiting activity, and
those essentially possessing a VDA activity, which are not PP1 inhibitors and possessing a tubulin-inhibiting activity.

In an advantageous embodiment, the present invention relates to the use of at least one compound of formula (I) defined above,
as a vascular-disrupting agent, or
as a protein phosphatase 1 inhibitor and vascular-disrupting agent and antiproliferative agent, or
as a tubulin polymerization inhibitor, vascular-disrupting agent and antiproliferative agent, or
as a protein phosphatase 1 and tubulin polymerization inhibitor, vascular-disrupting agent and antiproliferative agent,
in which the R3 group of general formula (I) represents H.

In this embodiment, the compound of the invention is more particularly used for preparing a drug intended for the prevention and treatment in the case of mammals, in particular humans, suffering from pathological angiogenesis, in particular retinopathies.

In an advantageous embodiment, the present invention relates to the use of at least one compound of formula (I) defined above,
as a vascular-disrupting agent, or
as a protein phosphatase 1 inhibitor and vascular-disrupting agent and antiproliferative agent, or
as a tubulin polymerization inhibitor, vascular-disrupting agent and antiproliferative agent, or as a protein phosphatase 1 and tubulin polymerization inhibitor, vascular-disrupting agent and antiproliferative agent,
in which the R3 group of general formula (I) is as defined above with the exclusion of H.

In an advantageous embodiment, the present invention relates to the use of at least one compound of general formula (I) defined above, corresponding to a compound of general formula (IIa) below:

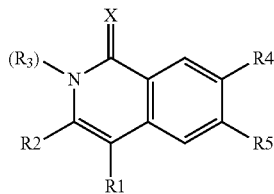
(IIa)

in which:
1) X represents:
   O, S, NH, N—$(C_1$-$C_6)$alkyl,
2) R1 represents:
   H, a halogen, OH, $OPO_3H_2$, OPO—(O—$(C_1$-$C_2)$ alkyl$)_2$, the alkyl being optionally substituted by one or more fluorines,
   $CF_3$, $CH_2OR'$, R' representing H or $(C_1$-$C_6)$alkyl, the alkyl being optionally substituted by one or more fluorines, CHO,
   $CO_2R''$, R'' representing H, $(C_1$-$C_6)$alkyl, the alkyl being optionally substituted by one or more fluorines,
   $CONR_cR_d$, $CH_2SO_2NR_cR_d$, $CH_2NHSO_2Rc$, $R_c$ and $R_d$ representing independently of each other: H, a $C_1$-$C_6$ alkyl, and $NR_cR_d$ represents an amino acid bound by its amine function, in particular a serine or a threonine, a $C_3$-$C_6$ cycloalkyl, or $R_c$ and $R_d$ represent together a $C_2$-$C_6$ alkyl,
   $NO_2$, $N_3$, ≡, CN, C(=N)$NH_2$, $SO_3H$, $SO_2NH_2$, $SO_2NHCH_3$, $NHSO_2CH_3$, $CH_2SO_2NR_cR_d$, $CH_2NHSO_2Rc$, $SO_2$—$NRaRb$, $SO_2$-imidazole, $NR_aR_b$, where:
   $R_a$ and $R_b$ represent independently of each other: H, a $C_1$-$C_6$ alkyl, a $C_3$-$C_6$ cycloalkyl, or
   Ra is H, a $C_1$-$C_6$ alkyl, a $C_3$-$C_6$ cycloalkyl, and Rb=$COR_f$, $COOR_f$ or $CONR_fR_f$ and $R_f$ representing H, a $C_1$-$C_6$ alkyl, a $C_3$-$C_6$ cycloalkyl or an amino acid chain (such as $CH(CH_2OH)NH_2$ for serine); $R_a$ and $R_b$ represent together a $C_2$-$C_6$ alkyl,
   $R_a$ and $R_b$ can form a $C_5$ to $C_7$ ring, in particular a pyrrolidine, a piperazine, a morpholine, a thiomorpholine,
   a heteroaryl, substituted or not, in particular a pyridine, an imidazole, an oxazole, a triazole, a pyrrole, a tetrazole.
3) R2 represents:
a phenyl substituted or not by one to three substituents chosen from:
a halogen, an OH, NHRa,
ORe, Re representing a benzyl, a methylene triazole, substituted or not, in particular by a $C_1$-$C_6$ alkyl.
$OPO_3H_2$, OPO—(O—$(C_1$-$C_2)$alkyl$)_2$, the alkyl being optionally substituted by one or more fluorines, an $NH_2$,
an NH—CORc group in which Rc represents H, a $C_1$-$C_6$ alkyl, a $C_3$-$C_6$ cycloalkyl or an amino acid chain (such as $CH(CH_2OH)NH_2$ for serine),
an O—$(C_1$-$C_6)$alkyl, in particular $OCH_3$, the alkyl being optionally substituted by one or more fluorines,
an O—COR1 where R1 represents O—$(C_1$-$C_6)$alkyl, or NRiRii, Ri and Rii being able to be $C_1$-$C_6$ alkyl,
a $C_2$-$C_4$ alkyl group, the alkyl group being optionally substituted by one or more fluorines, a $C_2$-$C_4$ alkenyl group, substituted or not,
a $C_2$-$C_4$ alkynyl group, substituted or not, in particular by a trimethylsilyl, a tert-butyl, a hydroxy-2-propyl or an isopropyl,
a heteroaryl, substituted or not, in particular a pyridine, an imidazole, an oxazole, a triazole, a pyrrole, a benzofuran, a thiophene, a benzothiophene, an indole,
a cyclohexyl, a piperazine, a morpholine, a thiomorpholine, a piperidine,
a 4-($NH_2$—$CH_2$—$CH_2O$)p)Ph group in which p is an integer from 1 to 6
4) R3 represents:
H, $(C_1$-$C_6)$alkyl, the alkyl being optionally substituted by one or more fluorines, $(C_3$-$C_6)$cycloalkyl, OH, $OPO_3H_2$, OPO—(O—$(C_1$-$C_2)$alkyl$)_2$, $OSO_3H$, $SO_3H$, O—$(C_1$ to $C_6)$alkyl, $NH_2$, NH—$(C_1$-$C_6)$alkyl, N—[$(C_1$-$C_6)$ alkyl]$_2$, NH—$(C_3$-$C_6)$cycloalkyl, N—[$(C_3$-$C_6)$cycloalkyl]$_2$, a propargyl group, $CH_2CN$, $(CH_2)_pOH$, p varying from 1 to 6, $CH_2OPO_3H_2$, $CH_2OPO$—(O—$(C_1$-$C_2)$alkyl$)_2$, $CH_2CH_2F$, $CH_2CHF_2$, $CH_2CF_3$,
5) R4 and R5 represent independently of each other:
H, OH, $OPO_3H_2$, OPO—(O—$(C_1$-$C_2)$alkyl$)_2$, the alkyl being optionally substituted by one or more fluorines, an O—$(C_1$-$C_6)$alkyl, in particular $OCH_3$, the alkyl being optionally substituted by one or more fluorines, a $C_1$-$C_6$ alkyl, the alkyl being optionally substituted by one or more fluorines, a $C_3$-$C_6$ cycloalkyl, a halogen,
R4 and R5 represent together a $(C_1$-$C_2)$ alkenyl dioxy optionally substituted by one or more fluorines, In an advantageous embodiment, the present invention relates to the use of at least one compound of general formula (I) defined above, corresponding to a compound of general formula (IIb) below:

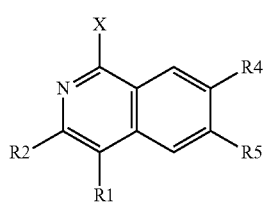
(IIb)

in which:
1) X represents:
   OH, $OPO_3H_2$, OPO—(O—$(C_1$-$C_2)$alkyl$)_2$, the alkyl being optionally substituted by one or more fluorines, O—$(C_1$-$C_6)$alkyl, in particular $OCH_3$, the alkyl being optionally substituted by one or more fluorines, O($C_3$-$C_6)$cycloalkyl, $NH_2$, $NH_4C_1$-$C_6)$alkyl, N—[$(C_1$-$C_6)$ alkyl]$_2$, NH—$(C_3$-$C_6)$cycloalkyl, N—[$(C_3$-$C_6)$cycloalkyl]$_2$, SH, S—$(C_1$-$C_6)$alkyl, the alkyl being optionally substituted by one or more fluorines, in particular $SCH_3$, S($C_3$-$C_6)$cycloalkyl, $SO_3H$, NH—$CH_2$-aryl or heteroaryl,
   OPh, SPh, $OCH_2Ph$, $SCH_2Ph$, the phenyl of these four groups being able to be substituted or not by one or more ($C_1$-$C_6$)alkyls, the alkyl being optionally substituted by one or more fluorines, $$OCH_2-\!\!\!=\!\!\!=\!\!\!=, \quad OCH_2-\!\!\!=\!\!\!=\!\!\!=N \qquad 5$$

2) R1 represents:
H, a halogen, OH, $OPO_3H_2$, OPO—(O—($C_1$-$C_2$)alkyl)$_2$, the alkyl being optionally substituted by one or more fluorines,
$CF_3$, $CH_2OR'$, R' representing H or ($C_1$-$C_6$)alkyl, the alkyl being optionally substituted by one or more fluorines, CHO,
$CO_2R''$, R'' representing H, ($C_1$-$C_6$)alkyl, the alkyl being optionally substituted by one or more fluorines,
$CONR_cR_d$, $CH_2SO_2NR_cR_d$, $CH_2NHSO_2Rc$, $R_c$ and $R_d$ representing independently of each other: H, a $C_1$-$C_6$ alkyl, and $NR_cR_d$ represents an amino acid bound by its amine function, in particular a serine or a threonine, a $C_3$-$C_6$ cycloalkyl, or $R_c$ and $R_d$ represent together a $C_2$-$C_6$ alkyl,
$NO_2$, $N_3$, ≡, CN, C(=N)$NH_2$, $SO_3H$, $SO_2NH_2$, $SO_2NHCH_3$, $NHSO_2CH_3$, $CH_2SO_2NR_cR_d$, $CH_2NHSO_2Rc$, $SO_2$—NRaRb, $SO_2$-imidazole, $NR_aR_b$, where:
$R_a$ and $R_b$ represent independently of each other: H, a $C_1$-$C_6$ alkyl, a $C_3$-$C_6$ cycloalkyl, or
Ra is H, a $C_1$-$C_6$ alkyl, a $C_3$-$C_6$ cycloalkyl, and Rb=$COR_f$, $COOR_f$ or $CONR_fR_f$ and $R_f$ representing H, a $C_1$-$C_6$ alkyl, a $C_3$-$C_6$ cycloalkyl or an amino acid chain (such as CH($CH_2OH$)$NH_2$ for serine), $R_a$ and $R_b$ represent together a $C_2$-$C_6$ alkyl,
$R_a$ and $R_b$ can form a C5 to C7 ring, in particular a pyrrolidine, a piperazine, a morpholine, a thiomorpholine,
a heteroaryl, substituted or not, in particular a pyridine, an imidazole, an oxazole, a triazole, a pyrrole, a tetrazole.

3) R2 represents:
a phenyl substituted or not by one to three substituents chosen from:
a halogen, an OH, NHRa,
ORe, Re representing a benzyl, a methylene triazole, substituted or not, in particular by a $C_1$-$C_6$ alkyl,
$OPO_3H_2$, OPO—(O—($C_1$-$C_2$)alkyl)$_2$, the alkyl being optionally substituted by one or more fluorines, an $NH_2$,
an NH—CORc group in which Rc represents H, a $C_1$-$C_6$ alkyl, a $C_3$-$C_6$ cycloalkyl or an amino acid chain (such as CH($CH_2OH$)$NH_2$ for serine),
an O—($C_1$-$C_6$)alkyl, in particular $OCH_3$, the alkyl being optionally substituted by one or more fluorines,
an O—COR1 where R1 represents O—($C_1$-$C_6$)alkyl, or NRiRii, Ri and Rii being able to be $C_1$-$C_6$ alkyl,
a $C_2$-$C_4$ alkyl group, the alkyl group being optionally substituted by one or more fluorines, a $C_2$-$C_4$ alkenyl group, substituted or not,
a $C_2$-$C_4$ alkynyl group, substituted or not, in particular by a trimethylsilyl, a tert-butyl, a hydroxy-2-propyl or an isopropyl
a heteroaryl, substituted or not, in particular a pyridine, an imidazole, an oxazole, a triazole, a pyrrole, a benzofuran, a thiophene, a benzothiophene, an indole,
a cyclohexyl, a piperazine, a morpholine, a thiomorpholine, a piperidine,
a 4-($NH_2$—($CH_2$—$CH_2O$)p)Ph group in which p is an integer from 1 to 6

4) R3 represents:
H, ($C_1$-$C_6$)alkyl, the alkyl being optionally substituted by one or more fluorines, ($C_3$-$C_6$)cycloalkyl, OH, $OPO_3H_2$, OPO—(O—($C_1$-$C_2$)alkyl)$_2$, $OSO_3H$, $SO_3H$, O—($C_1$ to $C_6$)alkyl, $NH_2$, NH—($C_1$-$C_6$)alkyl, N—[($C_1$-$C_6$)alkyl]$_2$, NH—($C_3$-$C_6$)cycloalkyl, N—[($C_3$-$C_6$)cycloalkyl]$_2$, a propargyl group, $CH_2CN$, ($CH_2$)$_p$OH, p varying from 1 to 6, $CH_2OPO_3H_2$, $CH_2OPO$—(O—($C_1$-$C_2$)alkyl)$_2$, $CH_2CH_2F$, $CH_2CHF_2$, $CH_2CF_3$, 5) R4 and R5 represent independently of each other:
H, OH, $OPO_3H_2$, OPO—(O—($C_1$-$C_2$)alkyl)$_2$, the alkyl being optionally substituted by one or more fluorines, an O—($C_1$-$C_6$)alkyl, in particular $OCH_3$, the alkyl being optionally substituted by one or more fluorines, a $C_1$-$C_6$ alkyl, the alkyl being optionally substituted by one or more fluorines, a $C_3$-$C_6$ cycloalkyl, a halogen, R4 and R5 represent together a ($C_1$-$C_2$) alkenyl dioxy optionally substituted by one or more fluorines.

In an advantageous embodiment, the present invention relates to the use of at least one compound of formula (IIa) defined above, chosen from the following:

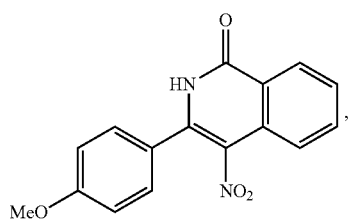
7
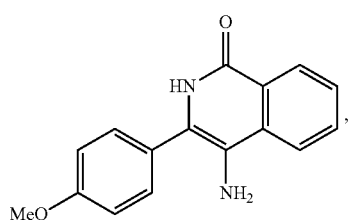
8
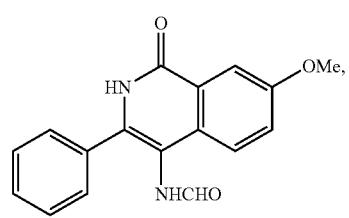
9
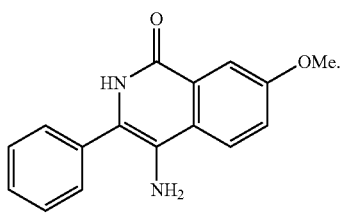
10
In another advantageous embodiment, the present invention relates to the use of at least one compound of formula (IIa) defined above, chosen from the following:
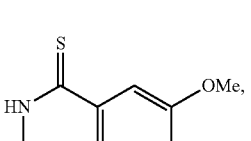
12
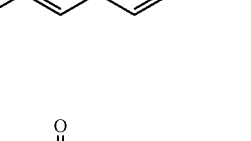
14
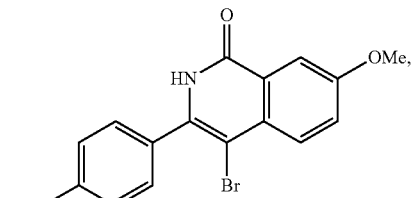
15
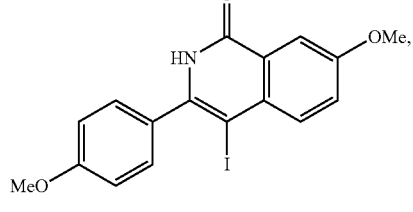
16
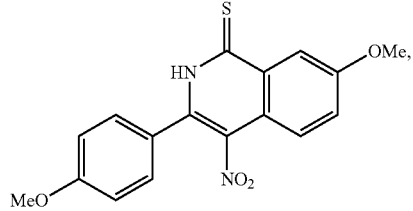
18
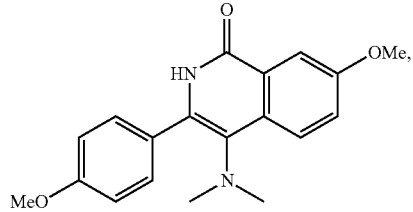
23
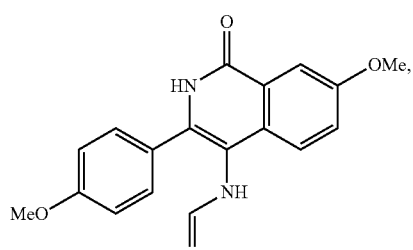
24
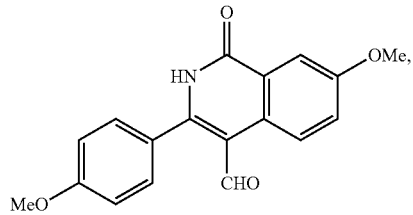
25
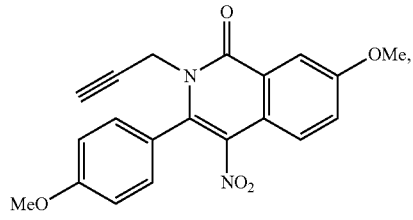
28

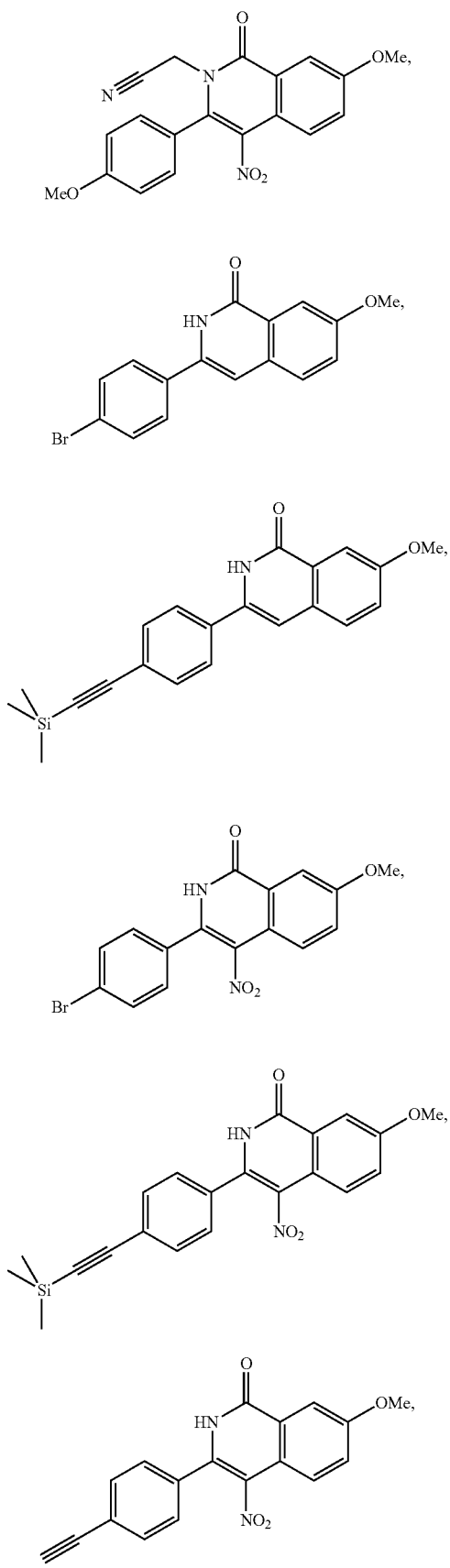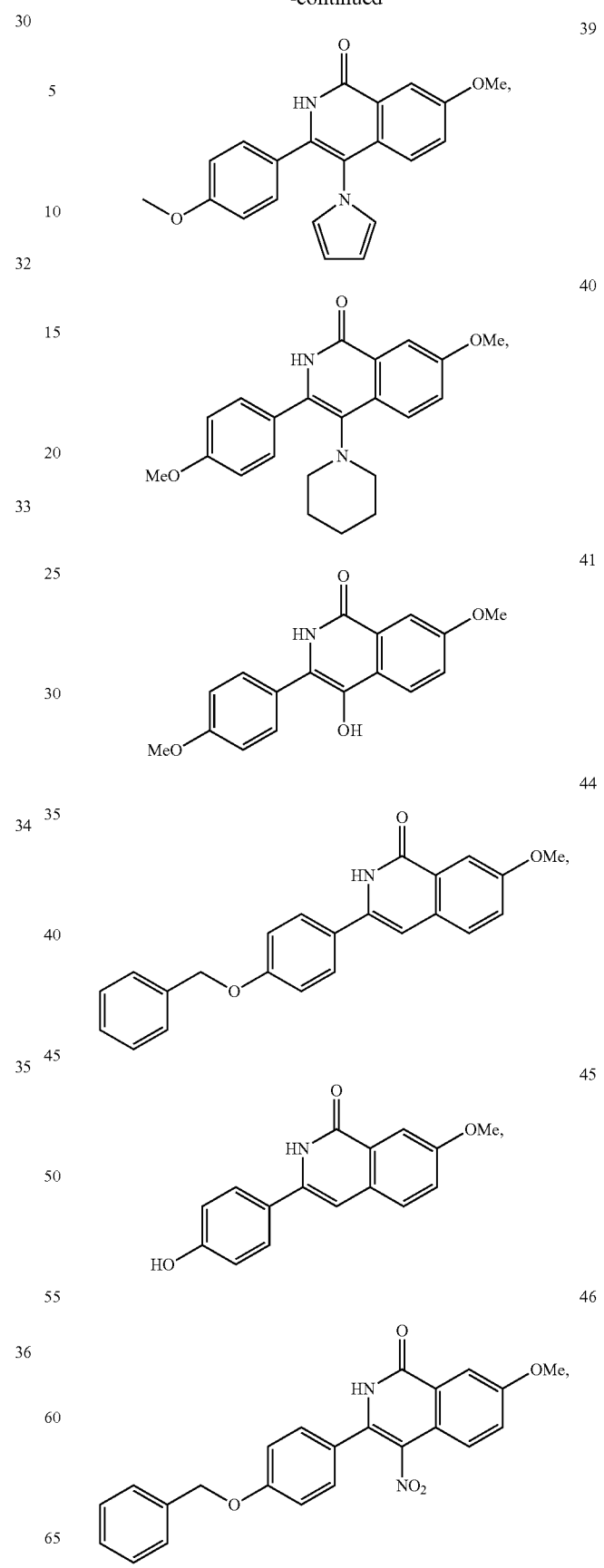

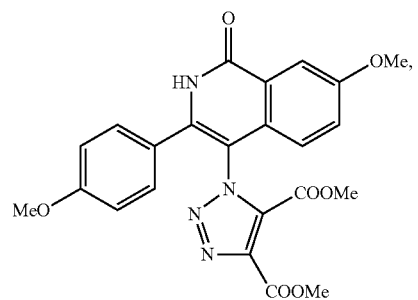
48
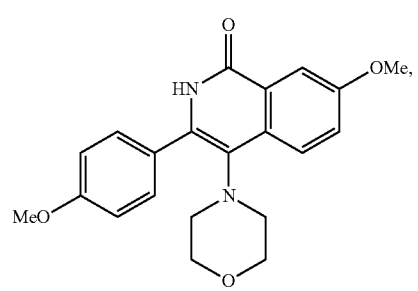
49
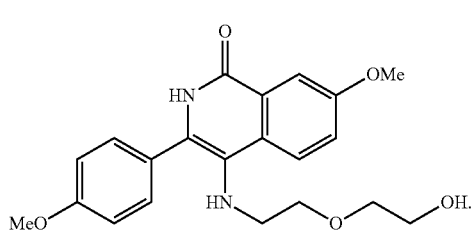
50
Compounds 12, 14-16, 18, 23-25, 28, 30, 32-36, 39-41, 44-46, 48-50 are novel compounds.
In another advantageous embodiment, the present invention relates to the use of at least compound of formula (IIb) defined above, chosen from the following:
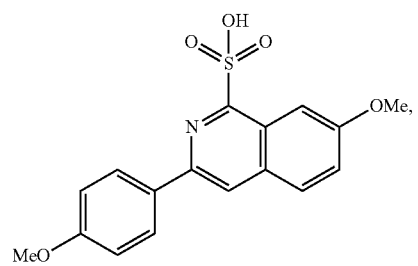
13
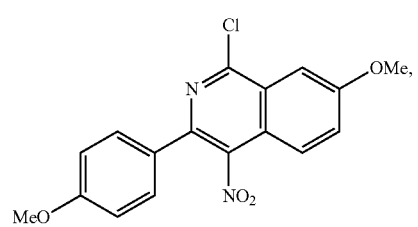
17
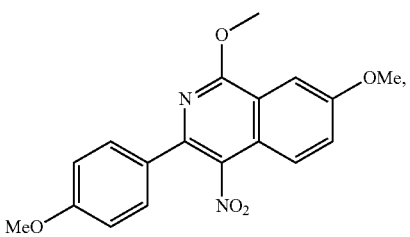
19
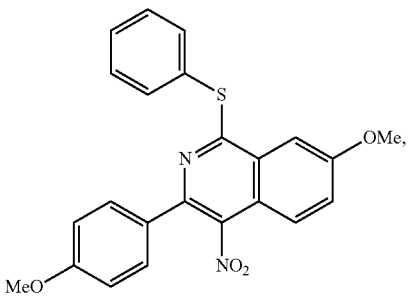
20
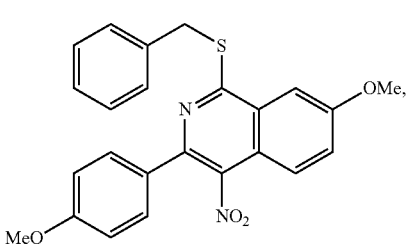
21
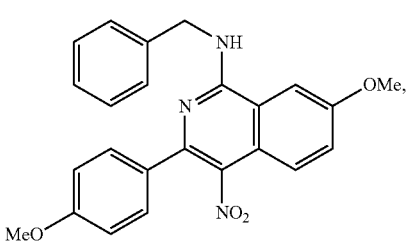
22
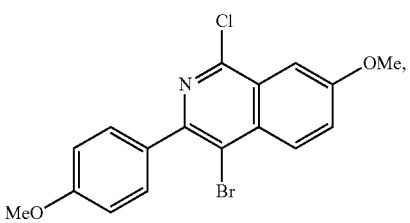
26
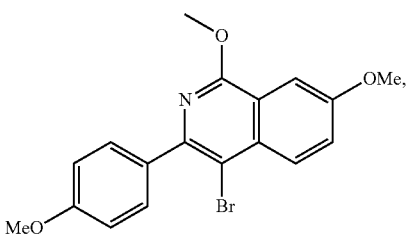
27

27
-continued
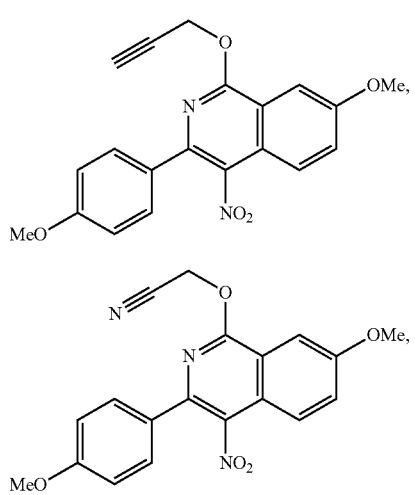
29
31
28
-continued
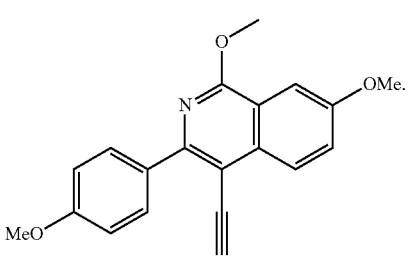
38
Compounds 13, 17, 19-22, 26-27, 29, 31 and 38 are novel compounds.
In an advantageous embodiment, the present invention relates to the use of at least one compound of formula (I) defined above, as a vascular-disrupting agent, in which the compounds of formula (I) are chosen from the following:
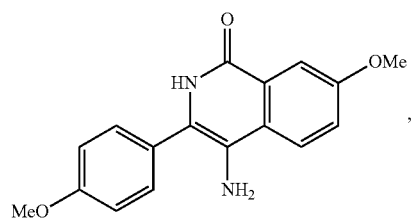
1
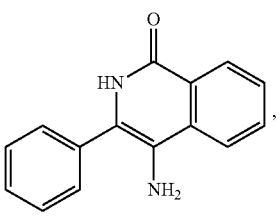
2
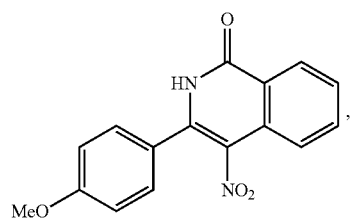
7
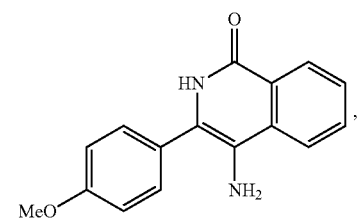
8
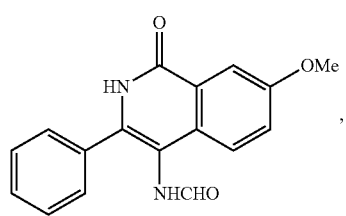
9
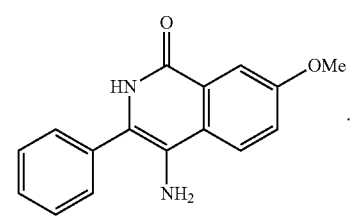
10
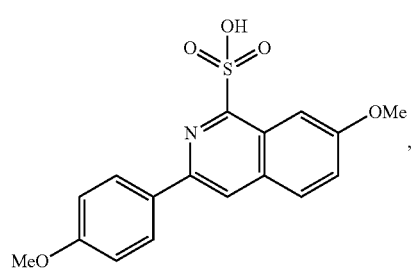
13
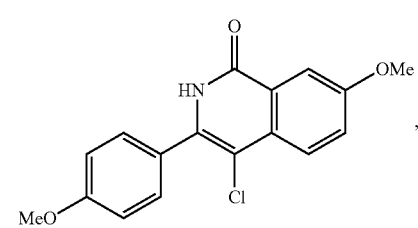
14

-continued
15
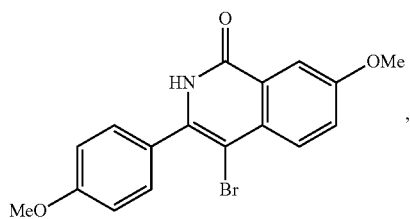
16
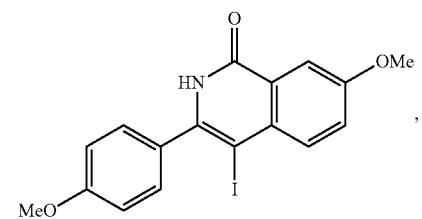
17
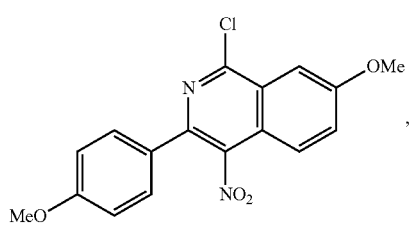
23
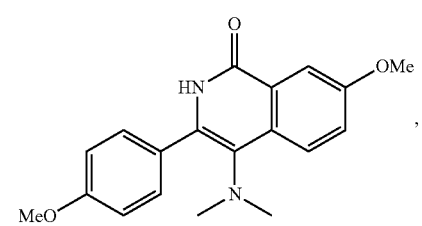
24
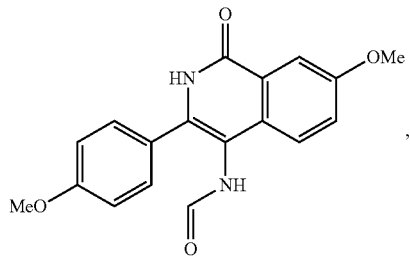
26
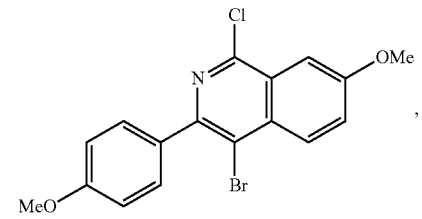
27
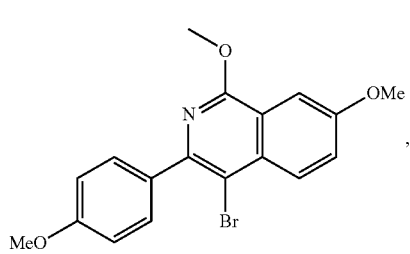
29
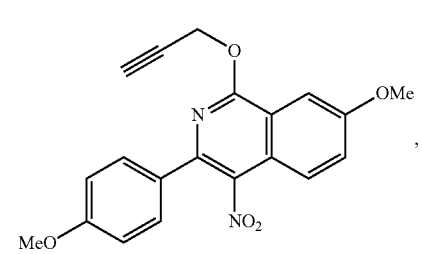
31
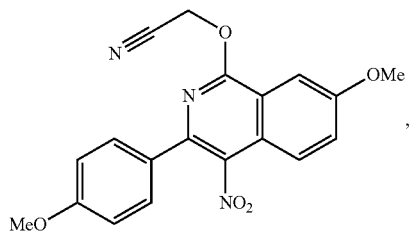
33
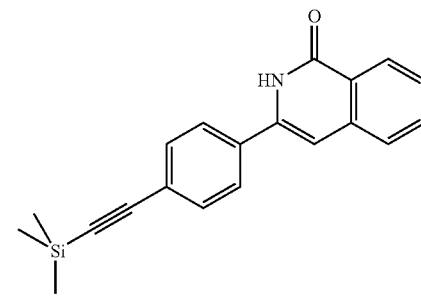
37
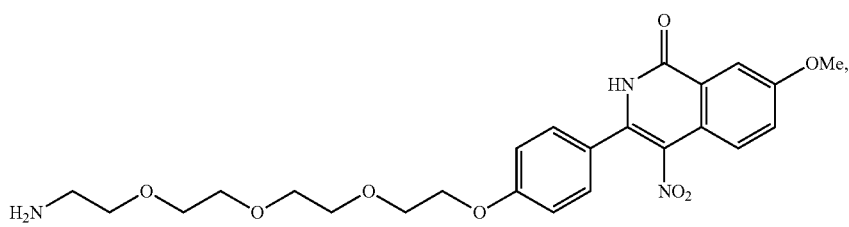

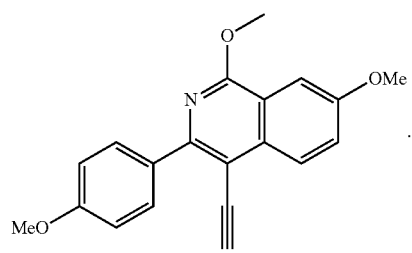

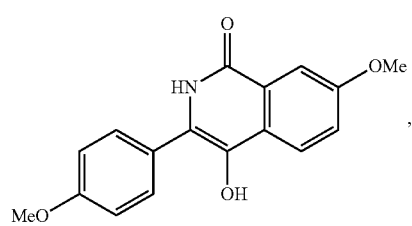

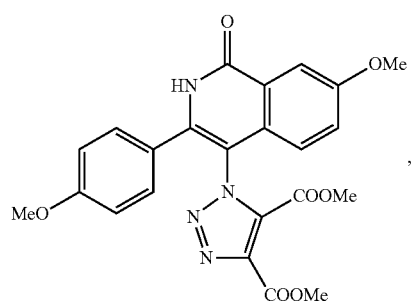

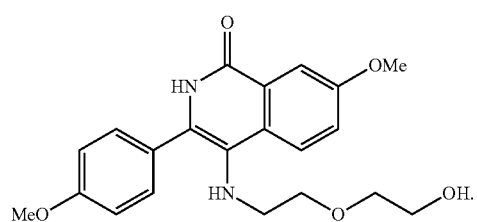

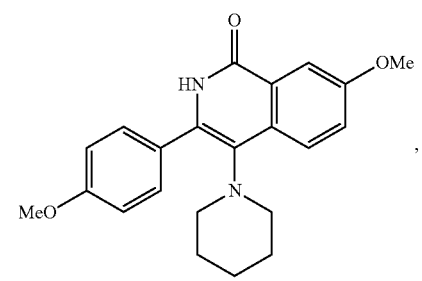

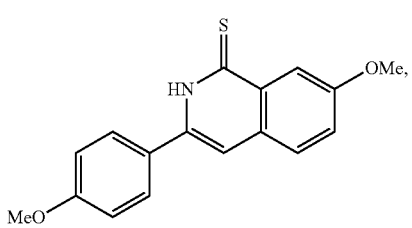

The compounds of this embodiment possess essentially a VDA activity and are not PP1 inhibitors.

In an advantageous embodiment, the present invention relates to the use of at least one compound of formula (I) defined above, as a protein phosphatase 1 inhibitor, vascular-disrupting agent and antiproliferative agent, in which the compounds of formula (I) are chosen from the following:

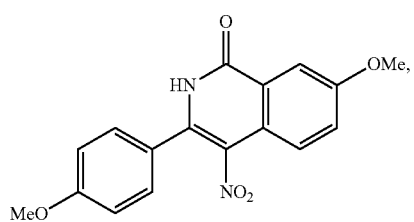

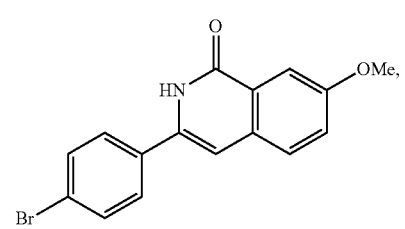

35

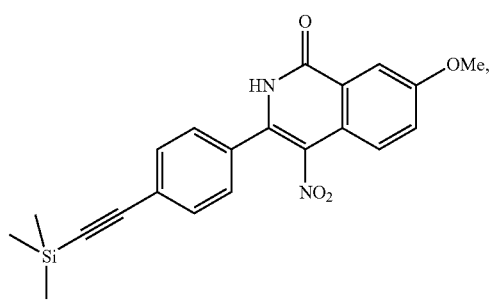

39

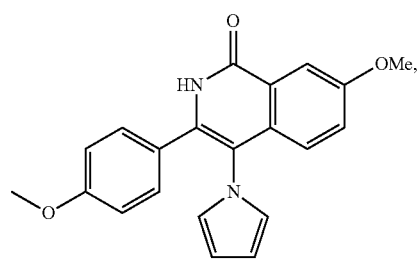

44

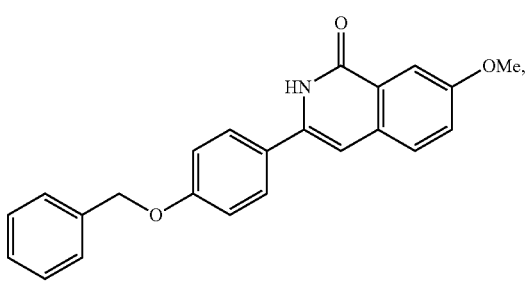

The compounds of this embodiment possess a VDA activity and are PP1 inhibitors but possess little or no tubulin-inhibiting activity.

In an advantageous embodiment, the present invention relates to the use of at least one compound of formula (I) defined above, as a protein phosphatase 1 inhibitor, vascular-disrupting agent, tubulin polymerization inhibitor, and antiproliferative agent, in which the compounds of formula (I) are chosen from the following:

18

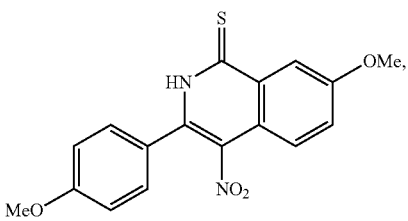

25

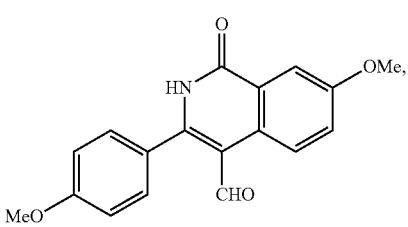

34

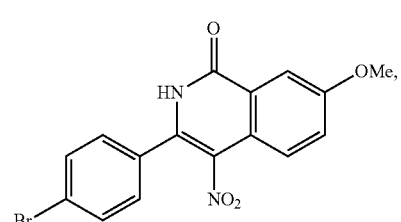

36

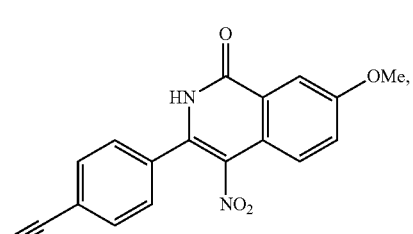

In an advantageous embodiment, the present invention relates to the use of at least one compound of formula (I) defined above, as a vascular-disrupting agent and antiproliferative agent, in which the compounds of formula (I) are chosen from the following:

1

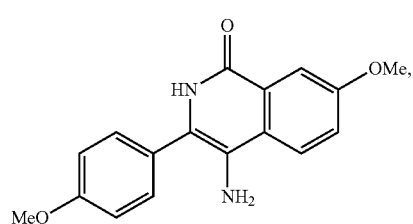

7

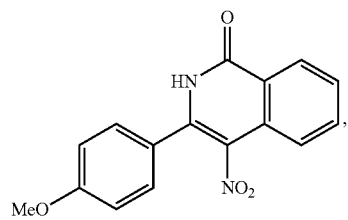

2

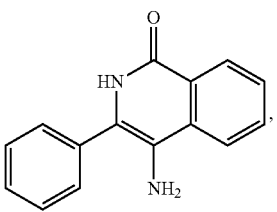

9

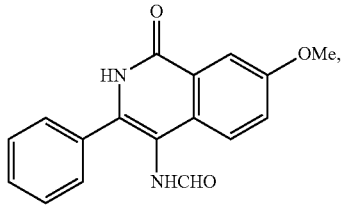

-continued
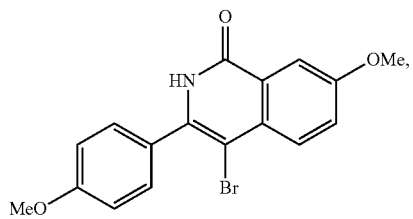
15
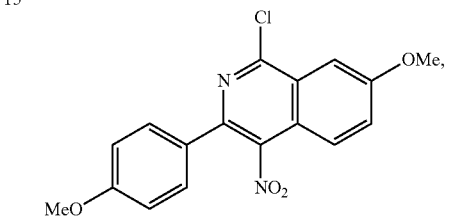
17
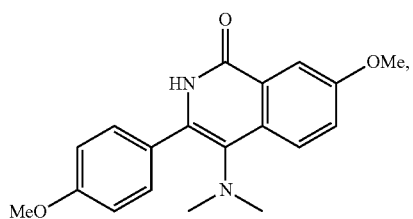
23
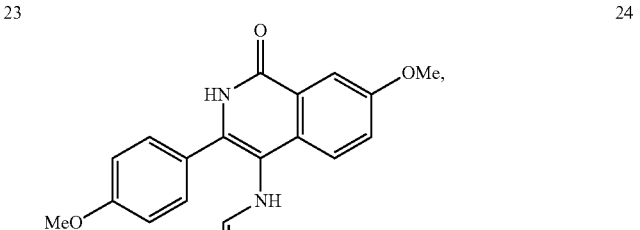
24
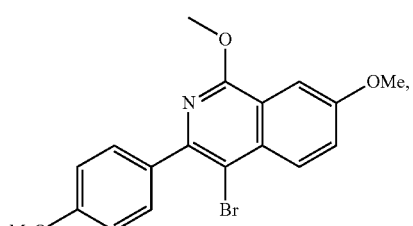
27
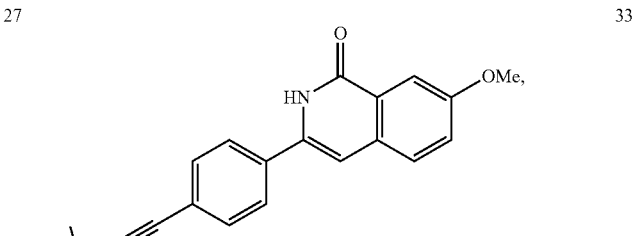
33
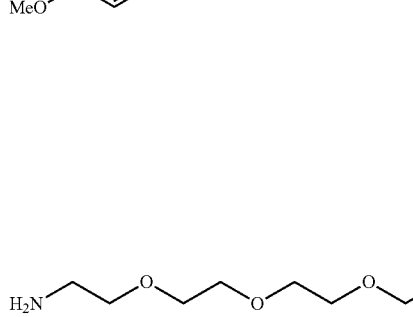
41
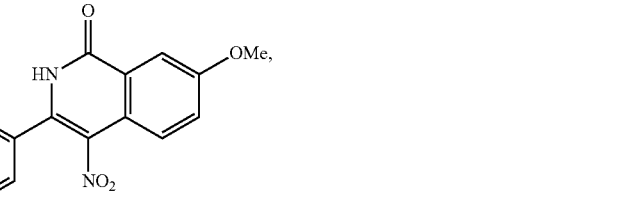
37
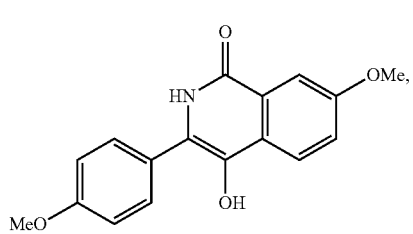
45
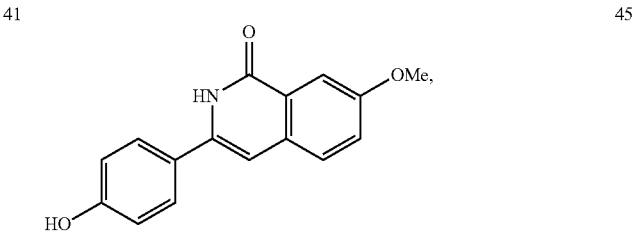
48
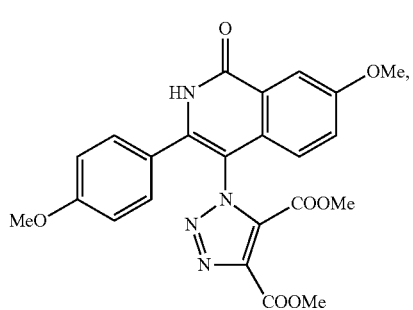
49
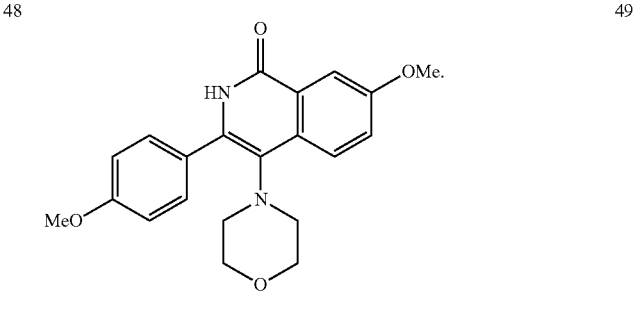
The compounds of this embodiment possess a VDA activity, have little or no PP1 inhibiting activity and possess little or no tubulin-inhibiting activity.
In an advantageous embodiment, the present invention relates to the use of at least one compound of formula (I) defined above, as a vascular-disrupting agent, tubulin polymerization inhibitor and antiproliferative agent, in which the compounds of formula (I) are chosen from the following:

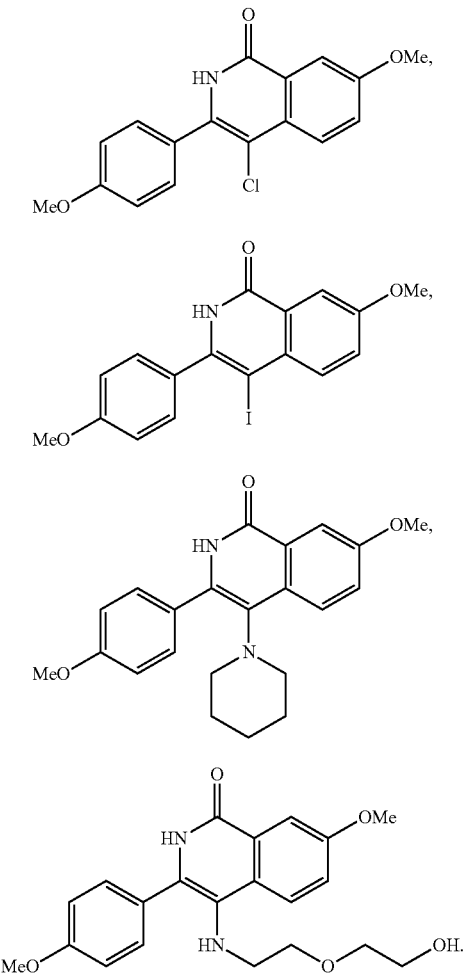

The compounds of this embodiment possess a VDA activity, have little or no PP1 inhibiting activity and possess a tubulin-inhibiting activity.

In an advantageous embodiment, the present invention relates to the use of at least one compound of formula (I) defined above, in which one of the R4 and R5 groups of the compounds of formula (I) are as defined above with the exception of a halogen.

In another advantageous embodiment, the present invention relates to the use of at least one compound of formula (I), (IIa) or (IIb) defined above, said compound of formula (I), or (IIa) or (IIb) provoking a necrosis in vivo in the centre of the tumour, which can be observed 24 hours or less after administration by oral or parenteral route of an active dose of said compound, such a necrosis is observed and measured on several histological tumour sections (from different depth levels) stained with haematoxylin-eosin.
(Salmon et al., Eur. J. Cancer, 2007, v43 (10): pp 1622-29).

The compounds of the invention cause asphyxia inside the tumour which is difficult to access and which is not usually destroyed by the products conventionally used, especially not by the anti-mitotic products, in particular because there are very few mitotic cells in the centre of tumours, since said mitotic cells are mostly found at the periphery of tumours The compounds of the invention also cause inflammation of the tissues around the necrotic areas which can thus lead to the destruction of the tumour masses not only by asphyxia but also by non-specific inflammation.

In another advantageous embodiment, the present invention relates to the use of at least one compound of formula (I), (IIa) or (IIb) defined above, said compound of formula (I), (IIa) or (IIb) possessing no anti-inflammatory properties.

The absence of anti-inflammatory properties of the compounds of the invention can be evaluated according to the protocol of Example 15.

As a result the products of the invention possess no anti-inflammatory properties unlike the compounds described in Patent Application WO 98/51307.

In another advantageous embodiment, the present invention relates to the use of at least one compound of formula (I), (IIa) or (IIb) defined above, said compound of formula (I), (IIa) or (IIb) being administered by oral route, at a dose comprised between approximately 1 mg/kg and approximately 200 mg/kg, preferentially from approximately 10 mg/kg to approximately 100 mg/kg, more preferentially from 20 mg/kg to 50 mg/kg, in particular 40 mg/kg.

In another advantageous embodiment, the present invention relates to the use of at least one compound of formula (I), (IIa) or (IIb) defined above, said compound of formula (I), (IIa) or (IIb) being administered by oral route, divided into one or more doses from approximately 3 mg/m$^2$ to approximately 600 mg/m$^2$, preferably from approximately 30 mg/m$^2$ to approximately 300 mg/m$^2$, more preferably from 60 mg/m$^2$ to 150 mg/m$^2$, in particular 120 mg/m$^2$.

In an advantageous embodiment, the dose of the compound of formula (I), (II) or (III), defined above, used for the treatment, can be approximately 1 mg/kg, approximately 2 mg/kg, approximately 5 mg/kg, approximately 7 mg/kg, approximately 10 mg/kg, approximately 20 mg/kg, or it can be approximately 30 mg/kg, approximately 40 mg/kg, approximately 50 mg/kg, approximately 60 mg/kg, approximately 80 mg/kg, or also approximately 100 mg/kg, approximately 120 mg/kg, approximately 140 mg/kg, approximately 150 mg/kg, approximately 160 mg/kg, approximately 180 mg/kg, approximately 200 mg/kg.

In an advantageous embodiment, the compound of formula (I), (II) or (III), defined above, used for the treatment, can be administered in one or more divided doses of approximately 3 mg/m$^2$, approximately 6 mg/m$^2$, approximately 15 mg/m$^2$, approximately 21 mg/m$^2$, approximately 30 mg/m$^2$, approximately 60 mg/m$^2$, or it can be approximately 90 mg/m$^2$, approximately 120 mg/m$^2$, approximately 150 mg/m$^2$, approximately 180 mg/m$^2$, approximately 240 mg/m$^2$, or also approximately 300 mg/m$^2$, approximately 360 mg/m$^2$, approximately 420 mg/m$^2$, approximately 450 mg/m$^2$, approximately 480 mg/m$^2$, approximately 540 mg/m$^2$, approximately 600 mg/m$^2$.

In an advantageous embodiment, the dose of the compound of formula (I), (IIa) or (IIb), defined above, used for the treatment, can be comprised between approximately 200 mg/kg and approximately 400 mg/kg, in particular from approximately 200 to approximately 300 mg/kg, and preferably approximately 200 mg/kg, approximately 210 mg/kg, approximately 220 mg/kg, approximately 230 mg/kg, approximately 240 mg/kg, approximately 250 mg/kg, approximately 260 mg/kg, approximately 270 mg/kg, approximately 280 mg/kg, approximately 290 mg/kg or approximately 300 mg/kg, as a function of the effective dose and/or maximum tolerated by mammals, in particular humans.

In an advantageous embodiment, the compound of formula (I), (IIa) or (IIb), defined above, used for the treatment, can be administered in one or more divided doses comprised between approximately 600 mg/m² and approximately 1200 mg/m², in particular from approximately 600 to approximately 900 mg/m², and preferably approximately 600 mg/m², approximately 630 mg/m², approximately 660 mg/m², approximately 690 mg/m², approximately 720 mg/m², approximately 750 mg/m², approximately 780 mg/m², approximately 810 mg/m², approximately 840 mg/m², approximately 870 mg/m² ou approximately 900 mg/m², as a function of the effective dose and/or maximum tolerated by mammals, in particular humans.

Moreover, as shown in the examples presenting the activity of the compounds of the invention and in particular compound 6, in vivo, or by FIG. 14 presenting evidence of the absence of major toxicity in vivo of the compounds of the invention and in particular of compound 6, in vivo, the compounds of the invention and in particular compound 6 exhibit an effect (FIG. 15) confirming de facto the bioavailability of the products of the invention and in particular of compound 6.

In an advantageous embodiment, the present invention relates to the use of at least one compound of formula (I), (IIa) or (IIb) defined above, said compound of formula (I), (IIa) or (IIb) being administrable by intravenous route at a dose comprised between approximately 0.1 mg/kg/d and approximately 100 mg/kg/d, in particular 50 mg/kg/d, in particular 10 mg/kg/d.

In another advantageous embodiment, said compound of formula (I), (IIa) or (IIb) defined above, is in combination with at least one antitumour drug chosen from the following, without being limited to: abraxane, abarelix, aldesleukin, alemtuzumab, alitretinoin, allopurinol, altretamine, anastrozole, arsenic trioxide, asparaginase, azacitidine, bevacizumab, bexarotene, bicalutamide, bleomycin, bortezomib, intravenous busulphan, oral busulphan, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, 5-fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, taxol, taxotere, temozolomide, teniposide, testolactone, thalidomide, thioguanine, thiotepa, topotecan, toremifene, tositumomab, trastuzumab, tretinoin, tykerb, uracil mustard, valrubicin, vinblastine, vincristine, vinorelbine, vorinostat, and zoledronate.

In most cases, for the treatment of benign or malignant tumours, it can be advantageous to combine the compounds of the invention with (a) conventional treatment(s) as defined above, so as to obtain the additional or synergistic effect between the compounds of the invention and the conventional treatment(s).

In another advantageous embodiment, said compound of formula (I), (IIa) or (IIb) defined above can be combined with an effective quantity of ionizing radiation.

The compound of the invention and the standard antitumour drug or the effective quantity of ionizing radiation can be administered concomitantly and/or non-concommitantly, i.e. sequentially.

In another advantageous embodiment, said compound of formula (I), (IIa) or (IIb) defined above, can be associated with surgery.

The compound of the invention can then be administered before, during or after the conventional treatment(s).

In another advantageous embodiment, said compound of formula (I), (IIa) or (IIb) defined above, is combined with at least one treatment against retinopathy such as, but not limited to, laser treatment or Avastin.

The activity of Avastin in retinopathy is in particular described in: Spaide R. F. and Fisher Y L, Retina. 2006, v26(3): pp 275-8.

According to another aspect, the invention relates to a pharmaceutical composition comprising as active ingredient a compound of formula (I), as defined above, in combination with a pharmaceutically acceptable vehicle, with the exclusion of the following compounds:

when X=O, n=1, R3=H, and the bond between carbon 1 and the X group is double and, R1=NH$_2$, R2=phenyl or 4-OH-phenyl, substituted or not, R4=H, OH, an O—(C$_1$-C$_6$)alkyl, a C$_1$-C$_6$ alkyl, a C$_3$-C$_6$ cycloalkyl, and R5=H, OH, an O—(C$_1$-C$_6$)alkyl, a C$_1$-C$_6$ alkyl, a C$_3$-C$_6$ cycloalkyl, and when X=O or S, n=1, R3=H, and when the bond between carbon 1 and the X group is double, R2 having the same meaning as above and one of R4 and R5 represents a halogen.

In this embodiment, general formula (I) and the dotted lines correspond to the three structures defined above, with the exclusion of the compounds of formula IV below:

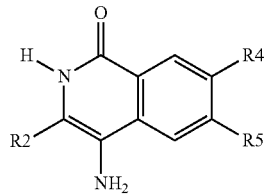

(IV)

in which R2=phenyl or 4-OH-phenyl, substituted or not, R4=H, OH, an O—(C$_1$-C$_6$)alkyl, a C$_1$-C$_6$ alkyl, a C$_3$-C$_6$ cycloalkyl, and R5=H, OH, an O—(C$_1$-C$_6$)alkyl, a C$_1$-C$_6$ alkyl, a C$_3$-C$_6$ cycloalkyl.

The pharmaceutically acceptable vehicles which can be used within the context of the pharmaceutical compositions of the invention are well known to a person skilled in the art.

In an advantageous embodiment, the pharmaceutical composition defined above comprises as active ingredient a compound of formula I, in which:

n=0, the bond between carbon 1 and the X group is single and X is chosen from SO3H, OCH3,

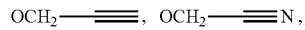

or n=1, the bond between carbon 1 and the X group is double, X=O or S and R2 represents a phenyl substituted in position 4 by a group chosen from OH, OCH3, O-benzyl, Br, a $C_2$-$C_4$ alkynyl group substituted or not, in particular by a trimethylsilyl, a tert-butyl, a hydroxy-2-propyl or an isopropyl.

In an advantageous embodiment, the invention relates to a pharmaceutical composition comprising as active ingredient a compound of formula I, as defined above, in which R1=H.

In an advantageous embodiment, the invention relates to a pharmaceutical composition comprising as active ingredient a compound of formula I, with the exclusion of the following compounds:

when X═O or S, n=1, R3═H, and when the bond between carbon 1 and the X group is double, R2, R4 and R5 having the same meaning as above, the compounds in which R1═H.

In an advantageous embodiment, the pharmaceutical composition defined above comprises as active ingredient a compound of formula (IIa), as defined above, in combination with a pharmaceutically acceptable vehicle, diluent or excipient.

In this embodiment, general formula (IIa and IIb)) and the dotted lines correspond to the two structures defined above, the same compounds as above being excluded from formulae (IIa and IIb).

In an advantageous embodiment, the pharmaceutical composition defined above comprises as active ingredient a compound of formula IIa, as defined above, in combination with a pharmaceutically acceptable vehicle, diluent or excipient.

In this embodiment, the same compounds as those excluded above are also excluded from formula (IIa).

In an advantageous embodiment, the pharmaceutical composition defined above comprises as active ingredient a compound of formula IIb, as defined above.

In an advantageous embodiment, the pharmaceutical composition defined above comprises as active ingredient a compound of formula IIa, chosen from compounds 1, 2, 4-10 defined above.

In an advantageous embodiment, the pharmaceutical composition defined above comprises as active ingredient a compound of formula IIa, chosen from compounds 1, 14-16, 18, 23-25, 28, 30, 32-36, 39-41, 44-46 and 48-50 defined above.

In an advantageous embodiment, the pharmaceutical composition defined above comprises as active ingredient a compound of formula IIb, chosen from compounds 13, 17, 19-22, 26-27, 29, 31 and 38 defined above.

In an advantageous embodiment, the pharmaceutical composition defined above comprises as active ingredient a compound chosen from compounds 1, 2, 7, 8, 9, 10, 13-17, 23-24, 26-27, 29, 31, 33, 37-38, 40-41, 45, and 48-50 defined above.

In an advantageous embodiment, the pharmaceutical composition defined above comprises as active ingredient a compound chosen from compounds 6, 12, 19, 20, 22, 28, 30, 32, 35, 39, 44, and 46 defined above.

In an advantageous embodiment, the pharmaceutical composition defined above comprises as active ingredient a compound chosen from compounds 18, 21, 25, 29, 34 and 36 defined above.

In an advantageous embodiment, the pharmaceutical composition defined above comprises as active ingredient a compound chosen from compounds 1, 2, 7, 8, 9, 10, 13, 15, 17, 23-24, 26-27, 29, 31, 33, 37-38, 41, 45 and 48-49 defined above.

In an advantageous embodiment, the pharmaceutical composition defined above comprises as active ingredient a compound chosen from compounds 14, 16, 24, 26-40 and 50 defined above.

In an advantageous embodiment, the pharmaceutical composition defined above comprises as active ingredient a pro-drug, as defined above, in which at least one of the X, R2, R4 and R5 groups represents a phosphate group: $OPO_3H_2$, alkyl phosphate: OPO—(O—$(C_1$-$C_2)$alkyl$)_2$, and/or the R3 group represents a $CH_2OPO_3H_2$ or $CH_2OPO$—(O—$(C_1$-$C_2)$alkyl$)_2$ group, and/or at least one of the R1 and R2 groups represents an amino acid bound by its acid function, in particular a serine.

In an advantageous embodiment, the pharmaceutical composition comprising a compound of formula (I), (IIa) or (IIb) defined above can be administered by oral route at a dose comprised of from approximately 1 mg/kg to approximately 200 mg/kg, preferably from approximately 10 mg/kg to approximately 100 mg/kg, more preferably from 20 mg/kg to 50 mg/kg, in particular 40 mg/kg.

In another advantageous embodiment, the pharmaceutical composition comprising a compound of formula (I), (IIa) or (IIb) defined above can be administered by oral route, divided into one or more doses from approximately 3 mg/m$^2$ to approximately 600 mg/m$^2$, preferably from approximately 30 mg/m$^2$ to approximately 300 mg/m$^2$, more preferably from 60 mg/m$^2$ to 150 mg/m$^2$, in particular 120 mg/m$^2$.

In another advantageous embodiment, the pharmaceutical composition comprising a compound of formula (I), (IIa) or (IIb) defined above can be administered by oral route, at a dose comprised of approximately 1 mg/kg, approximately 2 mg/kg, approximately 5 mg/kg, approximately 7 mg/kg, approximately 10 mg/kg, approximately 20 mg/kg, or it can be approximately 30 mg/kg, approximately 40 mg/kg, approximately 50 mg/kg, approximately 60 mg/kg, approximately 80 mg/kg, or also approximately 100 mg/kg, approximately 120 mg/kg, approximately 140 mg/kg, approximately 150 mg/kg, approximately 160 mg/kg, approximately 180 mg/kg, approximately 200 mg/kg.

In another advantageous embodiment, the pharmaceutical composition comprising a compound of formula (I), (IIa) or (IIb) defined above can be administered by oral route, divided into one or more doses of approximately 3 mg/m$^2$, approximately 6 mg/m$^2$, approximately 15 mg/m$^2$, approximately 21 mg/m$^2$, approximately 30 mg/m$^2$, approximately 60 mg/m$^2$, or it can be approximately 90 mg/m$^2$, approximately 120 mg/m$^2$, approximately 150 mg/m$^2$, approximately 180 mg/m$^2$, approximately 240 mg/m$^2$, or also approximately 300 mg/m$^2$, approximately 360 mg/m$^2$, approximately 420 mg/m$^2$, approximately 450 mg/m$^2$, approximately 480 mg/m$^2$, approximately 540 mg/m$^2$, approximately 600 mg/m$^2$.

In another advantageous embodiment, the pharmaceutical composition comprising a compound of formula (I), (IIa) or (IIb) defined above can be administered by oral route, divided into one or more doses from approximately 600 mg/m$^2$ to approximately 1200 mg/m$^2$, in particular from approximately 600 to approximately 900 mg/m$^2$, and preferably approximately 600 mg/m$^2$, approximately 630 mg/m$^2$, approximately 660 mg/m$^2$, approximately 690 mg/m$^2$, approximately 720 mg/m$^2$, approximately 750 mg/m$^2$, approximately 780 mg/m$^2$, approximately 810 mg/m$^2$, approximately 840 mg/m$^2$, approximately 870 mg/m$^2$ or approximately 900 mg/m$^2$, as a function of the maximum dose tolerated by mammals, in particular humans.

In another advantageous embodiment, the pharmaceutical composition comprising a compound of formula (I), (IIa) or (IIb) defined above can be administered by oral route, divided into one or more doses from approximately 3 mg/m$^2$ to approximately 600 mg/m$^2$, preferably from approximately 30 mg/m$^2$ to approximately 300 mg/m$^2$, more preferably from 60 mg/m$^2$ to 150 mg/m$^2$, in particular 120 mg/m$^2$ as a function of the maximum dose tolerated by mammals, in particular humans.

The use of a pharmaceutically acceptable vehicle such as beta cyclodextrin (β-CD) makes it possible to increase the solubility of the compounds of the invention, and as a result to administer the compounds of the invention by oral route. Beta cyclodextrin has the following structure:

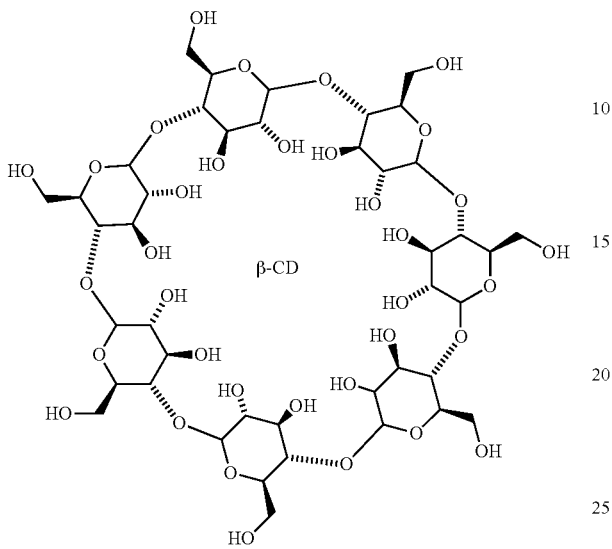

but alpha cyclodextrin or gamma cyclodextrin can also be used as a means of increasing the aqueous solubility of the product.

It is well understood that other pharmaceutically acceptable vehicles, diluents or excipients can be used, even those which do not improve solubility. Another example of a pharmaceutical vehicle which can be used with the products of the invention is albumin or another protein and/or another pharmaceutically acceptable non-protein macromolecule, loaded with the product of the invention in its native state or in the form of nanoparticles.

In an advantageous embodiment, the pharmaceutical composition comprising a compound of formula (I), (IIa) or (IIb) defined above, can be administered by for example, without being limited to: parenteral, intravenous route at a dose comprised of from approximately 0.1 mg/kg/d to approximately 100 mg/kg/d, in particular 0.1 mg/kg to 50 mg/kg/d, in particular 10 mg/kg/d.

According to another aspect, the invention relates to a compound as defined above, of general formula (I) below:

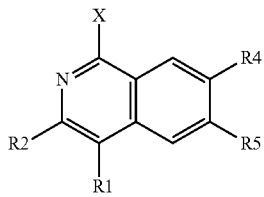

(I)

in which:
1) the bond between carbon 1 and the X group is single or double, the bond between nitrogen 2 and carbon 1 can be single or double
   it being understood that:
   a. when the bond between X and said carbon 1 is double, then the bond between nitrogen 2 and carbon 1 is single:
   and,
   b. when the bond between X and said carbon 1 is single, then the bond between nitrogen 2 and carbon 1 is double and formula I corresponds to an aromatic system of formula I-A below:

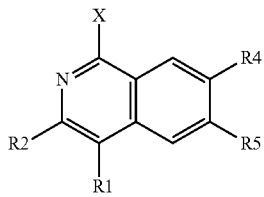

I-A 2) n represents 0 or 1,
3) X represents:
   a) when n=1:
      O, S, NH, N—($C_1$-$C_6$)alkyl,
   b) when n=0:
      OH, $OPO_3H_2$, OPO—(O—($C_1$-$C_2$)alkyl)$_2$, the alkyl being optionally substituted by one or more fluorines, O—($C_1$-$C_6$)alkyl, in particular $OCH_3$, the alkyl being optionally substituted by one or more fluorines, O($C_3$-$C_6$)cycloalkyl, $NH_2$, NH—($C_1$-$C_6$)alkyl, N—[($C_1$-$C_6$)alkyl]$_2$, NH—($C_3$-$C_6$)cycloalkyl, N—[($C_3$-$C_6$)cycloalkyl]$_2$, SH, S—($C_1$-$C_6$)alkyl, the alkyl being optionally substituted by one or more fluorines, in particular $SCH_3$, S($C_3$-$C_6$)cycloalkyl, $SO_3H$, NH—$CH_2$-aryl or heteroaryl,
      OPh, SPh, $OCH_2Ph$, $SCH_2Ph$, the phenyl of these four groups being able to be substituted or not by one or more ($C_1$-$C_6$)alkyls, the alkyl being optionally substituted by one or more fluorines,

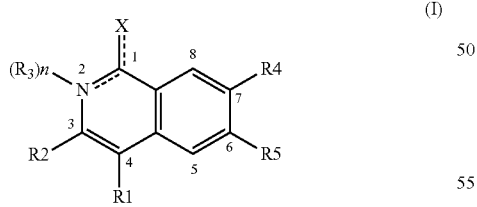

4) R1 represents:
   H, a halogen, OH, $OPO_3H_2$, OPO—(O—($C_1$-$C_2$)alkyl)$_2$, the alkyl being optionally substituted by one or more fluorines,
   $CF_3$, $CH_2OR'$, R' representing H or ($C_1$-$C_6$)alkyl, the alkyl being optionally substituted by one or more fluorines, CHO,
   $CO_2R''$, R'' representing H, ($C_1$-$C_6$)alkyl, the alkyl being optionally substituted by one or more fluorines,
   $CONR_cR_d$, $CH_2SO_2NR_cR_d$, $CH_2NHSO_2Rc$, $R_c$ and $R_d$ representing independently of each other: H, a $C_1$-$C_6$ alkyl, and $NR_cR_d$ represents an amino acid bound by its amine function, in particular a serine or a threonine, a $C_3$-$C_6$ cycloalkyl, or $R_c$ and $R_d$ represent together a $C_2$-$C_6$ alkyl,
   $NO_2$, $N_3$, ≡, CN, C(=N)$NH_2$, $SO_3H$, $SO_2NH_2$, $SO_2NHCH_3$, $NHSO_2CH_3$, $CH_2SO_2NR_cR_d$, $CH_2NHSO_2Rc$, $SO_2$—$NRaRb$, $SO_2$-imidazole,
   $NR_aR_b$, where:
      $R_a$ and $R_b$ represent independently of each other: H, a $C_1$-$C_6$ alkyl, a $C_3$-$C_6$ cycloalkyl, or
   Ra is H, a $C_1$-$C_6$ alkyl, a $C_3$-$C_6$ cycloalkyl, and Rb=$COR_f$, $COOR_f$ or $CONR_fR_fR_f$ and $R_f$ representing H, a $C_1$-$C_6$ alkyl, a $C_3$-$C_6$ cycloalkyl or an amino acid chain (such as $CH(CH_2OH)NH_2$ for serine), $R_a$ and $R_b$ represent together a $C_2$-$C_6$ alkyl,
   $R_a$ and $R_b$ can form a C5 to C7 ring, in particular a pyrrolidine, a piperazine, a morpholine, a thiomorpholine, a heteroaryl, substituted or not, in particular a pyridine, an imidazole, an oxazole, a triazole, a pyrrole, a tetrazole.

5) R2 represents:
a phenyl substituted or not by one to three substituents chosen from:
a halogen, an OH, NHRa,
ORe, Re representing a benzyl, a methylene triazole, substituted or not, in particular by a $C_1$-$C_6$ alkyl,
$OPO_3H_2$, $OPO-(O-(C_1$-$C_2)alkyl)_2$, the alkyl being optionally substituted by one or more fluorines, an $NH_2$,
an NH—CORc group in which Rc represents H, a $C_1$-$C_6$ alkyl, a $C_3$-$C_6$ cycloalkyl or an amino acid chain (such as $CH(CH_2OH)NH_2$ for serine),
an O—($C_1$-$C_6$)alkyl, in particular $OCH_3$, the alkyl being optionally substituted by one or more fluorines,
an O—COR1 where R1 represents O—($C_1$-$C_6$)alkyl, or NRiRii, Ri and Rii being able to be $C_1$-$C_6$ alkyl,
a $C_2$-$C_4$ alkyl group, the alkyl group being optionally substituted by one or more fluorines, a $C_2$-$C_4$ alkenyl group, substituted or not,
a $C_2$-$C_4$ alkynyl group, substituted or not, in particular by a trimethylsilyl, a tert-butyl, a hydroxy-2-propyl or an isopropyl
a heteroaryl, substituted or not, in particular a pyridine, an imidazole, an oxazole, a triazole, a pyrrole, a benzofuran, a thiophene, a benzothiophene, an indole,
a cyclohexyl, a piperazine, a morpholine, a thiomorpholine, a piperidine,
a 4-($NH_2$—($CH_2$—$CH_2O)p$)Ph group in which p is an integer from 1 to 6

6) R3 represents:
H, ($C_1$-$C_6$)alkyl, the alkyl being optionally substituted by one or more fluorines, ($C_3$-$C_6$)cycloalkyl, OH, $OPO_3H_2$, $OPO-(O-(C_1$-$C_2)alkyl)_2$, $OSO_3H$, $SO_3H$, O—($C_1$ to $C_6$)alkyl, $NH_2$, NH—($C_1$-$C_6$)alkyl, N—[($C_1$-$C_6$)alkyl]$_2$, NH—($C_3$-$C_6$)cycloalkyl, N—[($C_3$-$C_6$)cycloalkyl]$_2$, a propargyl group, $CH_2CN$, $(CH_2)_pOH$, p varying from 1 to 6, $CH_2OPO_3H_2$, $CH_2OPO-(O-(C_1$-$C_2)alkyl)_2$, $CH_2CH_2F$, $CH_2CHF_2$, $CH_2CF_3$, 7) R4 and R5 represent independently of each other:
H, OH, $OPO_3H_2$, $OPO-(O-(C_1$-$C_2)alkyl)_2$, the alkyl being optionally substituted by one or more fluorines, an O—($C_1$-$C_6$)alkyl, in particular $OCH_3$, the alkyl being optionally substituted by one or more fluorines, a $C_1$-$C_6$ alkyl, the alkyl being optionally substituted by one or more fluorines, a $C_3$-$C_6$ cycloalkyl, a halogen,
R4 and R5 represent together a ($C_1$-$C_2$) alkenyl dioxy optionally substituted by one or more fluorines, with the exclusion of the following compounds:
when X=O, R3=H, and the bond between carbon 1 and the X group is double:
a. R1=$NH_2$, R2=4-methoxy-phenyl, R4=$OCH_3$ and R5=H,
b. R1=$NH_2$, R2=phenyl, R4=H and R5=H,
c. R1=$NO_2$, R2=4-methoxy-phenyl, R4=$OCH_3$ and R5=H,
d. R1=$NO_2$, R2=4-methoxy-phenyl, R4=H and R5=H,
e. R1=$NH_2$, R2=4-methoxy-phenyl, R4=H and R5=H,
f. R1=NHCHO, R2=phenyl, R4=$OCH_3$ and R5=H,
g. R1=$NH_2$, R2=phenyl, R4=$OCH_3$ and R5=H,
h. R1=$NH_2$, R2=phenyl or 4-OH-phenyl, substituted or not, R4=H, OH, an O—($C_1$-$C_6$)alkyl, a $C_1$-$C_6$ alkyl, a $C_3$-$C_6$ cycloalkyl, and R5=H, OH, an O—($C_1$-$C_6$)alkyl, a $C_1$-$C_6$ alkyl, a $C_3$-$C_6$ cycloalkyl,
i. the compounds in which one of R4 and R5 represents a halogen.

The compounds described in this embodiment are novel.

In an advantageous embodiment, the present invention relates to a compound of general formula (I), as defined above, in which: n=0, the bond between carbon 1 and the X group is single and X is chosen from $SO_3H$, $OCH_3$,

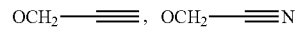

and R1 is chosen from H, $NO_2$ or Br, or n=1, the bond between carbon 1 and the X group is double, X=O or S and R2 represents a phenyl substituted in position 4 by a group chosen from OH, $OCH_3$, O-benzyl, Br, a $C_2$-$C_4$ alkynyl group, substituted or not, in particular by a trimethylsilyl, a tert-butyl, a hydroxy-2-propyl or an isopropyl.

In an advantageous embodiment, the present invention relates to a compound of general formula (I), as defined above, in which R1=H.

In an advantageous embodiment, the present invention relates to a compound as defined above, of general formula (I) below:

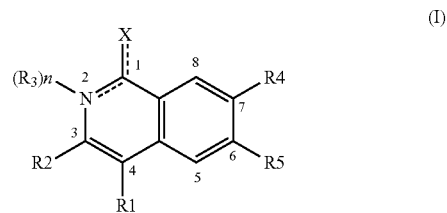

in which:
1) the bond between carbon 1 and the X group is single or double, the bond between nitrogen 2 and carbon 1 can be single or double
it being understood that:
a. when the bond between X and said carbon 1 is double, then the bond between nitrogen 2 and carbon 1 is single:
and,
b. when the bond between X and said carbon 1 is single, then the bond between nitrogen 2 and carbon 1 is double and formula I corresponds to an aromatic system of formula I-A below:

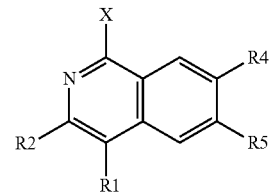

2) n represents 0 or 1,
3) X represents:
a) when n=1:
O, S, NH, N—($C_1$-$C_6$)alkyl,
b) when n=0:
OH, $OPO_3H_2$, $OPO-(O-(C_1$-$C_2)alkyl)_2$, the alkyl being optionally substituted by one or more fluorines, O—($C_1$-$C_6$)alkyl, in particular $OCH_3$, the alkyl being optionally substituted by one or more fluorines, O($C_3$-$C_6$)cycloalkyl, $NH_2$, NH—($C_1$-$C_6$)alkyl, N—[($C_1$-$C_6$)alkyl]$_2$, NH—($C_3$-$C_6$)cycloalkyl, N—[($C_3$-$C_6$)cycloalkyl]$_2$, SH, S—($C_1$-$C_6$)alkyl, the alkyl being optionally substituted by one or more fluorines, in particular SCH$_3$, S(C$_3$-C$_6$)cycloalkyl, SO$_3$H, NH—CH$_2$-aryl or heteroaryl, OPh, SPh, OCH$_2$Ph, SCH$_2$Ph, the phenyl of these four groups being able to be substituted or not by one or more (C$_1$-C$_6$)alkyls, the alkyl being optionally substituted by one or more fluorines,

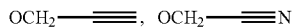

4) R1 represents:
- a halogen, OH, OPO$_3$H$_2$, OPO—(O—(C$_1$-C$_2$)alkyl)$_2$, the alkyl being optionally substituted by one or more fluorines,
- CF$_3$, CH$_2$OR', R' representing H or (C$_1$-C$_6$)alkyl, the alkyl being optionally substituted by one or more fluorines, CHO,
- CO$_2$R'', R'' representing H, an amino acid, (C$_1$-C$_6$)alkyl, the alkyl being optionally substituted by one or more fluorines,
- CONR$_c$R$_d$, R$_c$ and R$_d$ representing independently of each other: H, a C$_1$-C$_6$ alkyl, an amino acid, a C$_3$-C$_6$ cycloalkyl, or R$_c$ and R$_d$ represent together a C$_2$-C$_6$ alkyl,
- NO$_2$, N$_3$, ≡, CN, C(═N)NH$_2$, SO$_3$H, SO$_2$NH$_2$, SO$_2$NHCH$_3$, NHSO$_2$CH$_3$, CH$_2$SO$_2$NR$_c$R$_d$, CH$_2$NHSO$_2$Rc, SO$_2$—NRaRb, SO$_2$-imidazole, NR$_a$R$_b$, where:
  - R$_a$ and R$_b$ represent independently of each other: H, CHO, a C$_1$-C$_6$ alkyl, a C$_3$-C$_6$ cycloalkyl, an amino acid bound by its acid function, in particular a serine,
  - R$_a$ and R$_b$ represent together a C$_2$-C$_6$ alkyl,
  - R$_a$ and R$_b$ can form a C5 to C7 ring, in particular a pyrrolidine, a piperazine, a morpholine, a thiomorpholine,
- a heteroaryl, substituted or not, in particular a pyridine, an imidazole, an oxazole, a triazole, a pyrrole, a tetrazole.

5) R2 represents:
- a phenyl substituted or not by one to three substituents chosen from:
- a halogen, an OH, NHRa,
- ORe, Re representing a benzyl, a methylene triazole, substituted or not,
- OPO$_3$H$_2$, OPO—(O—(C$_1$-C$_2$)alkyl)$_2$, the alkyl being optionally substituted by one or more fluorines, an NH$_2$,
- an NH—Rc group in which Rc represents an amino acid bound by its acid function, in particular a serine,
- an O—(C$_1$-C$_6$)alkyl, in particular OCH$_3$, the alkyl being optionally substituted by one or more fluorines,
- a C$_2$-C$_4$ alkyl group, the alkyl group being optionally substituted by one or more fluorines, a C$_2$-C$_4$ alkenyl group, substituted or not,
- a C$_2$-C$_4$ alkynyl group, substituted or not, in particular by a trimethylsilyl, a tert-butyl, a hydroxy-2-propyl or an isopropyl
- a heteroaryl, substituted or not, in particular a pyridine, an imidazole, an oxazole, a triazole, a pyrrole, a benzofuran, a thiophene, a benzothiophene, an indole,
- a cyclohexyl, a piperazine, a morpholine, a thiomorpholine, a piperidine,
- a 4-(NH$_2$—(CH$_2$—CH$_2$O)p)Ph group in which p is an integer from 1 to 6.

6) R3 represents:
- H, (C$_1$-C$_6$)alkyl, the alkyl being optionally substituted by one or more fluorines, (C$_3$-C$_6$)cycloalkyl, OH, OPO$_3$H$_2$, OPO—(O—(C$_1$-C$_2$)alkyl)$_2$, O—(C$_1$ to C$_6$)alkyl, NH$_2$, NH—(C$_1$-C$_6$)alkyl, N—[(C$_1$-C$_6$)alkyl]$_2$, NH—(C$_3$-C$_6$) cycloalkyl, N—[(C$_3$-C$_6$)cycloalkyl]$_2$, a propargyl group, CH$_2$CN, (CH$_2$)$_p$OH, p varying from 1 to 6, CH$_2$OPO$_3$H$_2$, CH$_2$OPO—(O—(C$_1$-C$_2$)alkyl)$_2$, CH$_2$CH$_2$F, CH$_2$CHF$_2$, CH$_2$CF$_3$, 7) R4 and R5 represent independently of each other:
- H, OH, OPO$_3$H$_2$, OPO—(O—(C$_1$-C$_2$)alkyl)$_2$, the alkyl being optionally substituted by one or more fluorines, an O—(C$_1$-C$_6$)alkyl, in particular OCH$_3$, the alkyl being optionally substituted by one or more fluorines, a C$_1$-C$_6$ alkyl, the alkyl being optionally substituted by one or more fluorines, a C$_3$-C$_6$ cycloalkyl, a halogen,
- R4 and R5 represent together a (C$_1$-C$_2$) alkenyl dioxy optionally substituted by one or more fluorines, In another embodiment, the compound defined above of general formula (IIa) is chosen from the following:

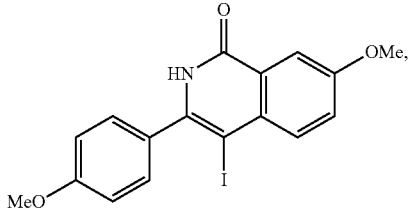

16

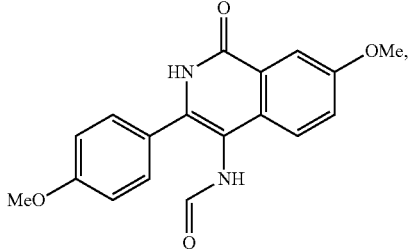

24

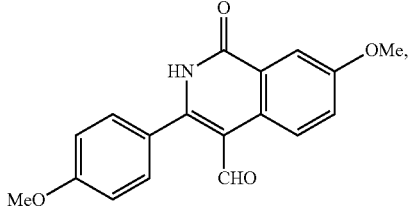

25

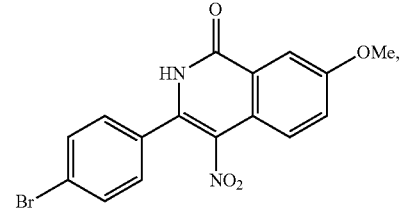

34

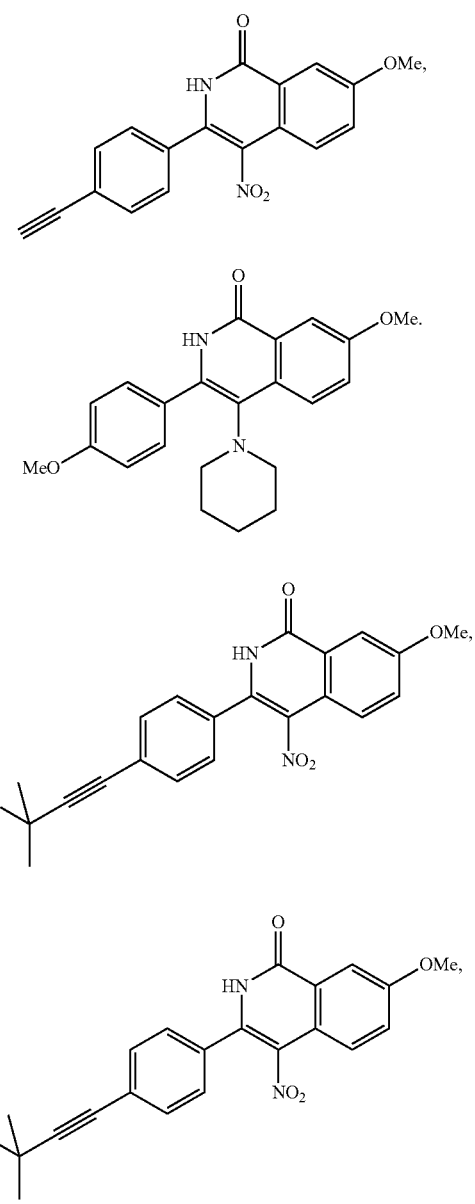

In another advantageous embodiment, the invention relates to a novel product comprising a first pharmaceutical preparation of formula (I) defined above, and a second pharmaceutical preparation comprising but not limited to at least one of the following antitumour drugs:

abraxane, abarelix, aldesleukin, alemtuzumab, alitretinoin, allopurinol, altretamine, anastrozole, arsenic trioxide, asparaginase, azacitidine, bevacizumab, bexarotene, bicalutamide, bleomycin, bortezomib, intravenous busulphan, oral busulphan, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, 5-fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, taxol, taxotere, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate,
as combined preparation for a simultaneous, separate or sequential use in the treatment of mammals, in particular humans, suffering from benign or malignant (cancerous) tumours.

In an advantageous embodiment, the invention relates to a novel product comprising a first pharmaceutical preparation of formula (I) defined above, and a second pharmaceutical preparation comprising at least one of the antitumour drugs defined above as combined preparation for a simultaneous, separate or sequential use in the treatment of mammals, in particular humans, suffering from benign or malignant (cancerous) tumours, According to another aspect, the invention relates to a method for preparing compounds of formula IIa as defined above, comprising the following stages:
for X=O:
a) condensation of an arylacetic acid with an arylcarboxaldehyde in order to form a 2,3-diarylacrylic acid intermediate,
b) conversion of the acid group to the corresponding azide with $NaN_3$ via a mixed anhydride,
c) cyclization of the azide by thermal route in order to produce 3-arylisoquinolin-1(2H)-one,
d) arrangement of the functional groups according to the protocols detailed below.
for X=S,
a) starting from 3-arylisoquinolin-1(2H)-one, the synthesis of isoquinolin-1(2H)-thione is carried out with Lawesson's reagent,
b) starting from 3-aryl-4-nitroisoquinolin-1(2H)-one, the isoquinolin-1(2H)-thione synthesis method comprises the following main stages:
  i. chlorination with phosphorus chloride oxide or with Vilsmeier reagent in order to form the 1-chloroisoquinoline intermediate,
  ii. conversion of the chloro group to a thione group with thiourea.

According to another aspect, the invention relates to a method for preparing compounds of formula IIb as defined above, comprising the following stages
starting from 3-arylisoquinolin-1(2H)-one: the synthesis of isoquinoline IIb is carried out with the desired haloakyl in the presence of a base such as $K_2CO_3$;
starting from 1-chloro-4-nitroisoquinoline the synthesis of which was mentioned above: the synthesis of isoquinoline IIb carried out with the desired nucleophile in basic medium.

DESCRIPTION OF THE FIGURES

FIGS. 1A to 1C represent the microtubules labelled with an anti α-tubulin antibody and FIGS. 1D to 1F represent F-actin labelled with a phalloidin conjugate Alexa Fluorine® 568.

FIGS. 1A and 1D represent the control cells incubated with DMSO.

FIGS. 1B and 1E represent the cells incubated with compound 6 at a concentration of 1 µM for 24 hours.

FIGS. 1C and 1F represent the cells incubated with compound 6 at a concentration of 10 µM for 24 hours.

FIGS. 2A to 2C represent the microtubules labelled with an anti α-tubulin antibody. FIGS. 2D to 2F represent F-actin labelled with a phalloidin conjugate Alexa Fluorine® 568. FIGS. 2G to 2I represent the superimposition of the 2 images showing the tubulin and actin with, in addition, the mitotic DNA [black arrows (1) corresponding to the DNA labelled with Hoechst 33258].

FIGS. 2A, 2D and 2G represent the control cells, incubated with DMSO.

FIGS. 2B, 2E and 2H represent the cells incubated with compound 6 at a concentration of 1 µM for 24 hours.

FIGS. 2C, 2F and 2I represent the cells incubated with compound 6 at a concentration of 10 µM for 24 hours.

FIGS. 3A to 3C represent the microtubules labelled with an anti α-tubulin antibody and FIGS. 3D to 3F represent F-actin labelled with a phalloidin conjugate Alexa Fluorine® 568.

FIGS. 3A and 3D represent the control cells, incubated with DMSO.

FIGS. 3B and 3E represent the cells incubated with compound 6 at a concentration of 5 µM for 24 hours.

FIGS. 3C and 3F represent the cells incubated with compound 6 at a concentration of 10 µM for 24 hours.

FIGS. 4A to 4C represent the microtubules labelled with an anti α-tubulin antibody, FIGS. 4D to 4F represent F-actin labelled with a phalloidin conjugate Alexa Fluorine® 568. FIGS. 4G to 4I represent the superimposition of the 2 images showing the tubulin and actin with, in addition, the mitotic DNA [black arrows (1) corresponding to the DNA labelled with Hoechst 33258].

FIGS. 4A, 4D and 4G represent the control cells, incubated with DMSO.

FIGS. 4B, 4E and 4H represent the cells incubated with compound 6 at a concentration of 5 µM for 24 hours.

FIGS. 4C, 4F and 4I represent the cells incubated with compound 6 at a concentration of 10 µM for 24 hours.

They show the accumulation of rounded HeLa cells in the presence of compound 6 (0.5 µM).

The images were taken in the same field, every 5 minutes over 24 hours using a Neofluar 20× objective (Zeiss).

FIGS. 6A to 6D present the phase contrast microscopy images showing the cortical blebbings induced by compound 6 (0.5 µM) on HeLa cells (in interphase and in mitosis).

Figure 1:
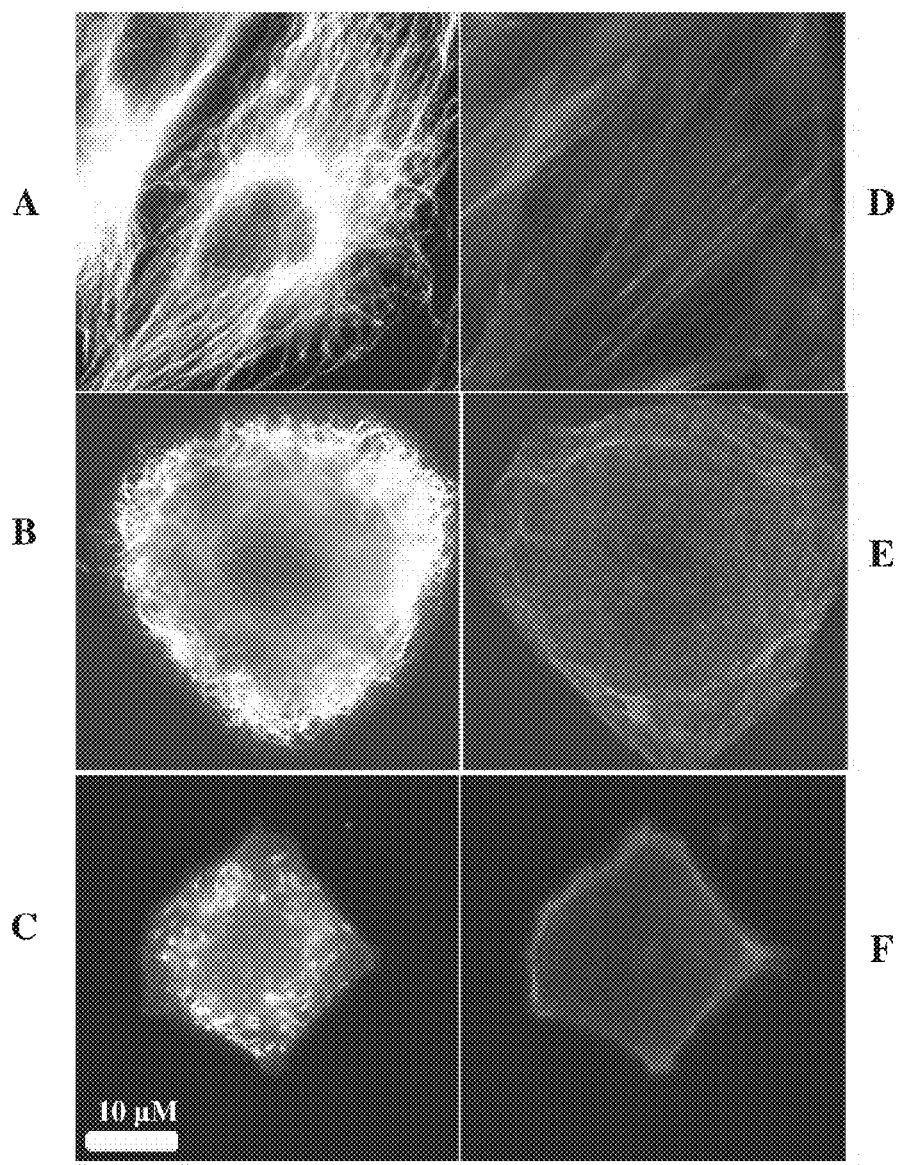
FIGS. 1A to 1F represent indirect immunofluorescence images showing the phenotypes induced by compound 6 on the microtubules and actin cytoskeleton of HeLa cells in interphase. This compound induces a depolymerization of the microtubules and a reorganization of the actin cytoskeleton (reinforcement of the actin at the level of the cell cortex and reduction in stress fibres).
Figure 2:
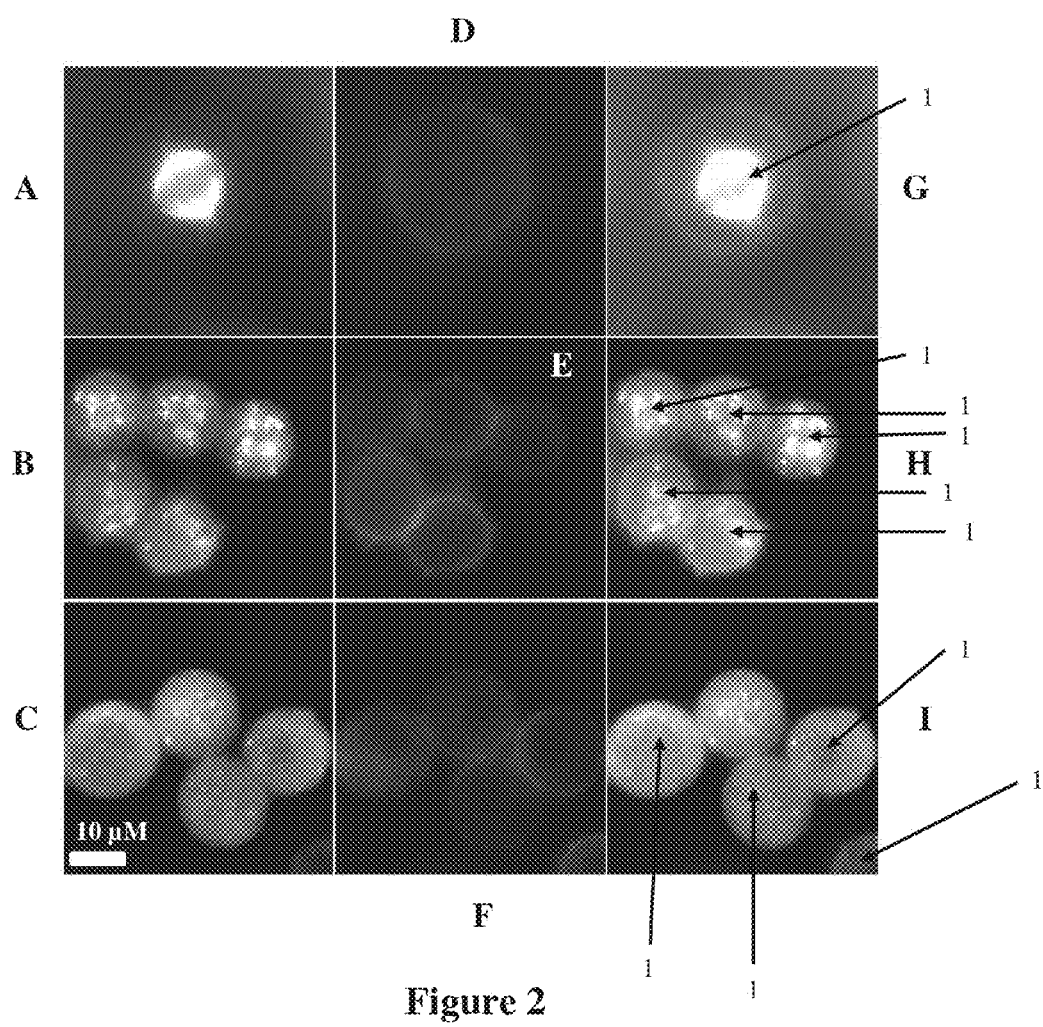
FIGS. 2A to 2I represent indirect immunofluorescence images showing the phenotypes induced by compound 6 on the microtubules and actin cytoskeleton of HeLa cells in mitosis. This compound induces a depolymerization of the spindle microtubules and actin blebbing at the level of the cortex.
Figure 3:
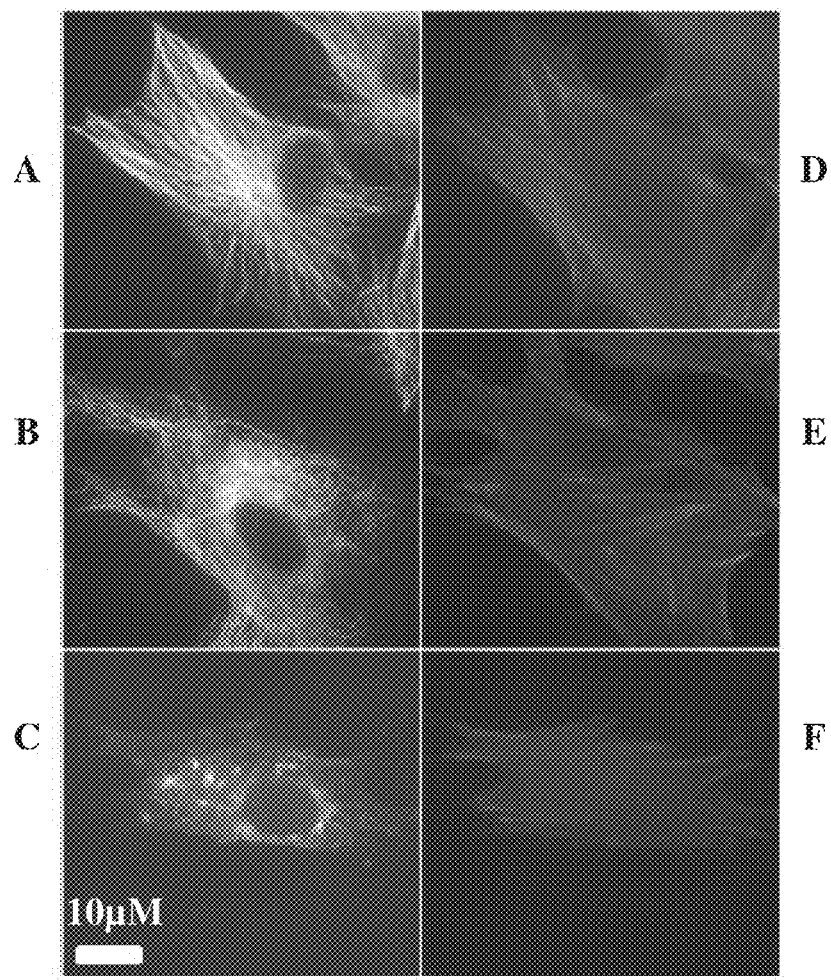
FIGS. 3A to 3F represent the indirect immunofluorescence images showing the phenotypes induced by compound 6 on the microtubules and the actin cytoskeleton of the primary human fibroblasts in interphase. This compound induces a depolymerization of the microtubules and a reorganization of the actin cytoskeleton (slight reinforcement of the actin at the level of the cell cortex).
Figure 4:
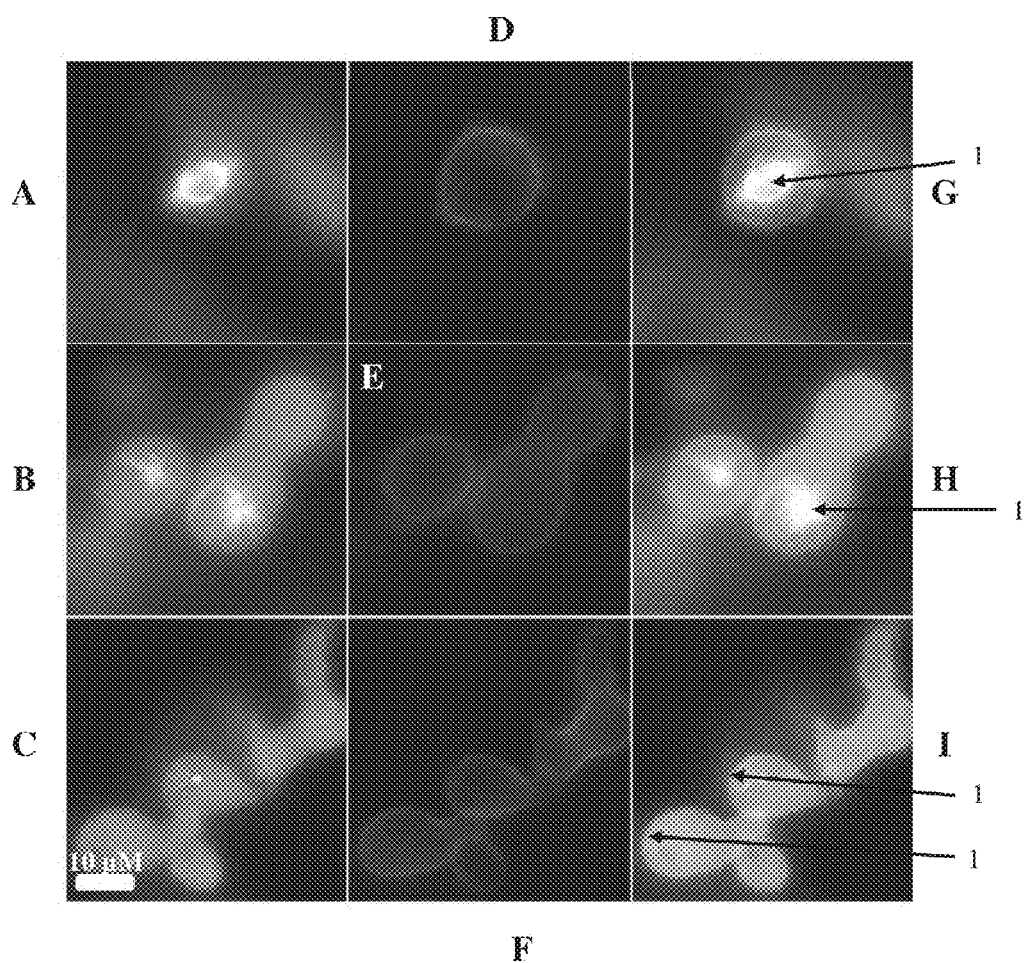
FIGS. 4A to 4I represent the indirect immunofluorescence images showing the phenotypes induced by compound 6 on the microtubules and the actin cytoskeleton of the primary human fibroblasts in mitosis. This compound induces a depolymerization of the spindle microtubules and the formation of ectopic furrows.
Figure 5:
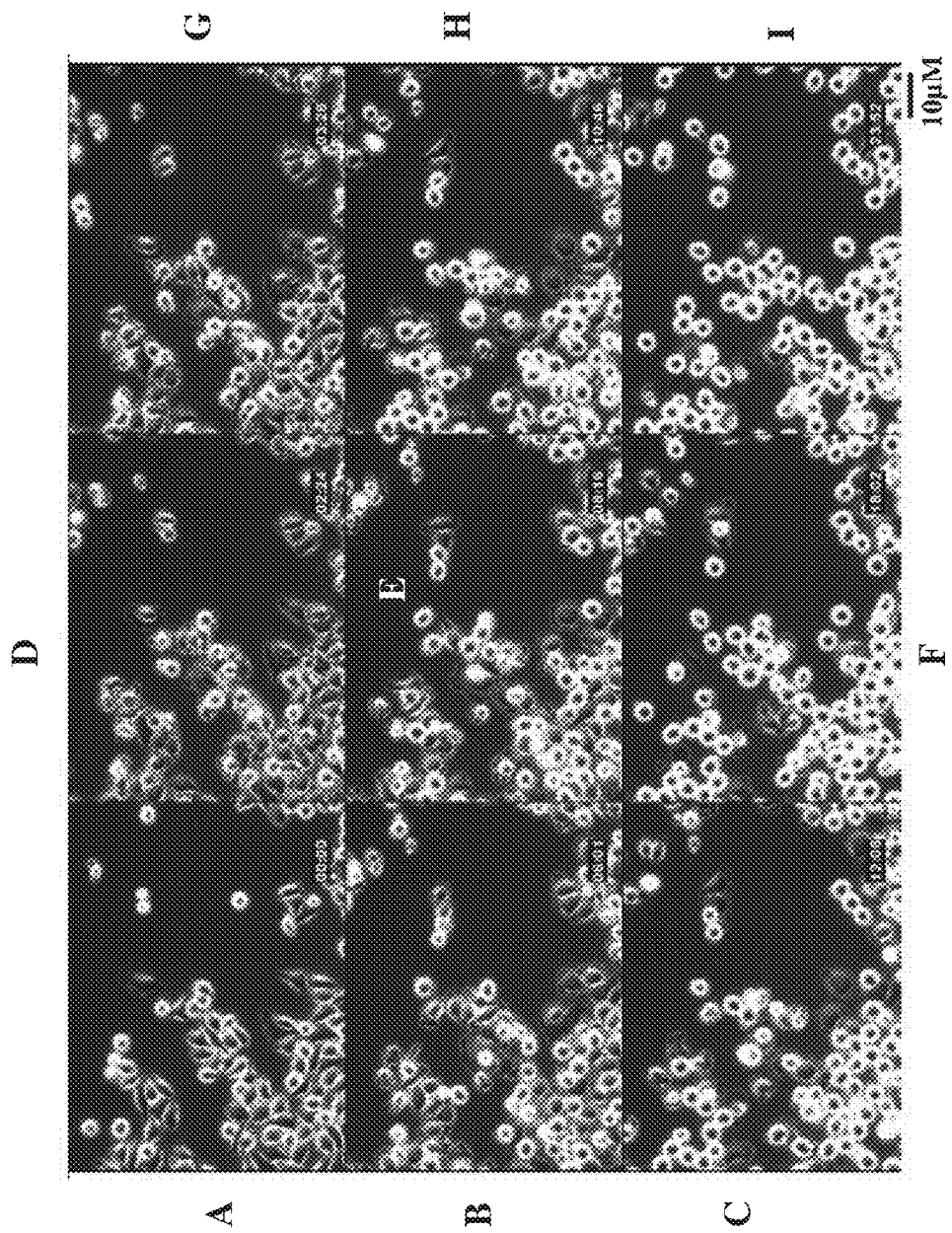
FIGS. 5A to 5I illustrate the mitotic arrest induced by compound 6 on HeLa cells, in phase contrast microscopy over 24 hours (video microscopy).
Figure 6:
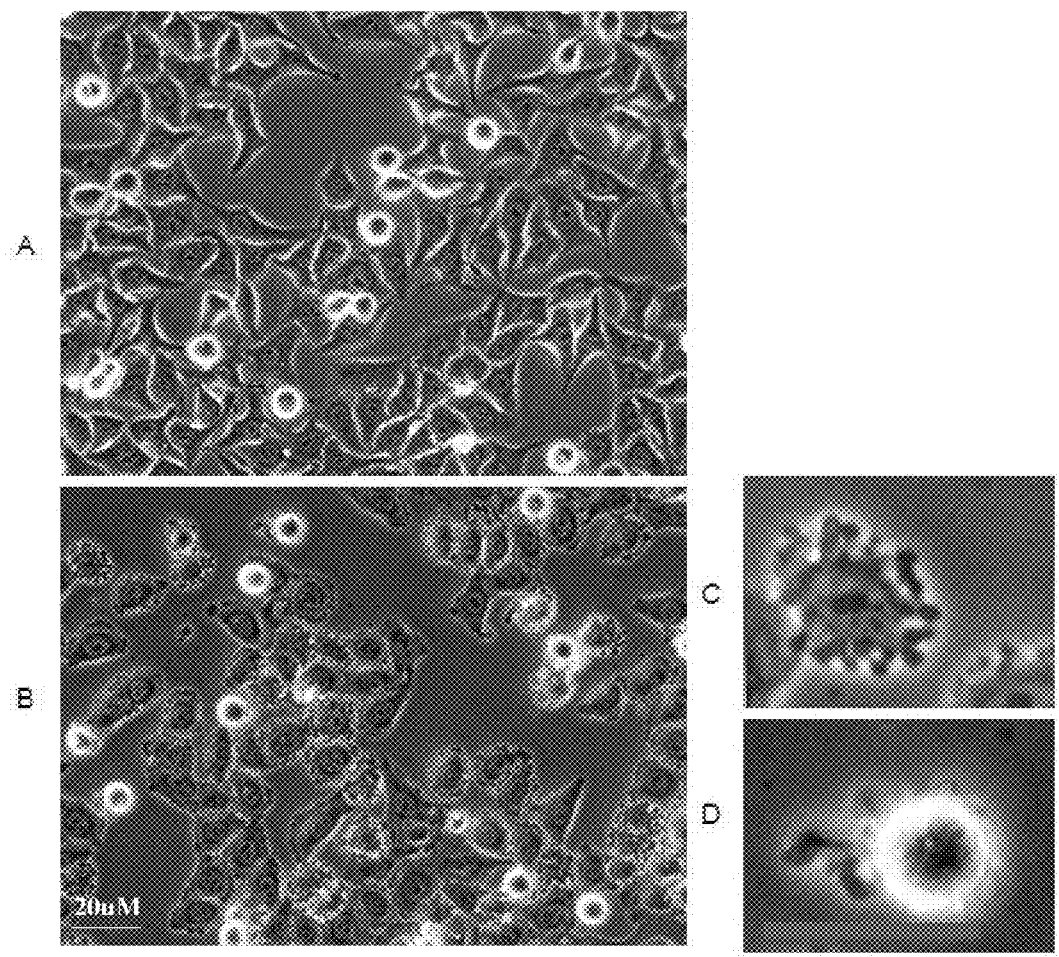

FIG. 6A: Control cells, incubated with DMSO.

FIG. 6B: Cells after incubating for 3 hours with compound 6.

FIG. 6C: Zoom view of an interphase adherent cell after incubating for 3 hours with compound 6 (originating from FIG. 6B).

FIG. 6D: Zoom view of a rounded cell after incubating for 3 hours with compound 6 (originating from FIG. 6B).

Acquisition of images with a Neofluar 20× objective (Zeiss).

Figure 7:
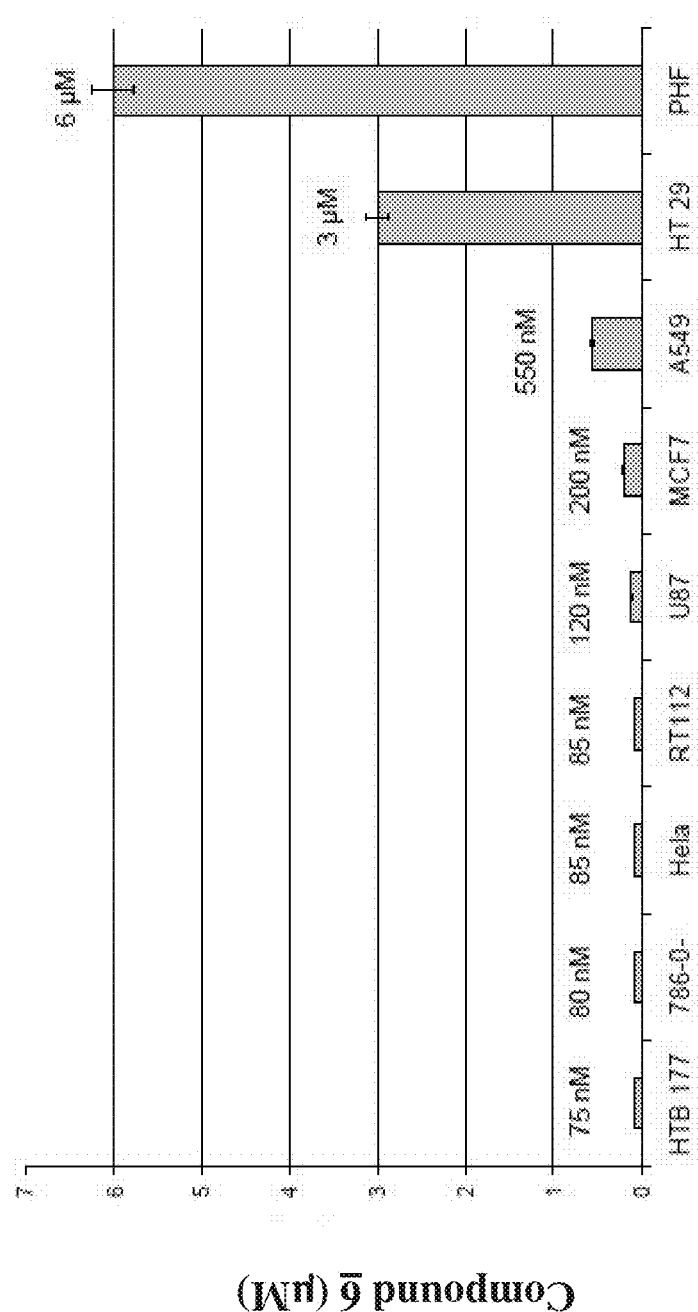

FIG. 7 presents a graph showing the antiproliferative activity of compound 6 on different cell types.

It shows the concentration of compound 6 necessary to inhibit the proliferation of different cells or cell lines by 50% (GI50 for Growth Inhibition 50).

The values are indicated as the average±SEM of two experiments carried out in triplicate.

Figure 8:
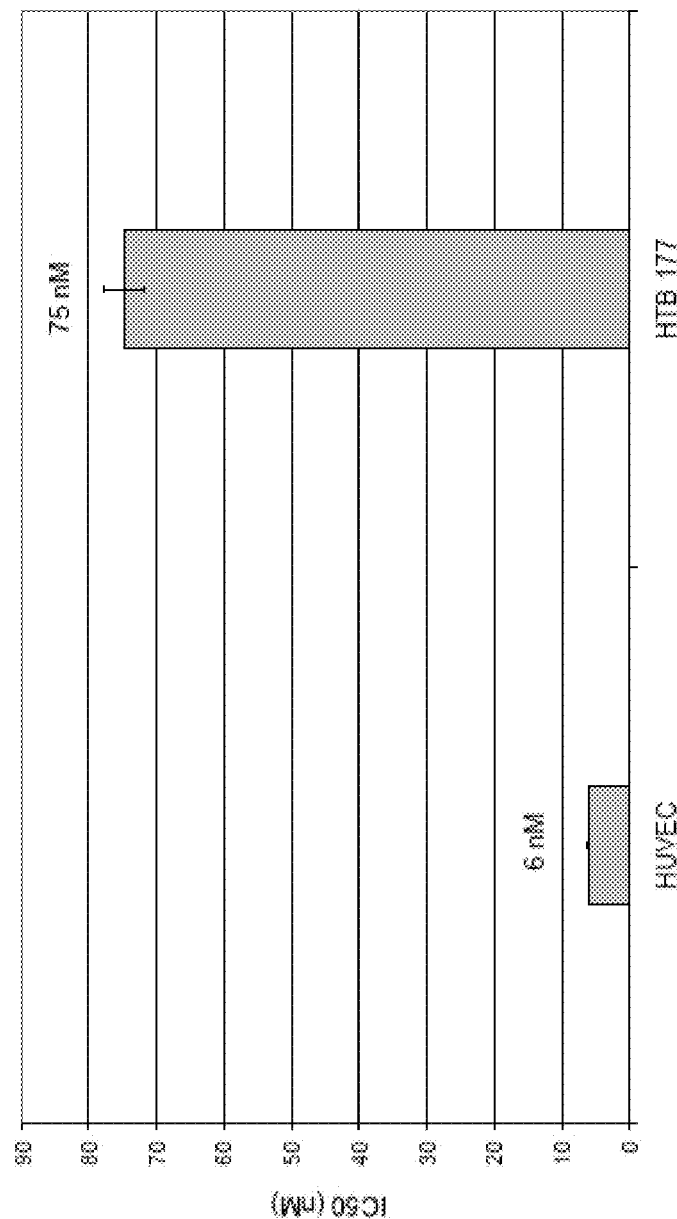

FIG. 8 presents the graph showing the antiproliferative activity of compound 6 on the HUVECs and the HTB177 cell line.

It shows the concentration of compound 6 necessary to inhibit the proliferation of HTB177 cells (the cell line most sensitive to compound 6) and HUVECs (human umbilical vein endothelial cells) by 50%.

The values are indicated as the average±SEM of two experiments carried out in triplicate.

Figure 9:
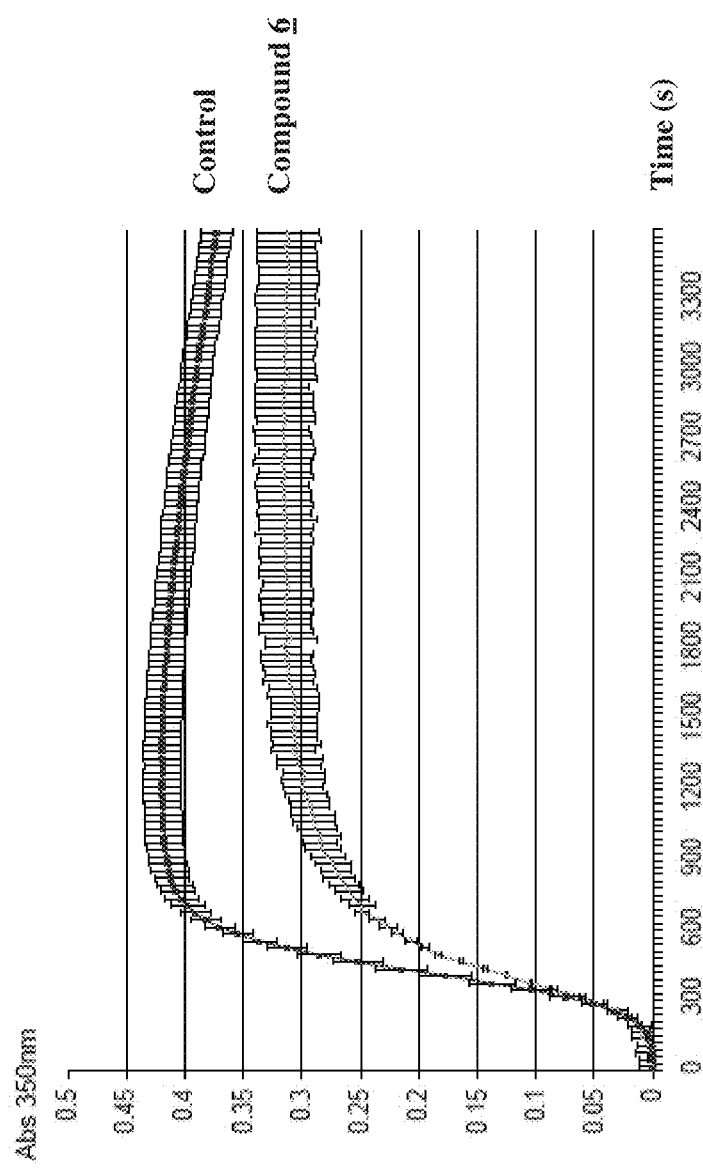

FIG. 9 presents the graph showing the effect of compound 6 (50 µM) on tubulin polymerization in vitro.

The control is carried out with 0.5% DMSO which corresponds to the quantity of DMSO added to the molecule 6 as the latter is solubilized in DMSO.

The values are indicated as the average±SEM of two experiments carried out in triplicate.

Figure 10:
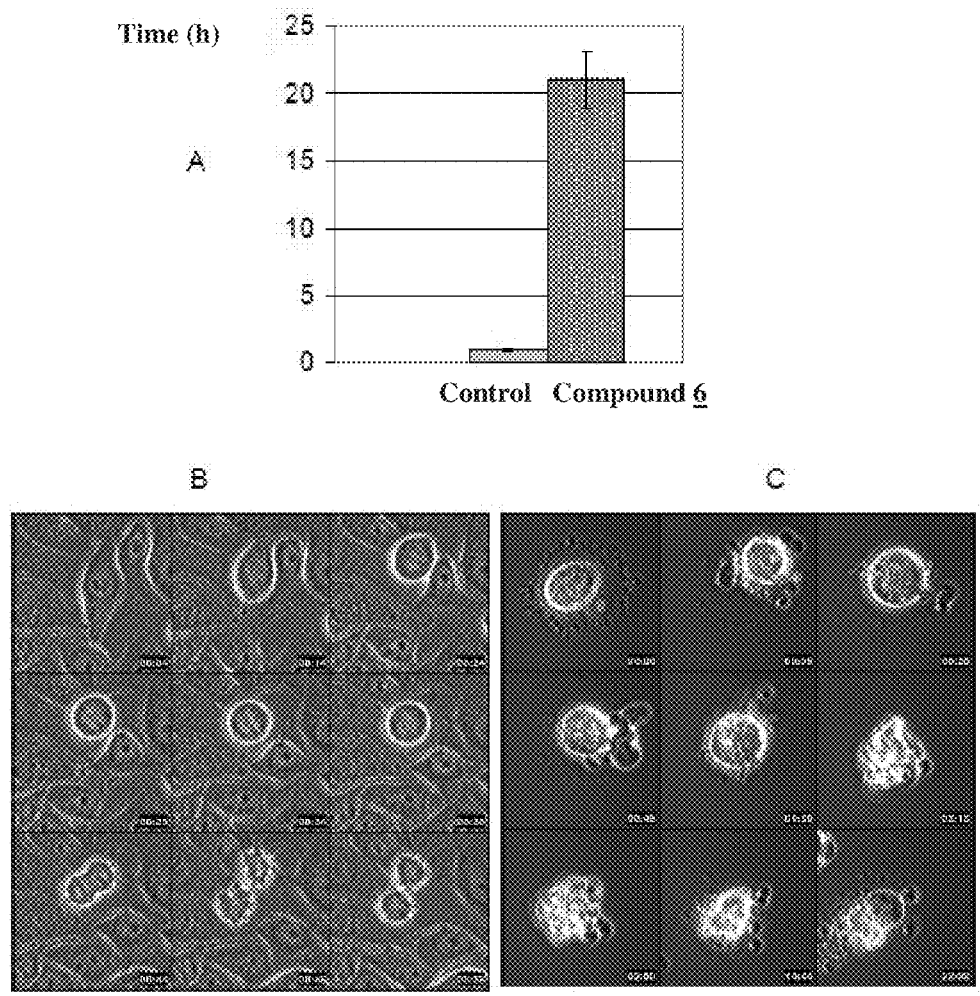

FIGS. 10A to 10C present the graph showing the duration of the mitosis of HeLa cells in the presence of compound 6 as well as the phase contrast microscopy illustration of the development of these cells arrested in mitosis.

Compound 6 increases the duration of mitosis in the HeLa cells compared with the control cells (DMSO).

FIG. 10A: mitosis lasts 22 hours in the presence of 0.5 µM of compound 6 whereas it lasts 1 hour under control conditions.

FIG. 10B: control. After 1 hour the cell divides into 2 daughter cells.

FIG. 10C: (phase contrast) video microscopy monitoring of mitosis in the presence of 0.5 µM of compound 6. The mitosis lasts 22 hours with a strong membrane blebbing activity until the cell dies. 80% of the mitotic cells observed show intense blebbing, 20% of the cells remaining rounded.

The cells were filmed over 48 hours (image acquisition every 5 minutes) with a Neofluar 40× objective (Zeiss).

The values of FIG. 10A are averages±SEM of two experiments in which 50 mitotic cells were monitored.

FIGS. 11A to 11D present the phase contrast microscopy images showing that the simultaneous suppression of the three isoforms of PP1 (α+β+γ) in HeLa cells, by siRNA, reproduces the phenotype induced by compound 6.

The simultaneous suppression of the three isoforms of PP1 by the siRNA induces membrane blebbing of the HeLa cells 48 hours after transfection.

Figure 11:
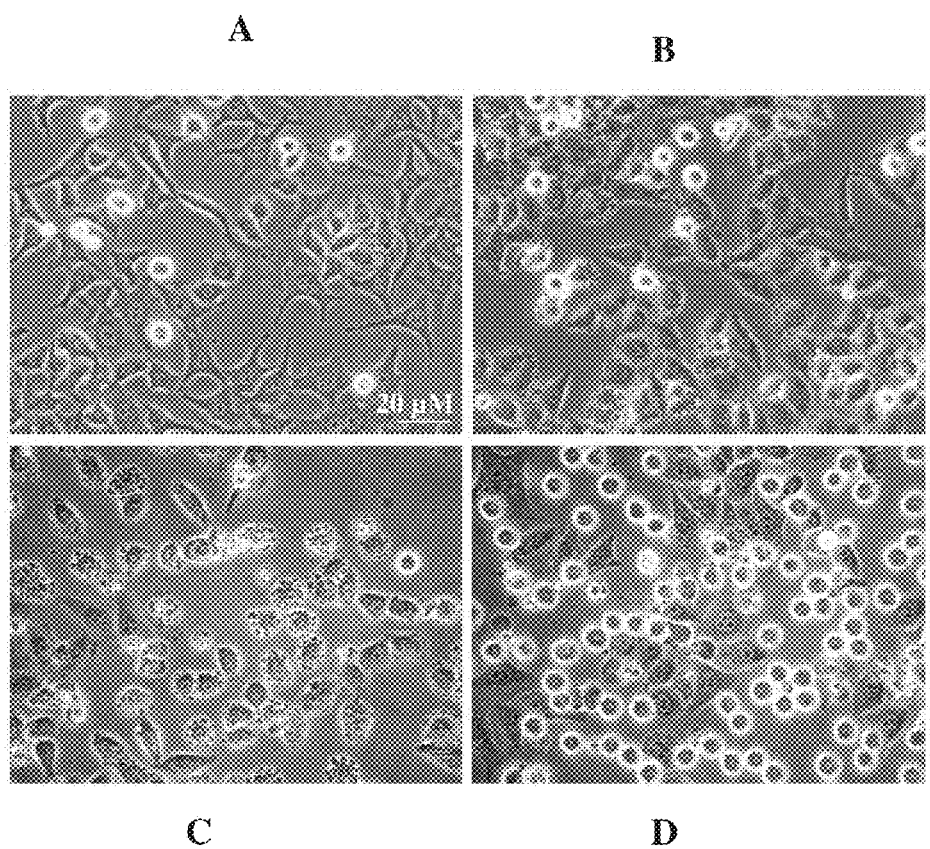

FIG. 11A: control cells.

FIG. 11B: HeLa cells incubated with compound 6 at 0.5 µM for 3 hours.

FIG. 11C: the suppression of the three catalytic subunits of PP1 leads to the appearance of a phenotype membrane blebbing identical to that of FIG. 11B.

FIG. 11D: the suppression of the catalytic domain of PP2A by the corresponding siRNA, induces an accumulation of rounded cells.

FIGS. 12A and 12B present compound 37 which specifically retains the catalytic domain(s) of PP1.

(A) The structure of compound 37 (corresponds to compound 6 with a PEG group).

(B) Compound 37 immobilized on sepharose resin specifically retains PP1C. Immunoblot analysis of the eluates under conditions 1 and 2 with anti-PP1C and anti-PP2A antibodies.

1: Sepharose N-HydroxySuccinimide blocked by monoethanolamine (control).

2: Compound 37 coupled with NHS Sepharose.

The absence of PP1C in the control and similar quantities of PP2A (in the state of traces), under both conditions (MW: molecular weight) should be noted.

Figure 13:
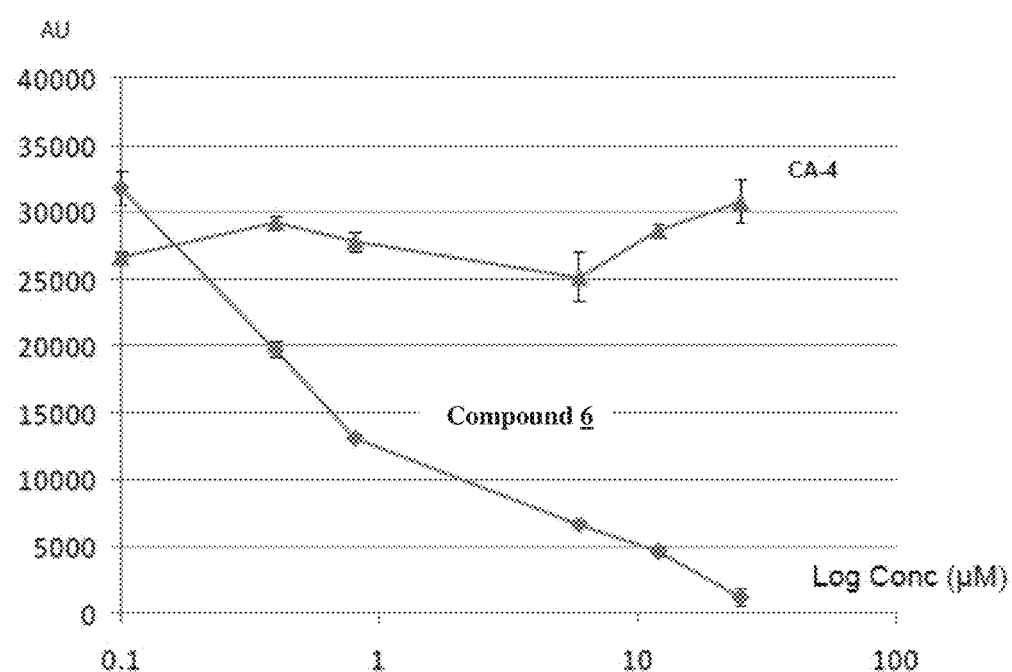

FIG. 13 presents the graph showing the inhibition of the PP1Cα activity by compound 6 in vitro. PP1Cα (New England Biolabs, 30 mU/well) was incubated in the presence of compound 6 at different concentrations and a fluorescent substrate, diFMUP.

It should be noted that combretastatin A-4 (CA-4) (substance used as negative control) does not inhibit PP1 activity.

The values are indicated as the average±SEM of two experiments carried out in triplicate.

AU: Arbitrary units.

Figure 14:
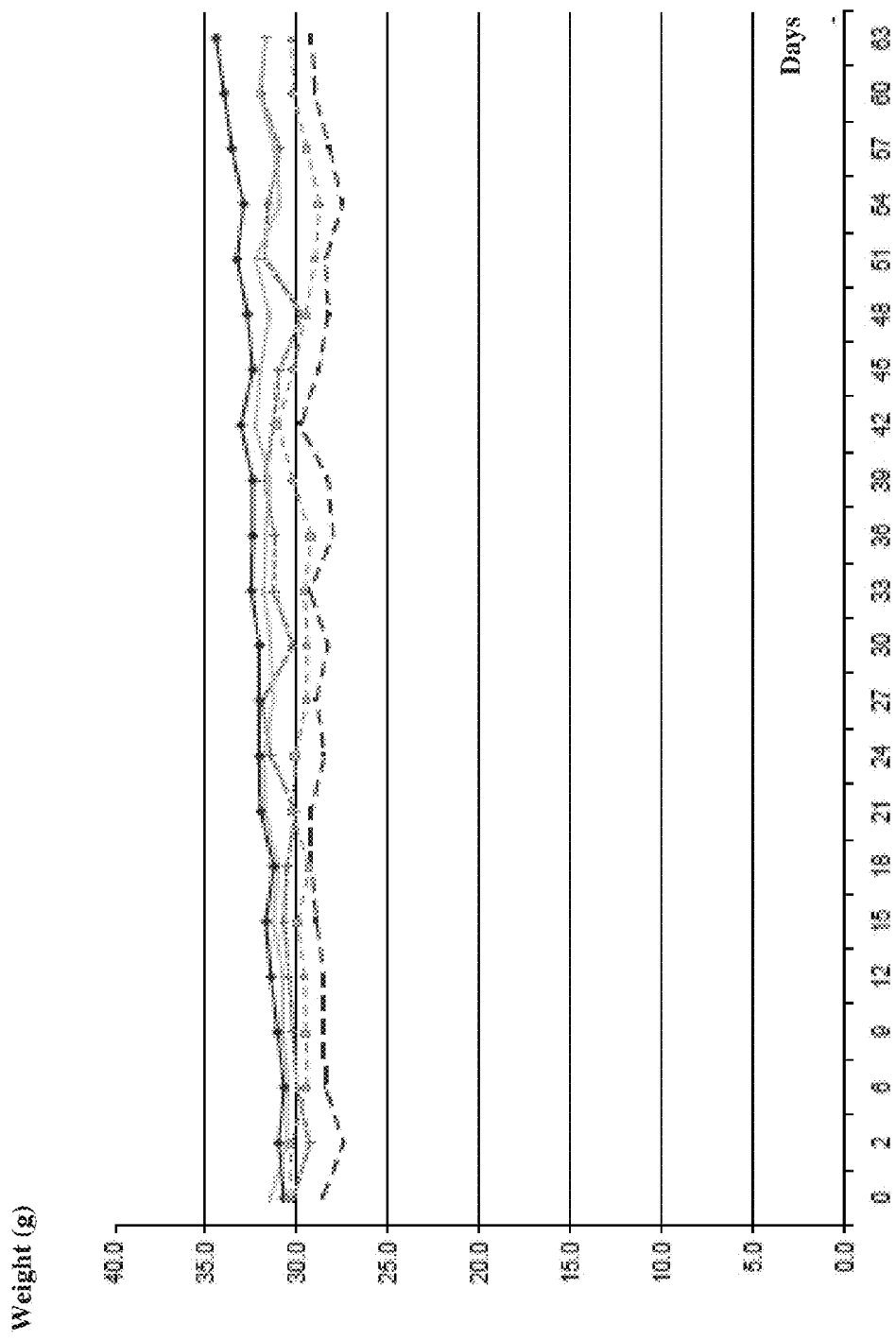

FIG. 14 presents the change in the weight of nude mice over 63 days. The mice received an administration of compound 6 (200 mg/kg) per os twice weekly over 2 months.

Compound 6 was dissolved at 8 mg/ml in a 60 mg/ml aqueous solution of beta-cyclodextrin (vehicle).

Compound 6 has no significant effect on the weight of the nude mice.

Figure 15:
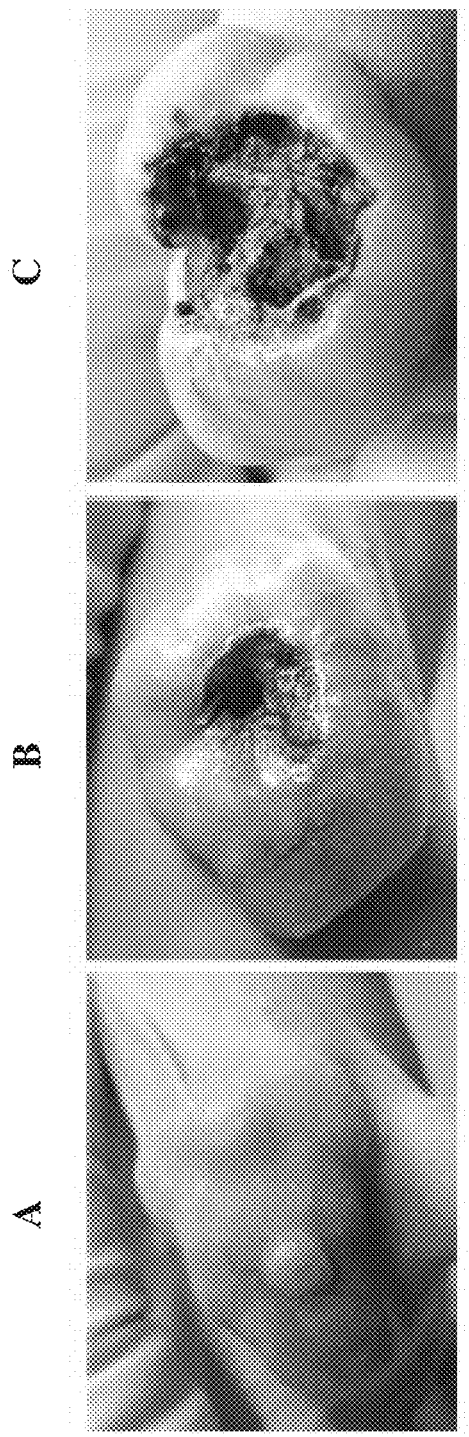

FIGS. 15A to 15C present images of human tumours (HTB-177: pulmonary carcinoma) xenografted onto nude mice after treatment with compound 6 (40 mg/kg administered twice weekly per os) or the vehicle alone.

FIG. 15A: control tumour on day 7.

FIG. 15B: tumour treated with compound 6 on day 7.

FIG. 15C: tumour treated with compound 6 on day 20.

The animals xenografted with HTB-177 treated orally with compound 6 already show central necrosis after a cycle of administration of compound 6 (day 7). It should be noted that the control animals show no sign of necrosis.

FIGS. 16A to 16D present the photographs showing the necrosis of xenografted tumours (HTB177) 48 hours after administration of compound 6 (40 mg/kg). The tumour sections (10 µm in thickness) have been stained with H&E (haematoxilin-eosin). The tumour sections originating from animals treated with compound 6 show extensive areas of necrosis whereas the control tumour tissues are intact.

Figure 16:
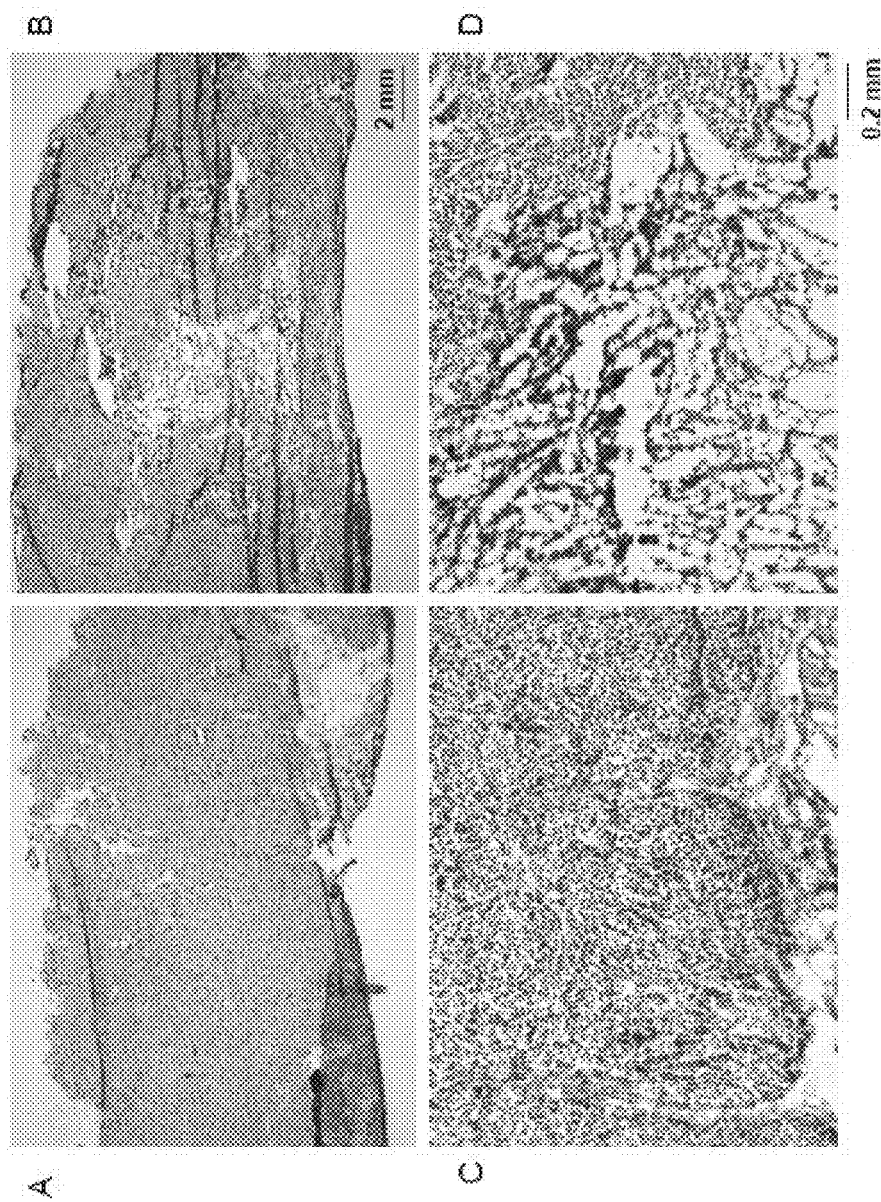

FIGS. 16A and 16C present tumour sections obtained from control animals.

FIGS. 16B and 16D present tumour sections after treatment with compound 6.

MATERIAL AND METHODS

Example 1

Cell Culture

All the culture media were enriched with Foetal Bovine Serum (10%), Penicillin (100 U/ml) and Streptomycin (100 mg/ml). The cells are cultured in an oven at 37° C. in the presence of 5% $CO_2$.

Primary human fibroblasts (PHFs) were prepared from newborn foreskins as described in (Nahm W K et al., J Dermatol Sci. 2002, 28(2): pp 152-8).

The following cell lines: HeLa (ATCC # CCL-2, human cervical carcinoma), NCI-H460 (ATCC #HTB-177, human pulmonary large cell carcinoma), 786-0 (ATCC # CRL-1932, human renal adenocarcinoma), RT-112 (Benham F et al., J Histochem Cytochem. 1977, 25: pp 266-74, human bladder carcinoma), HMEC (Pasquier E et al., Mol Cancer Ther 9(5) 2010, pp 1408-18: ENMD-1198, a new analogue of 2-methoxyestradiol, displays both antiangiogenic and vascular-disrupting properties) were cultured in an RPMI 1640 medium.

The following cell lines: U87 (ATCC # HTB-14, human glioblastoma), HT-29 (ATCC # HTB-38, grade II human colon adenocarcinomona), MCF7 (ATCC # HTB-22, human breast adenocarcinoma) were cultured in a DMEM medium. For the MCF7, the medium was enriched with insulin (0.01 mg/ml).

A549 cells (ATCC #CCL-185, human lung carcinoma) were cultured in an F-12K medium. HUVECs (Human Umbilical Vein Endothelial Cells, PromoCell # c-12203) were cultured in an endothelial cell growth medium recommended by the supplier (Promocell # c-22010).

Example 2

In Vitro and In Vivo Tests of the Molecules of the Invention

For the in vitro studies, all the molecules were resuspended in anhydrous DMSO in order to produce a 10 mM stock solution and stored in aliquots at −20° C.

For the in vivo experiments, molecule 6 (8 mg/ml) was prepared in 60 mg/ml of β-cyclodextrin (Sigma #4805) dissolved in water and vortexed.

Example 3

*Xenopus* Egg Extracts

*Xenopus* egg cytoplasmic extracts were prepared from unfertilized *Xenopus laevis* eggs according to the method described (Desai A et al., Methods Cell Biol. 1999; 61: pp 385-412).

Example 4

Indirect Immunofluorescence of the Cells

The cells were cultured on slides in 24-well plates and incubated for 24 hours with molecule 6 at different concentrations from 1 to 10 µM.

Corresponding quantities of DMSO were added to the culture medium in the control wells.

The cells were fixed in a solution of PBS with 4% paraformaldehyde (PFA) and 0.1% glutaraldehyde (GA), for 15 minutes and centrifuged at 300 g for the last 10 minutes of the fixing. The slides were rinsed in PBS and the free aldehyde groups were reduced by two successive 5-minute incubations in PBS containing 1 mg/ml of NaBH4.

After one washing with PBS then another with PBST (PBS with 0.5% triton-X-100), the cells are incubated for 30 minutes at ambient temperature with anti α-tubulin monoclonal antibody solution (DM1A clone, Sigma # T6199) diluted to 1:200 in PBST. After 3 10-minute washings with PBST, the cells are incubated for 30 minutes at ambient temperature in a solution of goat anti-mouse polyclonal antibodies coupled with Alexa 488 (1:1000, Molecular Probes # A-11029) and phalloidin coupled with Texas red to label the actin (1:2000, Molecular Probes # T7471), in PBST also containing Hoechst 33258 (1 µg/ml) for labelling the DNA. After 3 10-minute washings in PBST, the slides are mounted on plates in Fluorsave™ mounting medium (Calbiochem #345789) and are observed and analyzed using an Axiovert 200M inverted fluorescence microscope (Zeiss®). The images are produced with a Plan-Apochromat 63× oil objective (Zeiss®) by means of a Coolsnap HQ camera (Roper Scientifics®) and with Metamorph acquisition software (Universal Imaging™ Corporation).

In order to evaluate the effect of the analogues of compound 6 on PHFs and HeLa cells, the immunofluorescence technique described above was used and adapted to a 96-well dish format. The cells were seeded in glass-bottomed 96-well dishes and incubated for 24 hours in the presence of different concentrations of molecules from 100 µM to 50 nM. And in the same way as described above, the cells were fixed and immunolabelled. Analysis of the phenotypes as well as counting the mitotic cells were carried out with the same microscope but using a ×40 objective (Olympus). The molecules were compared with each other with respect to the mitotic arrest induced on PHFs and HeLa cells at 25 and 0.3 µM.

For z-series video microscopy, HeLa cells were cultured in glass-bottomed dishes (Iwaki, Milian # BY-3910035). The system comprises: an AXIOVERT 200M inverted microscope (Zeiss®), a thermostated incubation chamber which maintains a temperature of 37° C. and a constant $CO_2$ level of 5%, a motorized platform and a CoolSNAP HQ camera (Roper Scientifics®) coupled with the Metamorph acquisition and analysis system (Universal Imaging™ Corporation). The studies were carried out with ×20 or ×40 objectives (Neofluar Zeiss).

Initially, the acquisition fields were chosen and stored in the memory, then the acquisition parameters were defined, such as the duration of the experiment (48 hours), the interval between the image captures (5 minutes), or the number of sections at depth z (9 sections). At the end of 48 hours of recording, the acquisition batteries were reconstituted with the image at z having the same focus, using the Metamorph software.

Example 5

Cell Proliferation Test

The cells were seeded in 96-well plates (1,000 per well) and incubated with different concentrations of compound 6 (1 nM to 100 µM), for 5 days (120 hours). At the end of this incubation, Hoechst 33342 (1 µg/ml) was added to the culture medium and the live cells were counted under a fluorescence microscope (Zeiss Axiovert 200M). The data represents the average of two independent experiments during which 10 fields chosen at random were analyzed for each concentration of compound 6, themselves produced in triplicate.

Example 6

Purification of Bovine Brain Tubulin and In Vitro Polymerization Test

Tubulin was purified from bovine brain using the polymerization-depolymerization process described by (Castoldi M and Popov A V. Protein Expr Purif. 2003, 32(1): pp 83-8).

The in vitro tubulin polymerization tests (at 50 µM) were carried out in the presence of GTP 1 mM in BRB80 buffer (80 mM K-PIPES pH 6.8, 1 mM $MgCl_2$, 1 mM EGTA) at 37° C. The tests were carried out in 96-microwell plates (half-wells) (Costar plates, Corning #3695), in triplicate with a final volume of 70 µl. Tubulin assembly was carried out in the presence of compound 6 or its analogues (all used at a concentration of 50 µM) and was monitored by turbidimetry measurement at 350 nm using a spectrophotometer (Spectramax More, Molecular Devices).

The in vitro results obtained in Examples 4, 6, 9 and with the compounds of the invention are recorded in Table I below

TABLE I

| No. | Code | Structure | Molecular formula | MW | PP1 Inhibition IC50 | Tubulin polymerization inhibition | Effect on Hela at 25 µM | GI50 on HMEC |
|---|---|---|---|---|---|---|---|---|
| 1 | ICC₁28-L-004-H09 | (structure) | $C_{17}H_{16}N_2O_3$ | 296.32 | — | — | *** | ++ |
| 2 | ICC₁08-L-006-C05- | (structure) | $C_{15}H_{12}N_2O$ | 236.28 | — | — | — | + |

TABLE I-continued

| | | | Formula | MW | | | | |
|---|---|---|---|---|---|---|---|---|
| 4 | ICC$_1$23-L-022-C04- | | C$_{17}$H$_{15}$NO$_3$ | 281.3 | — | — | — but effect ** at 50 and 100 μM | — |
| 5 | ICC$_1$03-L-030-D05- | | C$_{24}$H$_{21}$NO$_4$ | 387.4 | — | +++ | *** | +++ |
| 6 | ICC$_1$28-L-013-B06- | | C$_{17}$H$_{14}$N$_2$O$_5$ | 326.3 | ++++ | + | **** | ++++ |
| 7 | ICC$_1$08-L-006-G06- | | C$_{16}$H$_{12}$N$_2$O$_4$ | 296.27 | — | + | *** | ++ |
| 8 | ICC$_1$08-L-006-G08- | | C$_{16}$H$_{14}$N$_2$O$_2$ | 266.29 | — | — | — | — |
| 9 | ICC$_1$08-L-006-H06- | | C$_{17}$H$_{14}$N$_2$O$_3$ | 294.3 | — | — | — but effect ** at 50 and 100 μM | + |

TABLE I-continued
| 10 | ICC₁08-L-006-H03- | 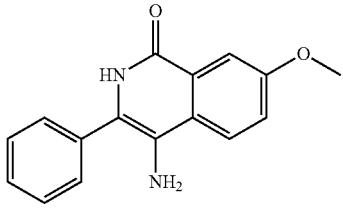 | C₁₆H₁₄N₂O₂ | 266.29 | — | + | — | but effect * at 50 and 100 μM |
| --- | --- | --- | --- | --- | --- | --- | --- | --- |
| 12 | CH1583A | 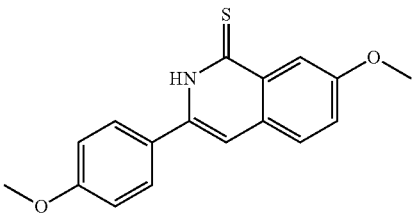 | C₁₇H₁₅NO₂S | 297.37 | ++++ | ++ | — | ++ but effet * to 100 μM |
| 13 | CH1585 | 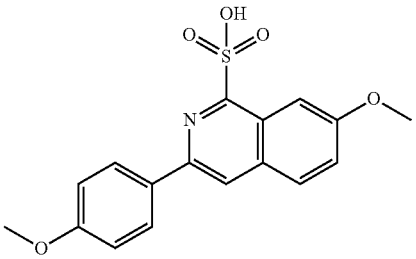 | C₁₇H₁₅NO₅S | 345.37 | — | ++ | — | but effect * at 100 μM |
| 14 | CH1587A | 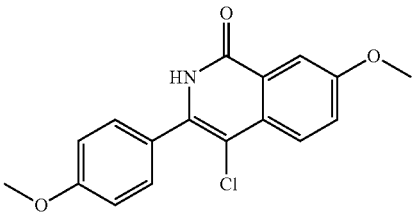 | C₁₇H₁₄CLNO₃ | 315.75 | — | +++ | — | + |
| 15 | CH1584A | 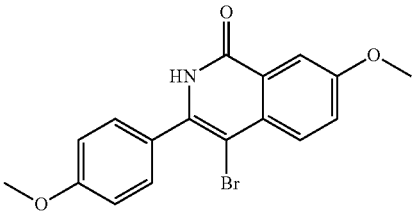 | C₁₇H₁₄BrNO₃ | 360.2 | — | ++ | *** | +++ |
| 16 | CH1586 | 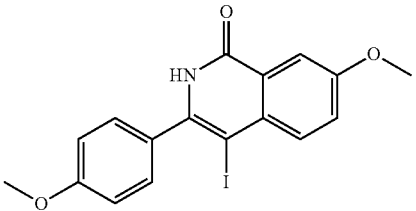 | C₁₇H₁₄INO₃ | 407.2 | — | +++ | *** | +++ |
| 17 | CH1576 | 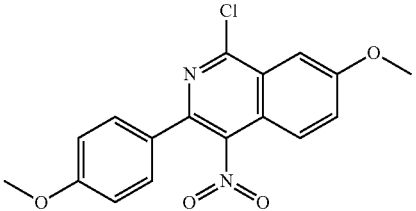 | C₁₇H₁₃ClN₂O₄ | 344.75 | — | ++ | — | + |

TABLE I-continued
| | | | | | | | | |
|---|---|---|---|---|---|---|---|---|
| 18 | CH1590 | 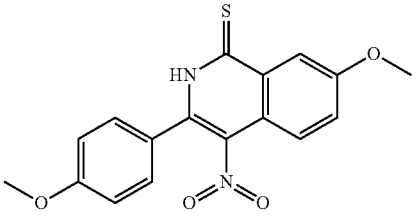 | C$_{17}$H$_{14}$N$_2$O$_4$S | 342.4 | +++ | +++ | **** | ++ |
| 19 | CH1577 | 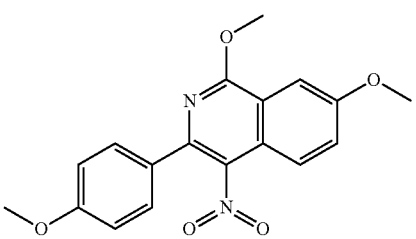 | C$_{18}$H$_{16}$N$_2$O$_5$ | 340.33 | ++ | + | — but effect ** at 100 µM | — |
| 20 | CH1591 | 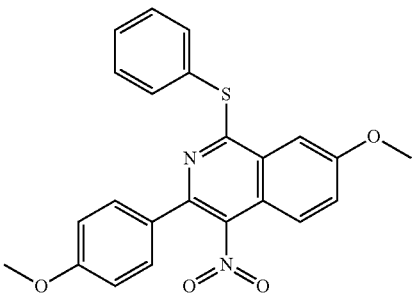 | C$_{23}$H$_{18}$N$_2$O$_4$S | 418.46 | ++ | ++ | — but effect * at 50 and 100 µM | — |
| 21 | CH1592 | 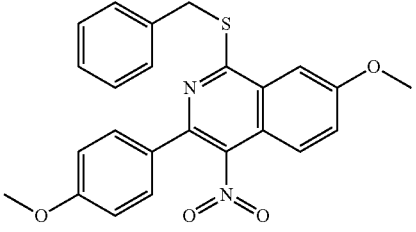 | C$_{24}$H$_{20}$N$_2$O$_4$S | 432.49 | ++ | +++ | — | — |
| 22 | CH1594 | 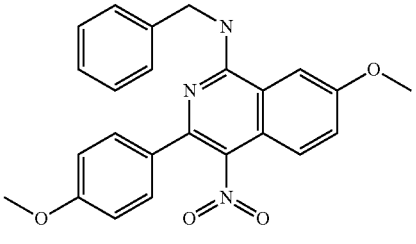 | C$_{24}$H$_{21}$N$_3$O$_4$ | 415.44 | ++++ | + | — | — |
| 23 | DN78-2 | 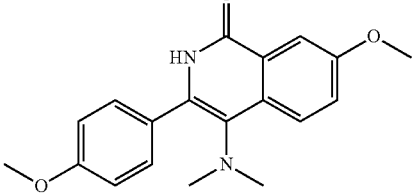 | C$_{19}$H$_{20}$N$_2$O$_3$ | 324.37 | — | + | *** | ++ |

TABLE I-continued

| | | | | | | | | |
|---|---|---|---|---|---|---|---|---|
| 24 | DN86 | (structure) | $C_{18}H_{16}N_2O_4$ | 324.33 | — | + | **** | ++ |
| 25 | DN77-1 | (structure) | $C_{18}H_{15}NO_4$ | 309.3 | + | +++ | **** | +++ |
| 26 | PJ23 | (structure) | $C_{17}H_{13}BrClNO_2$ | 378.65 | — | — | — | — |
| 27 | PJ24 | (structure) | $C_{18}H_{16}BrNO_3$ | 374.23 | — | + | — | + |
| 28 | PJ38f2 | (structure) | $C_{20}H_{16}N_2O_5$ | 364.35 | ++ | — | — | — but effect ** at 50 and 100 μM |
| 29 | PJ38f1 | (structure) | $C_{20}H_{16}N_2O_5$ | 364.35 | + | + | — | — |
| 30 | PJ46f2 | (structure) | $C_{19}H_{15}N_3O_5$ | 365.34 | + | + | — | — |

TABLE I-continued

| | | | | | | | | |
|---|---|---|---|---|---|---|---|---|
| 31 | PJ46f1 | | $C_{19}H_{15}N_3O_5$ | 365.34 | — | ++ | — | — |
| 32 | PJ37 | | $C_{16}H_{12}BrNO_2$ | 330.18 | +++ | — | **** | +++ |
| 33 | PJ39 | | $C_{21}H_{21}NO_2Si$ | 347.48 | — | — | — | + |
| 34 | PJ47 | | $C_{16}H_{11}BrN_2O_4$ | 375.17 | ++ | +++ | *** | ++++ |
| 35 | PJ54 | | $C_{21}H_{20}N_2O_4Si$ | 392.48 | +++ | — | *** | ++++ |
| 36 | PJ56 | | $C_{18}H_{12}N_2O_4$ | 320.30 | +++ | +++ | **** | ++++ |

TABLE I-continued
| 37 | CLG1963 | 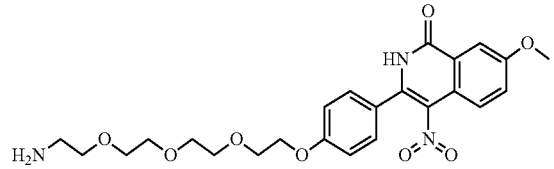 [SMILES: COc1ccc2c([N+](=O)[O-])c(-c3ccc(OCCOCCOCCOCCN)cc3)[nH]c(=O)c2c1] | $C_{24}H_{29}N_3O_8$ | 487.5 | — | — | — | + |
| 38 | PJ-58 | 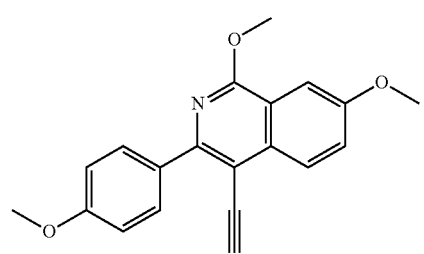 | $C_{20}H_{17}NO_3$ | 319.35 | — | + | — | — |
| 39 | DN103-1 | 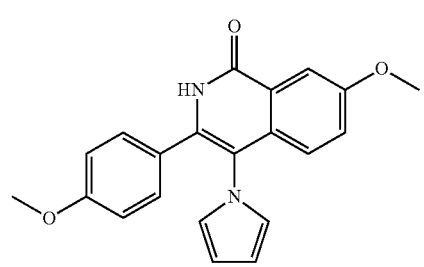 | $C_{21}H_{18}N_2O_3$ | 346.38 | +++ | + | — | +++ |
| 40 | DN114 | 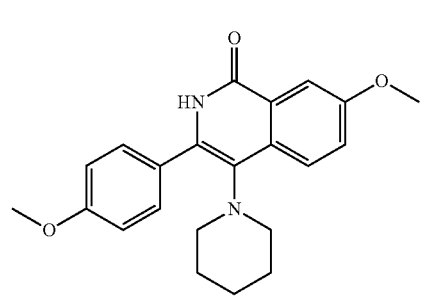 | $C_{22}H_{24}N_2O_3$ | 364.43 | — | +++ | — | +++ |
| 41 | DN122 | 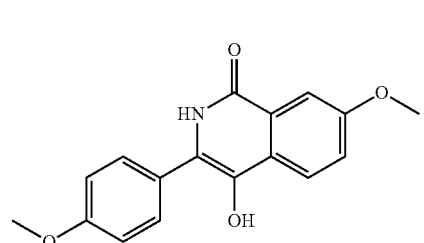 | $C_{17}H_{15}NO_4$ | 297.31 | — | — | — | ++ |
| 44 | CLG 1929 | 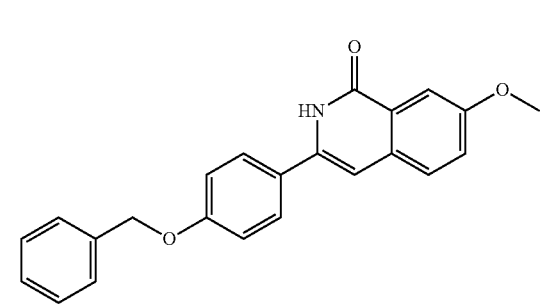 [SMILES: COc1ccc2cc(-c3ccc(OCc4ccccc4)cc3)[nH]c(=O)c2c1] | $C_{23}H_{19}NO_3$ | 357.4 | +++ | — | — | + |

TABLE I-continued

| No. | Code | Structure | Molecular formula | MW | Inhibition PP1 IC50 | Tubulin polymerization inhibition | Effect on Hela at 25 μM | GI50 on HMEC |
|---|---|---|---|---|---|---|---|---|
| 45 | CLG 1930 | | $C_{16}H_{13}NO_3$ | 267.28 | — | ++ | **** | +++ |
| 46 | CLG 1939 | | $C_{23}H_{18}N_2O_5$ | 402.40 | +++ | + | — | — |
| 48 | DN141-2 | 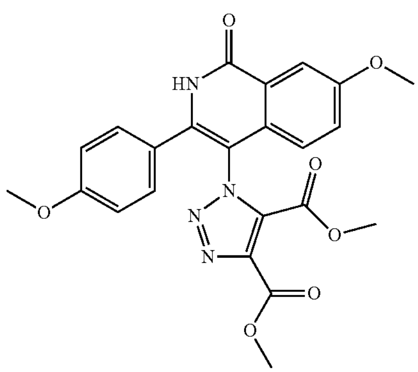 | $C_{23}H_{20}N_4O_7$ | 464.42 | — | — | — but effect * at 50 μM | + |
| 49 | DN145-1 | 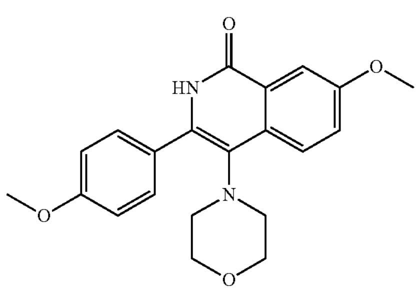 | $C_{21}H_{22}N_2O_4$ | 366.4 | — | + | ** | +++ |
| 50 | DN145-3 | 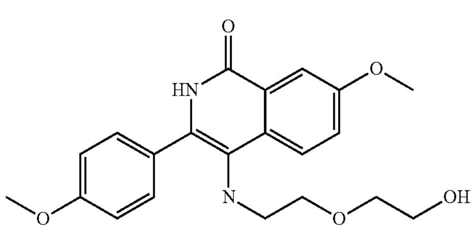 [SMILES: COc1ccc(-c2[nH]c(=O)c3cc(OC)ccc3c2NCCOCCO)cc1] | $C_{21}H_{24}N_2O_5$ | 384.42 | — | +++ | — | + |

TABLE I-continued
| 56 | DN 174-2 | 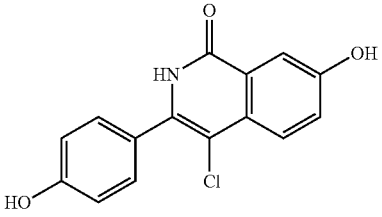 [SMILES: O=c1[nH]c(-c2ccc(O)cc2)c(Cl)c2ccc(O)cc12] | C₁₅H₁₀ClNO₃ | 287.7 | +++ | — | — but effect * at 100 μM | — |
| 57 | DN 171 | 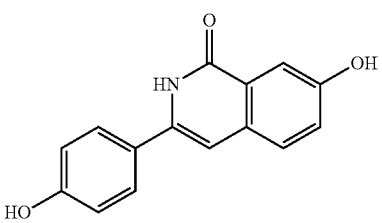 [SMILES: O=c1[nH]c(-c2ccc(O)cc2)cc2ccc(O)cc12] | C₁₅H₁₁NO₃ | 253.25 | — | + | *** | ++ |
| 59 | ADV 1-116 | 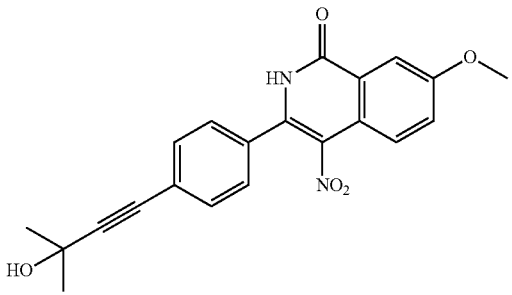 [SMILES: COc1ccc2c([N+](=O)[O-])c(-c3ccc(C#CC(C)(C)O)cc3)[nH]c(=O)c2c1] | C₂₁H₁₈N₂O₅ | 378.38 | ++ | — | — | — |
| 60 | ADV 1-112 | 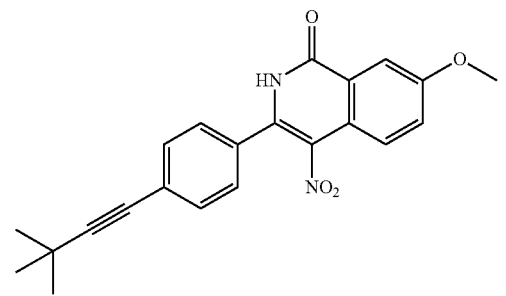 [SMILES: COc1ccc2c([N+](=O)[O-])c(-c3ccc(C#CC(C)(C)C)cc3)[nH]c(=O)c2c1] | C₂₂H₂₀N₂O₄ | 376.41 | ++++ | — | *** | ++ |
| 61 | DN228-1 | 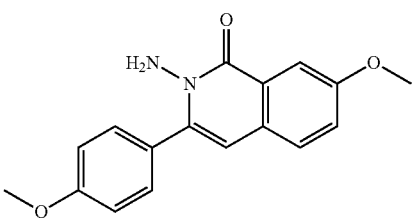 | C₁₇H₁₆N₂O₃ | 296.12 | — | — | — | — |
| 62 | DN282 | 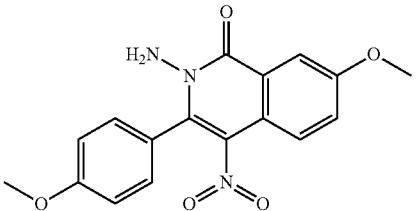 | C₁₇H₁₅N₃O₅ | 341.10 | — | — | *** | ++ |

TABLE I-continued
| 64 | DN263-1 | 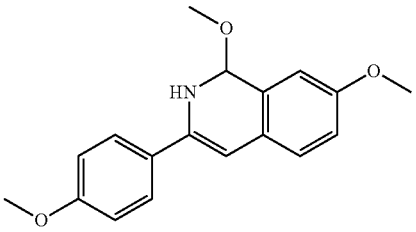 | C₁₈H₁₉NO₃ | 297.36 | +++ | — | — | — |
| 65 | DN263-2 | 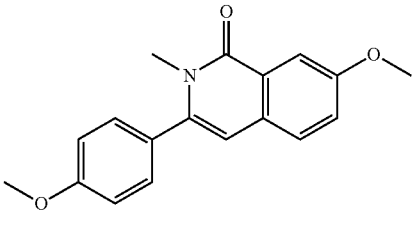 | C₁₈H₁₇NO₃ | 295.12 | + | + | * | ++ |
| 66 | DN264 | 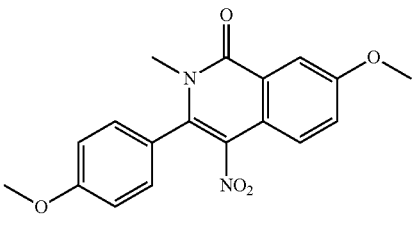 | C₁₈H₁₆N₂O₅ | 340.11 | ++++ | + | * | ++ |
| 67 | DN267 | 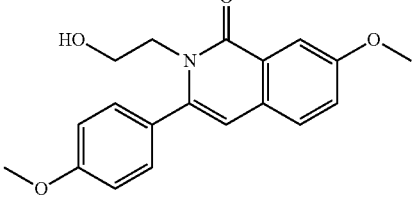 | C₁₉H₁₉NO₄ | 325.13 | ++ | — | — | + |
| 68 | DN281-2 | 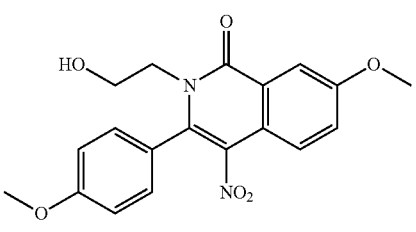 | C₁₉H₁₈N₂O₆ | 370.12 | — | — | — | + |
| 69 | DN274 | 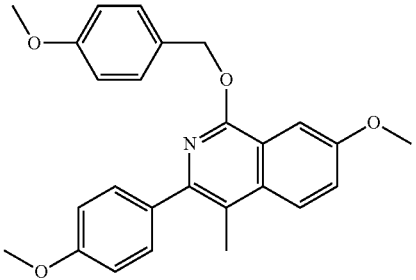 | C₂₅H₂₂INO₄ | 527.06 | ++ | + | — | + |

TABLE I-continued

| | | | Formula | MW | 1 | 2 | | |
|---|---|---|---|---|---|---|---|---|
| 70 | DN279 | [structure] | C₂₆H₂₂F₃NO₄ | 469.15 | +++ | + | — | + |
| 71 | DN278 | [structure] | C₁₇H₁₅N₃O₄ | 325.11 | — | + | — | + |
| 72 | ADV2-029 | [structure] | C₁₆H₁₂N₂O₅ | 312.28 | +++ | ++ | **** | +++ |
| 73 | ADV2-046 | [structure] | C₂₁H₂₀N₂O₇ | 412.39 | +++ | — | *** | ++ |
| 74 | ADV2-035 | [structure] | C₂₃H₁₈N₂O₆ | 418.39 | +++ | + | — | + but effect * at 50 μM |

N.B.: MA: Mitotic arrest; PHF: Primary human fibroblasts; MTs: Microtubules

1. Effect on the activity of PP1CA in vitro

Determination of the 1050 was carried out with PP1CA at 80 mU in the presence of a fluorescent substrate (50 μM) and different concentrations of molecules from 50 μM to 50 nM.

(−) no PP1 inhibiting activity even at 50 μM.

(+) weak PP1 inhibition: 1050≥50 μM.

(++) moderate PP1 inhibition: 1050 between 25 and 50 μM.

(+++) pronounced PP1 inhibition: 1050 between 10 and 24 μM.

(++++) strong PP1 inhibition: 1050≤9 μM.

NT: molecule not tested

2. Effect on Tubulin Polymerization In Vitro

Measurement of the effect of a molecule on polymerization was calculated at t=3000 s taking the value of the control at the same time as being equal to 100%.

(−) signifies that the molecule induces little or no tubulin assembly inhibition in vitro: 0+ or − −5% of the DMSO control.

(+) signifies that the molecule induces tubulin assembly inhibition in vitro comprised between 6 and 25% of the DMSO control.

(++) signifies that the molecule induces tubulin assembly inhibition in vitro comprised between 26 and 50% of the DMSO control.

(+++) signifies that the molecule induces tubulin assembly inhibition in vitro of more than 50% with respect to the DMSO control.

NT: molecule not tested.

3. Effect on HeLa Cells

The mitotic index and/or the depolymerization of the MTs were evaluated at 25 µM.

−: no activity on the cells at 25 µM (if there is an effect at high concentrations, this is specified in the table).

*: weak activity (MA and/or slight depolymerization of the MTs and/or slight inhibition of proliferation),

**: average activity (MA and/or moderate depolymerization of the MTs and/or moderate inhibition of proliferation),

***: strong activity (MA and/or pronounced depolymerization of the MTs and/or pronounced inhibition of proliferation),

****: very strong activity (MA and/or very pronounced depolymerization of the MTs and/or strong inhibition of proliferation).

NT: molecule not tested.

4. GI50 on the HMEC Cells

The HMECs were seeded at 10% confluence and incubated with the molecules at different concentrations (from 50 µM to 1 nM) for 5 days. The GI50 (50% Growth Inhibition) defines the concentration inducing a 50% reduction in proliferation with respect to the control.

(−) no inhibitory activity on the cells at 50 µM.

(+) slight inhibition of proliferation: GI50 between 25 and 50 µM.

(++) moderate inhibition of proliferation: GI50 between 1 and 25 µM.

(+++) pronounced inhibition of proliferation: IC50 between 0.1 and 1 µM.

(++++) strong inhibition of proliferation: IC50≤0.1 µM.

NT: molecule not tested.

Example 8

Affinity Chromatography and Immunoblotting

The molecule 37 was immobilized on a sepharose resin activated by an N-hydroxysuccinimide (NHS) group (GE Healthcare #17-0906-01) as follows: 100 µg of the molecule 37 per ml of NHS Sepharose in PBS, pH 8.3, for 1 hour at ambient temperature. The sepharose coupled with molecule 37 was designated "compound 6" resin, whereas in parallel, another "control" resin was produced with incubation in 0.5 M Monoethanolamine (MEA), pH 8.3, under the same conditions, in order to neutralize the NHS functions. After several washings with PBS, pH 8.3, the NHS functions remaining free were blocked with 0.5 M MEA for 30 minutes. Once they had been thoroughly washed with PBS, the "control" and "compound 6" resins were incubated with 1 ml of *Xenopus* egg extracts diluted 1:1 in CSF-XB buffer containing protease inhibitors (#1 873 580 Roche®), for 1 hour under stirring at 4° C. After 2 washings with PBST, the proteins of the extract remaining attached were eluted with 100 µl of electrophoresis SDS charge buffer (Laemmli, U.K., Cleavage of structural proteins during the assembly of the head of bacteriophage T4. Nature 1970; 227, 680-685) enriched with 6M urea. The samples thus denatured were resolved on a polyacrylamide gel (gradient from 6 to 18%), then transferred onto a nitrocellulose membrane.

Immunodetection was carried out using mouse anti-PP1 (Sigma #7979) or rabbit anti-PP2A (Upstate #07-324) antibodies at a dilution of 1:1000, and the corresponding secondary antibodies coupled with an HRP0 antibody (1:5000, goat anti-mouse IgG, Sigma #A3683; goat anti-rabbit IgG, Sigma #A0545).

In order to detect the HRPO signal a Amersham ECL plus kit (GE Healthcare # RPN2132) was used.

Example 9

Protein Phosphatase Test

For the activity tests, PP1α (New England Biolabs # P0754) was used at a final concentration of 30 mU or 80 mU for the screening of all the analogues. 6,8-difluoro-4-methylumbelliferyl phosphate (DiFMUP, Invitrogen # D6567) was used as fluorescent substrate at a concentration of 60 µM. All the tests were carried out in a final volume of 100 µl, at 37° C. in 96-microwell plates (Greiner #655096).

Compound 6, combretastatin A4 (CA-4) as well as all the analogues were diluted in 50 µl of PP1 buffer (100 mM Tris-HCl, pH 7.5, 4 mM DTT, 0.2 mM EDTA, 0.5 mM $MnCl_2$) from 50 µM to 50 nM. Corresponding quantities of DMSO were added to control wells. PP1α (30 or 80 mU in 30 µl of PP1 buffer) was added to each well. After incubating for 15 minutes at AT, the substrate was added (in 20 µl of PP1 buffer). After incubating for 20 minutes at 37° C., the fluorescence was measured in a plate fluorometer at 355-460 nm in order to assay the phosphatase activity. The test was carried out three times in duplicate for each condition.

Example 10

In Vivo Experiments

All the animal experiments were carried out according to the recommendations of the local ethics commmittee. Nude mice (NCr-nu/nu females (Harlan Laboratories), were housed in a room with filtered air at 22° C., alternating 12 hours of day and 12 hours of night.

HTB177 cells ($1 \times 10^6$) were implanted sub-cutaneously in the flanks of the mice. The tumour growth was monitored twice weekly by measuring the size of the tumours with a slide caliper, thus making it possible to estimate the volume of the tumour, calculated in $mm^3$ according to the following formula: length×width×height×π/6.

Treatment commenced when the tumours reached a size of approximately 250 $mm^3$. The weight of the animal, the volume of the tumour and the extension of the necroses were measured twice weekly.

The animals were sacrificed when the tumour reached 2000 $mm^3$ or sooner if a clinical sign of suffering, defined by the ethics committee, was observed.

The mice received compound 6 per os in doses and at intervals described in the captions to the figures. The control mice received the vehicle alone (identical volume of beta-cyclodextrin at 60 mg/ml))

Example 11

Histology

After euthanasia of the animals, the tumours were removed, cut sagittally along the median line, frozen rapidly in nitrogen liquid and stored at −80° C.

Tumour sections (10 µm in thickness) were produced, then stained with haematoxylin-eosin (H&E) following standard procedures.

Images of the tumour sections were produced under an optical microscope (×10 objective) with an Olympus BX41 camera.

Example 12

Comparative Tests with $INH_2BP$

The produced compound 5-iodo-6-amino-1,2-benzopyrone ($INH_2BP$) described in Patent Application WO 98/51307 exhibits no antiproliferative activity at 50 µM on HeLa cells.

Example 13

Synthesis of the Molecules

Compounds 1, 2, 4, 6 to 8 and 10 were synthesized according to Bisagni et al., Tetrahedron, 1996, 52, 10427-10440.

Compound 5 was synthesized according to Croisy-Delsey et al., Bioorg. Med. Chem., 200, 8, 2629-2641.

The compounds of general formula IIa can be synthesized as follows:
General protocol:
for X=O, the synthesis method is carried out according to Bisagni et al., Tetrahedron 1996, 52, 10427-10440 and comprises the following main stages:
  a) condensation of an arylacetic acid with an arylcarboxaldehyde in order to form an intermediate 2,3-diarylacrylic acid,
  b) conversion of the acid group to the corresponding azide by $NaN_3$ via a mixed anhydride,
  c) cyclization of the azide by thermal route in order to produce 3-arylisoquinolin-1(2H)-one,
  d) arrangement of the functional groups according to the protocols detailed below.
for X=S, the synthesis comprises the following stages
  a) starting from 3-arylisoquinolin-1(2H)-one, the synthesis of isoquinolin-1(2H)-thione is carried out with Lawesson's reagent,
  b) starting from 3-aryl-4-nitroisoquinolin-1(2H)-one, the isoquinolin-1(2H)-thione synthesis method comprises the following main stages:
    chlorination with phosphorus chloride oxide or Vilsmeier reagent in order to form the 1-chloroisoquinoline intermediate,
    conversion of the chloro group to a thione group with thiourea.

The compounds of general formula IIb can be synthesized as follows:
General Protocol:
starting from 3-arylisoquinolin-1(2H)-one: the synthesis of isoquinoline IIb is carried out with the desired haloalkyl in the presence of a base such as $K_2CO_3$,
starting from 1-chloro-4-nitroisoquinoline the synthesis of which was mentioned above: the synthesis of isoquinoline IIb is carried out with the desired nucleophile in basic medium.

Compound 9: N-(7-Methoxy-1-oxo-3-phenyl-1,2-dihydroisoquinoline-4-yl)methanamide A solution of formic acid (2.40 mL; 63 mmol) and compound 10 (500 mg, 1.88 mmol) in toluene (50 mL) is heated under reflux for 5 hours and the liquid is evaporated to dryness under reduced pressure. The residue is then triturated in the mixture of formic acid and water (80/20), then left to cool down in order to produce the expected compound 9 (450 mg; 77%) in the form of pale pink microcrystals; $^1H$ NMR ($CDCl_3$): 3.90 (3H, s), 7.39 (1H, dd), 7.42-7.5 (5H, m), 7.52 (1H, d), 7.67 (1H, d), 8.18 (1H, s), 9.43 (1H, br s), 11.51 (1H, br s); Anal. Cal. for $C_{17}H_{14}N_2O_3.0.17HCO_2H$: C, 68.47; H, 4.76; N, 9.30. Found: C, 68.43; H, 4.89; N, 9.35.

Compound 12: 7-Methoxy-3-(4-methoxyphenyl)isoquinoline-1(2H)-thione

Lawesson's reagent (975 mg, 2.4 mmol) is added under an argon atmosphere to a suspension of lactame 4 (584 mg, 2.1 mmol) in anhydrous toluene (25 mL) at 85° C. The reaction mixture is stirred at this temperature for 20 hours. Water (150 mL) is added and the mixture is extracted with ethyl acetate (2×150 mL). The organic phase is washed with salt water (2×150 mL), dried over $MgSO_4$ and the solid residue obtained after the evaporation of the solvent is recrystallized from absolute ethanol in order to produce the compound thiolactame 12 in the form of bright yellow needles (550 mg, 89%), mp 188-190° C.; $^1H$ NMR (DMSO-$d_6$) 13.21 (1H, br s), 8.21 (1H, d), 7.80-7.70 (3H, m), 7.45 (1H, dd), 7.30 (1H, s), 7.06 (2H, d), 3.91 (3H, s), 3.83 (3H, s); MS 298 (M+H); Anal. Cal. for $C_{17}H_{15}NO_2S.0.5H_2O$: C, 66.66; H, 5.22; N, 4.57. Found: C, 66.31; H, 4.87; N, 5.05.

Compound 13: 7-methoxy-3-(4-methoxyphenyl)isoquinoline-1-sulphonic acid

A solution of nitric acid (d 1.33; 146 µL) in AcOH (650 µL) is added dropwise to a suspension of thiolactame 12 (275 mg, 0.9 mmol) in AcOH (4.3 mL) and AcOEt (1.2 mL) at 0° C. The mixture is then left to return to ambient temperature and stirring is maintained for another hour before water (30 mL) is added to it. The precipitate is filtered, washed with water, dried, then chromatographed on a silica gel column using $CH_2Cl_2$ as eluent in order to produce compound 13 in the form of pale yellow microcrystals (180 mg; 56%), mp 226-228° C.; $^1H$ NMR (DMSO-$d_6$) 8.14 (1H, s), 8.00 (1H, d), 7.83 (2H, d), 7.68 (1H, d), 7.54 (1H, dd), 6.72 (2H, d), 3.97 (3H, s), 3.71 (3H, s); MS 344 (M−H).

Compound 14: 4-Chloro-7-methoxy-3-(4-methoxyphenyl)isoquinoline-1(2H)-one

At ambient temperature, N-chlorosuccinimide (67 mg; 0.5 mmol) is added in one go to a solution of lactame 4 (128 mg, 0.45 mmol) dissolved in AcOH (1.2 mL) and AcOEt (1.2 mL). The reaction mixture is stirred for 24 hours and a new portion of N-chlorosuccinimide (67 mg; 0.5 mmol) is added. Once again the reaction mixture is stirred for 24 hours, then water (10 mL) is added and the precipitate formed is filtered, washed with water and dried. It is then chromatographed on a silica gel column using a gradient of ethanol (0 to 1.5%) in $CH_2Cl_2$ as eluent in order to produce the expected compound 14 (140 mg; 97%) in the form of pale yellow gum; $^1H$ NMR ($CDCl_3$) 7.96 (1H, d), 7.75 (1H, d), 7.51 (2H, d), 7.17 (1H, dd), 6.85 (2H, d), 6.66 (1H, br s), 3.98 (3H, s), 3.77 (3H, s); MS 316 and 318 (M+H).

Compound 15: 4-Bromo-7-methoxy-3-(4-methoxyphenyl)isoquinoline-1(2H)-one

At ambient temperature, N-bromosuccinimide (92 mg; 0.5 mmol) is added in one go to a solution of lactame 4 (108 mg, 0.38 mmol) dissolved in AcOH (1.0 mL) and AcOEt (1.0 mL). The reaction mixture is stirred for 4 hours, water (10 mL) is added and the precipitate formed is filtered, washed with water and dried. It is then chromatographed on a neutral alumina gel column using a gradient of ethanol (0 to 1%) in $CH_2Cl_2$ as eluent in order to produce the expected compound 15 (80 mg; 58%) in the form of white microcrystals, mp 240-242° C.; $^1H$ NMR (DMSO-$d_6$) 11.72 (1H, br s), 7.89 (1H, d), 7.70 (1H, d), 7.50-7.43 (3H, m), 7.05 (2H, d), 3.91 (3H, s), 3.83 (3H, s); MS 359 and 361 (M+H)); Anal. Cal. for $C_{17}H_{14}BrNO_3$: C, 56.69; H, 3.92; N, 3.89; trouve: C, 56.58; H, 3.92; N, 3.66.

Compound 16: 4-Iodo-7-methoxy-3-(4-methoxyphenyl)isoquinoline-1(2H)-one

At ambient temperature, N-iodosuccinimide (127 mg; 0.5 mmol) is added in one go to a solution of lactame 4 (130 mg, 0.46 mmol) dissolved in AcOH (1.2 mL) and AcOEt (1.2 mL). The reaction mixture is stirred for 2.5 hours, water (10 mL) is added and the precipitate formed is filtered, washed with water and dried. It is then chromatographed on a neutral alumina gel column using a gradient of ethanol (0 to 1%) in $CH_2Cl_2$ as eluent in order to produce the expected compound 16 (130 mg; 69%) in the form of white microcrystals, mp 216-218° C.; $^1H$ NMR (DMSO-$d_6$) 11.72 (1H, br s), 7.89 (1H, d), 7.70 (1H, d), 7.50-7.43 (3H, m), 7.05 (2H, d), 3.91 (3H, s), 3.83 (3H, s); MS 408 (M+H); Anal. Cal for $C_{17}H_{14}BINO_3$: C, 50.14; H, 3.47; N, 3.44. Found: C, 50.32; H, 3.48; N, 3.45.

Compound 17: 1-Chloro-7-methoxy-3-(4-methoxyphenyl)-4-nitroisoquinoline

Under an argon atmosphere, phosphorus chloride oxide (3.2 mL) is added in one go to a solution of nitrolactame 6 (1.33 g, 40 mmol) and benzyltriethylammonium chloride in acetonitrile (27 mL). The reaction mixture is then heated under reflux for 3 hours then evaporated under reduced pressure. Cold water (50 mL) is added and the pH is adjusted to 7-8 with 14% $NH_4OH$. The precipitate formed is filtered, washed with water, dried and chromatographed on a silica gel column using $CH_2Cl_2$/acetone: 8-2 as eluent in order to produce the expected compound 17 (1.18 g; 83%) in the form of bright yellow flakes, mp 196-198° C.; $^1H$ NMR (CDCl$_3$) 7.71 (1H, d), 7.70-7.64 (2H, m), 7.63 (1H, d), 7.53 (1H, dd), 7.00 (2H, d), 4.03 (3H, s), 3.86 (3H, s); MS 345 and 347 (M+H) Anal. Cal. for $C_{17}H_{13}ClN_2O_4$: C, 59.23; H, 3.80; N, 8.13. Found: C, 59.17; H, 3.75; N, 7.88.

Compound 18: 7-Methoxy-3-(4-methoxyphenyl)-4-nitroisoquinoline-1(2H)-thione

Under an argon atmosphere, the mixture formed by the chloronitro derivative 17 (230 mg, 0.66 mmol), thiourea (164 mg, 2.1 mmol) and absolute ethanol (7 mL) is heated under reflux for 4 hours. The precipitate formed is filtered, washed with ethanol, dried and chromatographed on a neutral alumina gel column using $CH_2Cl_2$ as eluent in order to produce the expected compound 18 (150 mg; 65%) in the form of pale orange microcrystals, mp 226-228° C.; $^1H$ NMR (DMSO-$d_6$) 13.83 (1H, br s), 8.31 (1H, s), 7.61 (2H, br s), 7.47 (2H, d), 7.07 (2H, d), 7.00 (2H, d), 3.95 (3H, s), 3.83 (3H, s); MS 343 (M+H).) Anal. Cal. for $C_{17}H_{14}N_2O_4S.0.25H_2O$: C, 58.87; H, 4.18; N, 8.08. Found: C, 58.83; H, 4.05; N, 7.94.

Compound 19: 1,7-Dimethoxy-3-(4-methoxyphenyl)-4-nitroisoquinoline

Under an argon atmosphere, the mixture formed by the chloronitro derivative 17 (209 mg, 0.60 mmol), DMF (2 mL) and 30% sodium methoxide solution in methanol (9 mL) is heated under reflux for 18 hours. Cold water (40 mL) is added and the precipitate formed is filtered, washed with water, dried and chromatographed on a silica gel column using $CH_2Cl_2$ as eluent in order to produce the expected compound 19 (158 mg; 76%) in the form of bright yellow flakes, mp 176-178° C.; $^1H$ NMR (CDCl$_3$) 7.70-7.65 (3H, m), 7.57 (1H, d), 7.42 (1H, dd), 6.98 (2H, d), 4.22 (3H, s), 3.97 (3H, s), 3.86 (3H, s); MS 363 (M+Na); Anal. Cal. for $C_{18}H_{16}N_2O_5$: C, 63.52; H, 4.74; N, 8.23. Found: C, 63.46; H, 4.78; N, 7.99.

Compound 20: 7-Methoxy-3-(4-methoxyphenyl)-4-nitro-1-(phenylethio)isoquinoline

Under an argon atmosphere, the mixture formed by the chloronitro derivative 17 (110 mg, 0.32 mmol), absolute ethanol (5 mL), triethylamine (0.1 mL) and thiophenol (70 mg, 0.6 mmol) is heated under reflux for 18 hours. The precipitate formed is filtered, washed with ethanol, dried in order to produce the expected compound 20 (120 mg; 90%) in the form of bright yellow needles, mp 169-171° C.; $^1H$ NMR (CDCl$_3$) 7.70 (1H, d), 7.67-7.62 (2H, m), 7.57 (1H, d), 7.50-7.44 (4H, m), 7.39 (2H, d), 6.82 (2H, d), 4.02 (3H, s), 3.80 (3H, s); MS 419 (M+H); Anal. Cal. for $C_{23}H_{18}N_2O_4S$: C, 66.01; H, 4.34; N, 6.39. Found: C, 65.85; H, 4.15; N, 6.61.

Compound 21: 1-(Benzylthio)-7-methoxy-3-(4-methoxyphenyl)-4-nitroisoquinoline

Under an argon atmosphere, the mixture formed by the chloronitro derivative 17 (138 mg, 0.40 mmol), absolute ethanol (4 mL), triethylamine (0.1 mL) and benzylmercaptan (60 mg, 0.48 mmol) is heated under reflux for 24 hours. The precipitate formed is filtered, washed with ethanol, dried and chromatographed on a silica gel column using $CH_2Cl_2$ as eluent in order to produce the expected compound 21 (120 mg; 69%) in the form of pale orange microcrystals, mp 148-150° C.; $^1H$ NMR (CDCl$_3$) 7.72-7.62 (3H, m), 7.48-7.42 (4H, m), 7.36-7.27 (3H, m), 6.99 (2H, d), 4.68 (2H, s), 3.96 (3H, s), 3.87 (3H, s); MS 433 (M+H); Anal. Cal. for $C_{24}H_{20}N_2O_4S$: C, 66.65; H, 4.66; N, 6.48. Found: C, 66.85; H, 4.58; N, 6.51.

Compound 22: N-Benzyl-N-[7-methoxy-3-(4-methoxyphenyl)-4-nitroisoquinoline-1-yl]-amine Under an argon atmosphere, the mixture formed by the chloronitro derivative 17 (145 mg, 0.42 mmol), absolute ethanol (4 mL), triethylamine (0.1 mL) and benzylamine (136 mg, 1.30 mmol) is heated under reflux for 18 hours. The precipitate formed is filtered, washed with ethanol, dried and chromatographed on a silica gel column using $CH_2Cl_2$ as eluent in order to produce the expected compound 22 (110 mg; 62%) in the form of pale orange microcrystals, mp 199-201° C.; $^1H$ NMR (CDCl$_3$) 7.81 (1H, d), 7.62 (2H, d), 7.47-7.30 (6H, m), 7.02-6.92 (3H, m), 5.75-5.67 (1H, m), 4.93 (2H, d), 3.93 (3H, s), 3.84 (3H, s); MS 414 (M−H); Anal. Cal. for $C_{24}H_{21}N_3O_4.0.25H_2O$: C, 68.65; H, 5.12; N, 10.01. Found: C, 68.59; H, 4.92; N, 9.95.

Compound 23: 4-(Dimethylamino)-7-methoxy-3-(4-methoxyphenyl)isoquinoline-1(2H)-one Cyanoborohydride 126 mg (2.01 mmol) is added to a mixture of 4-amino-7-methoxy-3-(4-methoxyphenyl)isoquinolin-1(2H)-one (compound 1) (200 mg, 0.67 mmol), 37% aqueous formaldehyde (0.54 mL, 6.7 mmol) and acetonitrile (5 mL), at ambient temperature. Glacial acetic acid (116 µL, 2.01 mmol) is then added slowly and the mixture is left under stirring for 5 hours. Again, a second quantity of glacial acetic acid (116 µL, 2.01 mmol) is introduced, stirring is maintained for another 30 minutes then the mixture is evaporated under reduced pressure and ether (15 mL) is added. The ethereal phase is washed successively with a normal solution of KOH (3×30 mL), salt water (3 mL), then dried over $MgSO_4$ and evaporated under reduced pressure. The residue is chromatographed on a silica gel column using a gradient of ethanol (0 to 2%) in $CH_2Cl_2$ as eluent in order to produce the expected compound 23 (54 mg, 25%) in the form of an orange solid, mp 183-185° C.; $^1H$ NMR ($CDCl_3$): 8.30 (1H, br s), 7.85 (1H, d), 7.81 (1H, d), 7.38 (2H, d), 7.33 (1H, dd), 6.99 (2H, d), 3.94 (3H, s), 3.88 (3H, s), 2.64 (6H, s); MS 325 (M+H); Anal. Cal. for $C_{19}H_{20}N_2O_3.1.1H_2O$: C, 66.2; H, 6.44; N, 8.13. Found: C, 66.24; H, 5.81; N, 8.13.

Compound 24: N-(7-Methoxy-3-(4-methoxyphenyl)-1-oxo-1,2-dihydroisoquinoline-4-yl)methanamide Formic acid (1.6 mL) is added to a mixture of 4-amino-7-methoxy-3-(4-methoxyphenyl)isoquinolin-1(2H)-one (compound 1) (100 mg, 0.33 mmol) and ethyl formate (7 mL, previously distilled over calcium hydride) and the mixture is heated under reflux for 12 hours. The mixture is then evaporated to dryness under reduced pressure and the residue obtained is washed with ethanol, filtered, dried under vacuum in order to produce 36 mg of the expected compound 24. The filtrate is concentrated, then chromatographed on a silica gel column using a gradient of ethanol (0 to 5%) in $CH_2Cl_2$ as eluent in order to produce a second fraction of the correct product 24 15 mg (46% overall yield) in the form of white solid, mp>270° C.; $^1H$ NMR ($CDCl_3$): 11.44 (1H, br s), 9.41 (1H, br s), 8.18 (1H, s), 7.65 (1H, s), 7.51 (1H, d), 7.42 (2H, d), 7.38 (1H, dd), 7.00 (2H, d), 3.89 (3H, s), 3.81 (3H, s); MS 347 (M+Na); Anal. Cal. for $C_{18}H_{16}N_2O_4$: C, 66.66; H, 4.97; N, 8.64. Found: C, 66.75; H, 4.92; N, 8.53.

Compound 25: 7-Methoxy-3-(4-methoxyphenyl)isoquinoline-1(2H)-one-4-carbaldehyde

At −78° C., n-BuLi (1.6M in hexane, 1.8 mL, 1.1 mmol) is added to a solution of 4-bromo-7-methoxy-3-(4-methoxyphenyl)isoquinolin-1(2H)-one (compound 15, 200 mg, 0.55 mmol) and THF (10 mL). The yellow suspension obtained is stirred for another 15 minutes at the same temperature then DMF (85 L, 1.1 mmol) is introduced. After 1 hour at −78° C., water (10 mL) is added then the mixture is extracted with dichloromethane (3×10 mL). The combined organic phases are washed with water, dried over $MgSO_4$ and the residue obtained after the evaporation of the solvent is chromatographed on a silica gel column using a gradient of ethanol (0 to 2%) in $CH_2Cl_2$ as eluent in order to produce the expected compound 25 (46 mg, 27%) in the form of a white solid, mp 232° C., $^1H$ NMR ($CDCl_3$): 3.91 (3H, s), 3.95 (3H, s), 7.06 (2H, d), 7.4 (1H, dd), 7.48 (2H, d), 7.81 (1H, d), 8.77 (1H, br s), 9.15 (1H, d), 9.79 (1H, s); MS 310 (M+H); Anal. Cal. for $C_{18}H_{15}NO_4.0.2H_2O$: C, 69.07; H, 4.92; N, 4.47. Found: C, 68.68; H, 4.98; N, 4.34.

Compound 26: 4-Bromo-1-chloro-7-methoxy-3-(4-methoxyphenyl)isoquinoline

A suspension of Vilsmeier reagent (1.7 g, 13.2 mmol) in 13 mL of dichloroethane is stirred for a few minutes then the compound 4-bromo-7-methoxy-3-(4-methoxyphenyl)isoquinolin-1(2H)-one (2.1 g, 6 mmol) is added. The mixture is taken to reflux, then, after one hour, left to return to ambient temperature. The solution is then diluted in 750 mL of chloroform and washed with 3×200 mL of water. The organic phase is dried over $MgSO_4$, filtered and evaporated under reduced pressure. The white solid obtained is crystallized from methanol. The expected compound 26 is obtained in the form of white crystals (1.78 g, 95%), mp 164-166° C., MS 378 [M+H]+, $^1H$ NMR ($CDCl_3$): 3.86 (s, 3H), 4.00 (s, 3H), 6.95-7.02 (m, 2H), 7.47 (dd, J=2.6 and J=9.2 Hz, 1H), 7.54 (d, J=2.5 Hz, 1H), 7.65-7.70 (m, 2H), 8.24 (d, J=9.3 Hz, 1H); $^{13}C$ NMR ($CDCl_3$): δ5.4, 55.8, 104.2, 113.4, 117.0, 125.2, 127.7, 129.3, 131.4, 131.8, 133.0, 148.0, 148.5, 159.7, 159.8.

Compound 27: 4-Bromo-1,7-Dimethoxy-3-(4-methoxyphenyl)isoquinoline

Sodium methylate (1.26 g, 23.5 mmol) is added to a suspension of the compound 4-bromo-1-chloro-7-methoxy-3-(4-methoxyphenyl)isoquinoline 26 (1.78 g, 4.7 mmol) in 70 mL of methanol. The reaction mixture is taken to reflux for 2 days. Then the solvent is evaporated off, the reaction crude is redissolved in 100 mL of water and extracted with 300 mL of chloroform. The organic phase is dried over $MgSO_4$, filtered and concentrated under reduced pressure. The white solid obtained is purified by chromatography on a silica column ($CH_2Cl_2$/Cyclohexane 1/1 then 7/3). The expected compound 27 is obtained in the form of a white powder (1.55 g, 88%), mp 138-140° C., MS 375 and 377 [M+H]+, $^1H$ NMR ($CDCl_3$): 3.89 (s, 3H), 3.97 (s, 3H), 4.13 (s, 3H), 6.97-7.04 (m, 2H), 7.39 (dd, J=2.7 and J=9.2 Hz, 1H), 7.53 (d, J=2.6 Hz, 1H), 7.74-7.81 (m, 2H), 8.15 (d, J=9.2 Hz, 1H); $^{13}C$ NMR ($CDCl_3$, 300 MHz): 53.8, 55.2, 55.5, 102.4, 109.3, 113.0, 120.5, 123.4, 128.4, 131.4, 132.5, 133.1, 145.8, 158.2, 158.4, 159.3.

Compound 28: 7-Methoxy-3-(4-methoxyphenyl)-4-nitro-2-(propargyl)isoquinolin-1(2H)-one A mixture of compound 6 (1.36 g, 4.17 mmol), $K_2CO_3$ (576 mg, 4.17 mmol) in 42 mL of DMF is stirred at ambient temperature for 15 minutes. Then propargyl bromide (450 µL, 4.17 mmol) is added and the solution is stirred at ambient temperature. After 24 hours, 80 mL of water is added and the mixture is extracted with 4×40 mL of ethyl acetate. The organic phases are combined, washed with 2×20 mL of a saturated aqueous solution of NaCl, dried over $MgSO_4$, filtered and concentrated under reduced pressure. The yellow oil obtained is purified by chromatography on a silica column (cyclohexane/ethyl acetate 95/5). 1.1 g (75%) of compound 28 is recovered in the form of a yellow powder: mp 162-164° C.; MS 365 [M+H]+; $^1H$ NMR ($CDCl_3$): 2.24 (t, 1H), 3.87 (s, 3H), 3.95 (s, 3H), 4.55 (d, J=2.4 Hz, 2H), 6.98-7.04 (m, 2H), 7.36 (dd, J=2.7 and J=9.0 Hz, 1H), 7.40-7.47 (m, 3H), 7.90 (d, J=2.7 Hz, 1H); $^{13}C$ NMR ($CDCl_3$, 300 MHz): 36.2, 55.5, 56.0, 72.4, 78.4, 108.8, 114.6, 121.4, 122.7, 123.2, 124, 125.9, 130.9, 134.0, 136.7, 160.1, 160.7, 161.3.

Compound 29: 7-Methoxy-3-(4-methoxyphenyl)-4-nitro-1-(prop-2ynyloxy)isoquinoline This compound is formed at the same time as the compound 7-methoxy-3-(4-methoxyphenyl)-4-nitro-2-(propargyl)isoquinolin-1(2H)-one 28, the preparation of which has already been described above. It is obtained in the form of a yellow-orange solid 29 (228 mg, 11%), mp 177-179° C., by chromatography on a silica column and corresponds to the least polar derivative, MS 365 [M+H]$^+$; $^1$H NMR (CDCl$_3$) 2.55 (t, J=2.4 Hz, 1H), 3.85, 3.96 (2×s, 2×3H), 5.26 (d, J=2.4 Hz, 2H), 6.96-7.02 (m, 2H), 7.42 (dd, J=2.6 and J=9.2 Hz, 1H), 7.56 (d, J=2.6 Hz, 1H), 7.64-7.72 (m, 3H); $^{13}$C NMR (CDCl$_3$): δ4.6, 55.5, 55.9, 75.0, 78.8, 102.8, 114.3, 119.3, 122.8, 125.3, 126.0, 128.5, 129.8, 138.2, 139.9, 157.4, 159.2, 160.7.

Compound 30: 2-(7-Methoxy-3-(4-methoxyphenyl)-4-nitro-1-oxoisoquinolin-2(1H)-yl)ethanenitrile A mixture of compound 6 (1.47 g, 4.5 mmol), K$_2$CO$_3$ (622 mg, 4.5 mmol) in 45 mL of DMF is stirred at ambient temperature for 15 minutes. Then bromoacetonitrile (313 μL, 4.5 mmol) is added and the solution is stirred at ambient temperature. After 3 hours, 100 mL of water is added and the mixture is extracted with 4×100 mL of ethyl acetate. The organic phases are combined, washed with 2×20 mL of a saturated aqueous solution of NaCl, then dried over MgSO$_4$, filtered and concentrated under reduced pressure. The yellow solid obtained is purified by chromatography on a silica column (cyclohexane/ethyl acetate 95/5). 980 mg (60%) of compound 30 is recovered in the form of a yellow powder: mp 194-196° C.; MS 366 [M+H]$^+$; $^1$H NMR (DMSO-d$_6$): 3.85 (s, 3H), 3.95 (s, 3H), 4.65 (s, 2H), 7.14-7.19 (m, 2H), 7.46-7.61 (m, 4H), 7.80 (d, J=2.4 Hz, 1H); $^{13}$C NMR (DMSO, 300 MHz): 34.6, 55.4, 55.9, 108.9, 114.8, 115.6, 120.6, 121.9, 123.3, 124.1, 124.9, 130.9, 133.8, 136.5, 159.7, 159.8, 161.0.

Compound 31: 2-(7-Methoxy-3-(4-methoxyphenyl)-4-nitroisoquinolin-1-yloxy)ethanenitrile This compound is formed at the same time as the compound 2-(7-methoxy-3-(4-methoxyphenyl)-4-nitro-1-oxoisoquinolin-2(1H)-yl)ethanenitrile 30 the synthesis of which was described above. It is obtained in the form of a yellow solid (118 mg, 11%), mp 192-194° C., by chromatography on a silica column and corresponds to the least polar derivative, MS 366 [M+H]$^+$; $^1$H NMR (CDCl$_3$) 3.86 (s, 3H), 3.98 (s, 3H), 5.27 (s, 2H), 6.98-7.02 (m, 2H), 7.46-7.51 (m, 2H), 7.67-7.71 (m, 3H); $^{13}$C NMR (CDCl$_3$): δ1.2, 55.5, 56.0, 102.3, 114.5, 115.4, 118.8, 123.0, 125.9, 126.2, 127.8, 129.8, 138.9, 139.5, 156.0, 159.6, 160.9.

Compound 32: 3-(4-Bromophenyl)-7-methoxyisoquinolin-1(2H)-one

The synthesis of the molecule 32 is carried out according to a protocol described in the literature by Bisagni et al., Tetrahedron 1996, 52, 10427-10440, except that the 4-methoxyphenyl acetic acid is replaced by 4-bromophenyl acetic acid. Compound 32 (7.18 g, 90%) is obtained in the form of a white solid: mp>250° C.; MS 330 and 332 [M+H]$^+$; $^1$H NMR (DMSO-d$_6$): 3.88 (s, 3H), 6.93 (s, 1H), 7.35 (dd, J=2.6 and J=8.6 Hz, 1H), 7.61-7.74 (m, 6H), 11.54 (br s, 1H).

Compound 33: 7-Methoxy-3-(4-((trimethylsilyl)ethynyl)phenyl)isoquinolin-1(2H)-one A mixture of the brominated derivative 32 (1 g, 3.03 mmol), copper iodide (29 mg, 0.15 mmol), Pd(PPh$_3$)$_2$Cl$_2$ (53 mg, 0.076 mmol), and trimethylsilylacetylene (915 μL, 6.1 mmol) in 45 mL of DMF and 12 mL of diisopropylethylamine is stirred under argon at 80° C. for 24 hours. The reaction mixture is filtered on Celite and the filtrate is dissolved in 100 mL of water and 500 mL of ethyl acetate. The organic phase is washed with a saturated aqueous solution of NH$_4$Cl until neutral, dried over MgSO$_4$ and evaporated under reduced pressure. The solid obtained is purified by chromatography on a silica column (cyclohexane/ethyl acetate, 9/1). 400 mg (40%) of the product 33 is recovered in the form of a white powder: mp 133-135° C.; MS 348 [M+H]$^+$; $^1$H NMR (CDCl$_3$, 300 MHz): 0.27 (s, 9H), 3.95 (s, 3H), 6.78 (s, 1H), 7.30 (dd, J=2.7 and J=5.8 Hz, 2H), 7.51-7.67 (m, 5H), 7.80 (d, J=2.6 Hz, 1H), 9.9 (br s, 1H).

Compound 34: 3-(4-Bromophenyl)-7-methoxy-4-nitroisoquinolin-1(2H)-one

A 53% aqueous solution of nitric acid (6 mL, 50 mmol) diluted in 25 mL of ethyl acetate is added to a mixture of compound 32 (4 g, 12.1 mmol) in suspension in 20 mL of ethyl acetate and 40 mL of acetic acid. The suspension is heated at 50° C. for 2 hours. In the presence of 100 mL of water, a precipitate is formed, which is filtered, dried and recrystallized from toluene. 4 g (89%) of compound 34 is obtained in the form of an orange solid: mp 222-224° C.; MS 375 and 377 [M+H]$^+$; $^1$H NMR (DMSO-d$_6$): 3.93 (s, 3H), 7.45-7.55 (m, 3H), 7.67 (d, J=9.0 Hz, 1H), 7.69-7.75 (m, 3H), 10.5 (br s, 1H).

Compound 35: 7-Methoxy-4-nitro-3-(4-((trimethylsilyl)ethynyl)phenyl)isoquinolin-1(2H)-one The preparation of molecule 35 is carried out starting from compound 34 according to the protocol described previously in order to synthesize the molecule 33. Under these conditions, the expected product 35 (2.45 g, 75%) is recovered in the form of a yellow powder: mp 178-180° C.; MS 393 [M+H]$^+$; $^1$H NMR (DMSO, 300 MHz): 0.25 (s, 9H), 3.93 (s, 3H), 7.47-7.6 (m, 5H), 7.65 (d, J=9.1 Hz, 1H), 7.72 (d, J=2.7 Hz, 1H), 12.3 (br s, 1H); $^{13}$C NMR (DMSO-d$_6$): 54.9, 55.7, 92.0, 108.2, 123.2, 123.5, 123.6, 123.9, 125.9, 128.7, 130.0, 131.2, 131.8, 136.9, 159.2, 160.6.

Compound 36: 3-(4-Ethynylphenyl)-7-methoxy-4-nitroisoquinolin-1(2H)-one

Tributylammonium fluoride on silica (5 g, 7.61 mmol) is added to a solution of compound 35 (2 g, 5.1 mmol) in 100 mL of distilled THF. The mixture is stirred at ambient temperature for 4 hours. Then the solution is filtered on Celite and the filtrate is evaporated under reduced pressure. The crude product is then purified by chromatography on a silica column (cyclohexane/ethyl acetate 7/3). Compound 36 is recovered in the form of a yellow powder (1.33 g, 81%): mp 246-248° C.; MS 321 [M+H]$^+$; $^1$H NMR (DMSO-d$_6$): 3.91 (s, 3H), 4.37 (s, 1H), 7.49-7.54 (m, 3H), 7.61 (m, 2H), 7.68 (d, J=9.1 Hz, 1H), 7.72 (d, J=2.8 Hz, 1H), 12.2 (br s, 1H); $^{13}$C NMR (DMSO-d$_6$): 55.7, 82.7, 108.2, 123.1, 123.5, 123.6, 125.9, 128.7, 130.2, 131.2, 132.0, 136.9, 159.1, 160.5.

Compound 37: 3-(4-(2-(2-(2-(2-Aminoethoxy)ethoxy)ethoxy)phenyl)-7-methoxy-4-nitroisoquinolin-1(2H)-one Sodium azide (1.0 g) is added to a solution of tetraethyleneglycol dimethanesulphonate (5.25 g, 15 mmol), obtained according to A. W. Chwabacher et al. (J. Org. Chem. 1998, 65(5), 1717), in 18 mL of 95° ethanol. The reaction mixture is taken to reflux for 24 hours. Then the solvent is evaporated off, the reaction crude is added to 100 mL of salt water and extracted with ether 3×100 mL. The organic phase is dried over MgSO$_4$, filtered and concentrated under reduced pressure. The residue obtained is purified by chromatography on a silica column using a gradient of AcOEt in hexane (1/1 to 3/1) as eluents. 2-(2-(2-(2-azidoethoxy)ethoxy)ethoxy)ethyl mono-methanesulphonate 47 (2.10 g, 47%) is obtained, which is used directly in the following stage.

2-(2-(2-(2-azidoethoxy)ethoxy)ethoxy)ethyl methanesulphonate (175 mg, 0.58 mmol) and $Cs_2CO_3$ (190 mg, 0.58 mmol) are added to the mixture of 3-(4-hydroxyphenyl)-7-methoxyisoquinolin-1(2H)-one (compound 45) (130 mg, 0.48 mmol) in DMF (6 mL). The reaction mixture is heated at 80° C. for 24 hours. Then the solvent is evaporated off, the reaction crude is added to water (100 mL) and extracted with $CH_2Cl_2$ (3×100 mL). The organic phase is dried over $MgSO_4$, filtered and concentrated under reduced pressure. The residue obtained is purified by silica column chromatography using a gradient of EtOH (1 to 3%) in $CH_2Cl_2$ as eluents. Intermediate 3-(4-(2-(2-(2-(2-azidoethoxy)ethoxy)ethoxy)ethoxy)phenyl)-7-methoxyisoquinolin-1(2H)-one (52 mg, 23%) is obtained, which is used directly in the following stage.

Nitration of the compound 3-(4-(2-(2-(2-(2-azidoethoxy)ethoxy)ethoxy)ethoxy)phenyl)-7-methoxyisoquinolin-1(2H)-one, obtained above, is carried out according to the conditions described by E. Bisagni et al. (Tetrahedron, 1996, 52, 10427-10440) and provides the compound 3-(4-(2-(2-(2-(2-azidoethoxy)ethoxy)ethoxy)ethoxy)phenyl)-7-methoxy-4-nitroisoquinolin-1(2H)-one with a yield of 50%, MS 512 $[M-H]^+$; $^1H$ NMR ($CDCl_3$) 8.63 (1H, br s), 7.82 (1H, br s), 7.63 (1H, d), 7.42 (3H, m), 7.03 (2H, d), 4.19 (2H, t), 3.96 (3H, s), 3.89 (2H, t), 3.71 (10H, m), 3.38 (2H, t), Anal. Cal. for $C_{24}H_{27}N_5O_8 \cdot H_2O$, C, 54.23; H, 5.50. Found: C, 54.49; H, 5.21.

At ambient temperature, the mixture of 3-(4-(2-(2-(2-(2-azidoethoxy)ethoxy)ethoxy)ethoxy)phenyl)-7-methoxy-4-nitroisoquinolin-1(2H)-one (56 mg, 0.11 mmol), triphenylphosphine (52 mg) and THF-water (1/4 v/v, 1 mL) is stirred for 4 days. The mixture is evaporated under reduced pressure and the residue obtained is purified by chromatography on a silica column using the $CH_2Cl_2/EtOH/NH_4OH$ mixture 90/10/5 as eluent in order to produce the expected compound 37 (20 mg, 38%), MS 488 (M+H), $^1H$ NMR ($CDCl_3$) 7.75 (1H, d), 7.57 (1H, d), 7.35 (1H, d), 7.30 (1H, dd), 6.98 (1H, d), 4.16 (2H, t), 3.88 (3H, s), 3.81 (2H, t), 3.66 (2H, m), 3.57 (4H, m), 3.48 (2H, m), 3.36 (2H, t), Anal. Cal. for $C_{24}H_{29}N_3O_8 \cdot H_2O$, C, 57.02; H, 6.18. Found: C, 57.41; H, 6.39.

Compound 38: 4-Ethynyl-1,7-dimethoxy-3-(4-methoxyphenyl)isoquinoline

A mixture of the compound 4-bromo-1,7-dimethoxy-3-(4-methoxyphenyl)isoquinoline (compound 26) (187 mg, 0.5 mmol), potassium (trimethylsilyl)ethynyltrifluoroborate (133 mg, 0.65 mmol), palladium diacetate (3.5 mg, 0.015 mmol), RuPhos (14 mg, 0.03 mmol) and potassium carbonate (318 mg, 1.5 mmol) dissolved in 2 mL of a distilled THF/degassed $H_2O$ mixture (10/1) is refluxed under argon for 2 hours. The reaction medium is filtered on silica then condensed under vacuum. The crude is purified on a silica column (cyclohexane/dichloromethane, 7/3). 182 mg (93%) of the 1,7-dimethoxy-3-(4-methoxyphenyl)-4-((trimethylsilyl)ethynyl)isoquinoline intermediate is obtained in the form of a brown solid which is used directly in the following stage, Tributylammonium fluoride adsorbed on silica (450 mg, 0.67 mmol) is added to a solution of 1,7-dimethoxy-3-(4-methoxyphenyl)-4-((trimethylsilyl)ethynyl)isoquinoline (175 mg, 0.447 mmol) in 25 mL of distilled THF. The mixture is stirred at ambient temperature overnight. The reaction solution is filtered on Celite, then the filtrate is concentrated under reduced pressure. The crude is then purified on a silica column (cyclohexane/dichloromethane, 1/1). 133 mg (90%) of the expected compound 38 is obtained in the form of a greyish green powder, mp 209-210° C.; MS 320 $[M+H]^+$; $^1H$ NMR ($CDCl_3$) 3.52 (s, 1H), 3.88 (s, 3H), 3.96 (s, 3H), 4.20 (s, 3H), 7.00 (m, 2H), 7.38 (dd, J=2.7 and J=9.1 Hz, 1H), 7.53 (d, J=2.6 Hz, 1H), 8.14-8.24 (m, 3H); $^{13}C$ NMR ($CDCl_3$) δ3.8, 55.3, 55.6, 80.1, 84.9, 102.5, 104.1, 113.2, 118.6, 123.3, 127.1, 131.0, 132.3, 133.2, 134.3, 150.4, 158.3, 158.7, 160.

Compound 39: 4-(Pyrrol-1-yl)-7-methoxy-3-(4-methoxyphenyl)isoquinoline-1(2H)-one Dimethoxytetrahydrofuran (42 μL, 0.32 mmol) is added, at 0° C. under stirring, to a suspension of 4-amino-7-methoxy-3-(4-methoxyphenyl)isoquinolin-1(2H)-one (compound 1, 80 mg, 0.27 mmol) in HOAc (5 mL) then the mixture is heated under reflux for 2 hours. Water (10 mL) and 14% $NH_4OH$ (2 mL) are introduced into the cooled reaction mixture. The precipitate formed is filtered, washed with water and dried. The filtrate is extracted with $CH_2Cl_2$ then the organic phase is dried over $MgSO_4$ and the residue obtained after evaporation of the solvent is combined with the precipitate obtained previously and the mixture is chromatographed on a silica gel column using a gradient of ethanol (0 to 5%) in $CH_2Cl_2$ as eluent in order to produce the expected compound 39 (26 mg, 28%) in the form of a white solid, mp 238° C., $^1H$ NMR ($CDCl_3$): 9.42 (1H, br s), 7.82 (1H, d, J=3 Hz), 7.25 (1H, dd, J=6 Hz, J=3 Hz), 7.18 (2H, d, J=9 Hz), 7.05 (1H, d, J=9 Hz), 6.85 (2H, d, J=9 Hz), 6.66 (2H, d, J=1.8 Hz), 6.29 (2H, d, J=1.8 Hz), 6.29 (2H, d, J=1.8 Hz), 3.96 (3H, s), 3.81 (3H, s); MS 347 (M+H). Anal. Cal. for $C_{21}H_{18}N_2O_3 \cdot 0.5H_2O$: C, 70.98; H, 5.07; N, 7.88.

Found: C, 70.99; H, 5.41; N, 7.57.

Compound 40: 4-(Piperidin-1-yl)-7-methoxy-3-(4-methoxyphenyl)isoquinoline-1(2H)-one Sodium cyanoborohydride (21 mg, 0.33 mmol) is added slowly to a solution of 4-amino-7-methoxy-3-(4-methoxyphenyl)isoquinolin-1(2H)-one (compound 1, 100 mg, 0.33 mmol) and glutaraldehyde (25% in $H_2O$, 0.377 mL, 0.99 mmol) dissolved in $CH_3CN$ (5 mL). Acetic acid (3 drops) is then introduced and the reaction mixture is left under stirring at ambient temperature for 2 hours before being poured into water (15 mL). The precipitate obtained is filtered, washed with water and dried under vacuum in order to produce the expected compound 40 (80 mg, 66%) in the form of a white solid, mp 206° C.; 1H NMR ($CDCl_3$) 8.16 (1H, br s), 7.95 (1H, d), 7.82 (1H, d), 7.36 (2H, d), 7.34 (1H, dd), 7.01 (2H, d), 3.96 (3H, s), 3.90 (3H, s), MS 387 (M+Na). Anal. Cal. for $C_{21}H_{18}N_2O_3 \cdot 0.5H_2O$: C, 70.77; H, 6.7; N, 7.5. Found: C, 70.63; H, 6.41; N, 7.63.

Compound 41: 4-Hydroxy-7-methoxy-3-(4-methoxyphenyl)isoquinolin-1(2H)-one

At 0° C., a solution of sodium nitrite (24.8 mg, 0.36 mmol) in water (0.5 mL) is added slowly to a solution of 4-amino-7-methoxy-3-(4-methoxyphenyl)isoquinolin-1(2H)-one (100 mg, 0.33 mmol) dissolved in acetic acid (1 mL) and sulphuric acid (0.5 mL). The mixture is left under stirring under cold conditions for 30 minutes then sodium azide (25.7 mg, 0.39 mmol) dissolved in a minimum amount of water (0.2 mL) is introduced slowly. Stirring, still under cold conditions, is maintained for another 3 hours, then water (10 mL) is poured onto the reaction mixture and the solid residue formed is collected by filtration. Silica gel column chromatography using a gradient of ethanol (0 to 2%) in $CH_2Cl_2$ as eluent makes it possible to isolate the compound possessing the greatest mobility which corresponds to the expected compound 41 (31 mg, 31%) in the form of a white solid, $^1H$ NMR ($CDCl_3$) 7.91 (1H, d), 7.74 (1H, d), 7.41 (2H, d), 7.16 (1H, dd), 6.85 (2H, d), 6.75 (1H, br s), 4.60 (1H, br s), 3.98 (3H, s), 3.78 (3H, s); MS 295 (M−2H).

Compound 44: 3-(4-(Benzyloxy)phenyl)-7-methoxy-isoquinolin-1(2H)-one

The synthesis of this compound was carried out according to the method described by E. Bisagni et al. (Tetrahedron, 1996, 52, 10427-10440) in which 4-methoxyphenyl acetic acid is replaced by 4-benzyloxyphenyl acetic acid. However, due to the instability of the intermediate, 2-(4-(benzyloxy)phenyl)-3-(4-methoxyphenyl)prop-2-enoyl azide, the latter is immediately converted to carbamate by heating under reflux in absolute ethanol. The cyclization of ethyl 1-(4-(benzyloxy)phenyl)-2-(4-methoxyphenyl)vinylcarbamate is carried out by heating under reflux in diphenyl ether in the presence of tributyl amine (3%, v/v) for 3.5 hours and provides the expected product 44 with a yield of 51%, mp>260° C., MS 380 [M+Na]$^+$, $^1H$ NMR (DMSO-d$_6$): 11.45 (1H, br s), 7.76 (2H, d), 7.66 (2H, m), 7.42 (6H, m), 7.15 (2H, d), 6.87 (1H, s), 5.22 (2H, s), 3.91 (3H, s), Anal. Cal. for $C_{23}H_{19}NO_3 \cdot \frac{1}{3}H_2O$: C, 76.02; H, 5.45; N, 3.85. Found: C, 76.01; H, 5.47; N, 3.93.

Compound 45: 3-(4-Hydroxyphenyl)-7-methoxyisoquinolin-1(2H)-one

At ambient temperature, a mixture of 3-(4-hydroxyphenyl)-7-methoxyisoquinolin-1(2H)-one 3-(4-(benzyloxy)phenyl)-7-methoxyisoquinolin-1(2H)-one (150 mg, 0.42 mmol), Pd/C (10%, 70 mg) and absolute ethanol (60 mL) is stirred under ordinary hydrogen pressure for 18 hours. The catalyst is then filtered, washed with alcohol, then the solvent is evaporated off under reduced pressure. Ethyl ether (50 mL) is added to the residue, the grey solid is then collected and corresponds to the expected compound 3-(4-hydroxyphenyl)-7-methoxyisoquinolin-1(2H)-one 45 (90 mg, 80%), mp 255° C., $^1H$ NMR (DMSO-d$_6$): 11.36 (1H, br s), 9.88 (1H, br s), 7.68-7.57 (4H, m), 7.36 (1H, dd), 6.88 (2H, d), 6.80 (1H, s), 3.98 (3H, s), 3.90 (3H, s), MS 268 (M+H); Anal. Cal. for $C_{16}H_{13}NO_3 \cdot \frac{1}{3}H_2O$: C, 70.32; H, 5.04; N, 5.13. Found: C, 69.92; H, 4.95; N, 5.09.

Compound 46: 3-(4-(Benzyloxy)phenyl)-7-methoxy-4-nitroisoquinolin-1(2H)-one

The synthesis of this compound is carried out according to the method of nitration described by E. Bisagni et al. (Tetrahedron, 1996, 52, 10427-10440) in which 7-methoxy-3-(4-methoxyphenyl)isoquinolin-1(2H)-one is replaced by 3-(4-(benzyloxy)phenyl)-7-methoxyisoquinolin-1(2H)-one. It is obtained in the form of a yellow powder (yield of 77%), mp 252-254° C., MS 401 [M−H]$^+$; $^1H$ NMR (DMSO-d$_6$): 12.11 (1H, s), 7.75 (1H, d), 7.63 (1H, d), 7.55-7.35 (8H, m), 5.21 (2H, s), 3.36 (3H, s), Anal. Cal. for $C_{23}H_{18}N_2O_5$: C, 68.65; H, 4.51; N, 6.96. Found: C, 68.72; H, 4.49; N, 6.72.

Compound 47: 3-(4-(2-(2-(2-(2-Azidoethoxy)ethoxy)ethoxy)ethoxy)phenyl)-7-methoxy-4-nitroisoquinolin-1(2H)-one Sodium azide (1.0 g) is added to a solution of tetraethyleneglycol dimethanesulphonate (5.25 g, 15 mmol), obtained according to A. W. Chwabacher et al. (J. Org. Chem. 1998, 65(5), 1717), in 18 mL of 95° ethanol. The reaction mixture is taken to reflux for 24 hours. Then the solvent is evaporated off, the reaction crude is added to 100 mL of salt water and extracted with ether (3×100 mL). The organic phase is dried over $MgSO_4$, filtered and concentrated under reduced pressure. The residue obtained is purified by chromatography on a silica column using a gradient of AcOEt in hexane (1/1 to 3/1) as eluents. 2-(2-(2-(2-azidoethoxy)ethoxy)ethoxy)ethyl mono-methanesulphonate 47 (2.10 g, 47%) is obtained, which is used directly in the following stage.

2-(2-(2-(2-azidoethoxy)ethoxy)ethoxy)ethyl methanesulphonate (175 mg, 0.58 mmol) and $Cs_2CO_3$ (190 mg, 0.58 mmol) are added to a mixture of 3-(4-hydroxyphenyl)-7-methoxyisoquinolin-1(2H)-one (compound 45) (130 mg, 0.48 mmol) in DMF (6 mL). The reaction mixture is heated at 80° C. for 24 hours. Then the solvent is evaporated off, the reaction crude is added to water (100 mL) and extracted with $CH_2Cl_2$ (3×100 mL). The organic phase is dried over $MgSO_4$, filtered and concentrated under reduced pressure. The residue obtained is purified by chromatography on a silica column using a gradient of EtOH (1 to 3%) in $CH_2Cl_2$ as eluents. Intermediate 3-(4-(2-(2-(2-(2-azidoethoxy)ethoxy)ethoxy)ethoxy)phenyl)-7-methoxyisoquinolin-1(2H)-one (52 mg, 23%) is obtained, which is used directly in the following stage.

Nitration of the compound 3-(4-(2-(2-(2-(2-azidoethoxy)ethoxy)ethoxy)ethoxy)phenyl)-7-methoxyisoquinolin-1(2H)-one, obtained above, is carried out according to the conditions described by E. Bisagni et al. (Tetrahedron, 1996, 52, 10427-10440) and provides the expected product 3-(4-(2-(2-(2-(2-azidoethoxy)ethoxy)ethoxy)ethoxy)phenyl)-7-methoxy-4-nitroisoquinolin-1(2H)-one 47 with a yield of 50%, MS 512 [M−H]$^+$; $^1H$ NMR ($CDCl_3$) 8.63 (1H, br s), 7.82 (1H, br s), 7.63 (1H, d), 7.42 (3H, m), 7.03 (2H, d), 4.19 (2H, t), 3.96 (3H, s), 3.89 (2H, t), 3.71 (10H, m), 3.38 (2H, t), Anal. Cal. for $C_{24}H_{27}N_5O_8 \cdot H_2O$, C, 54.23; H, 5.50. Found: C, 54.49; H, 5.21.

Compound 48: Dimethyl 1-[7-methoxy-3-(4-methoxyphenyl)-1-oxo-1,2-dihydroisoquinolin-4-yl]-1H-[1,2,3]triazole-4,5-dicarboxylate At 0° C., a solution of sodium nitrite (12 mg, 0.17 mmol) in DMF (0.2 ml) is added dropwise to a solution of 4-amino-7-methoxy-3-(4-methoxyphenyl)isoquinolin-1(2H)-one (compound 1) (47 mg, 0.16 mmol) in AcOH (0.7 mL). The mixture is stirred at 0° C. for 30 minutes. then sodium azide (12.3 mg, 0.19 mmol) is added to the reaction and the mixture is stirred at 0° C. for 1 hour. The reaction is stopped by the addition of 10 mL of water and the medium is extracted with 3×10 ml of dichloromethane. The organic phases are washed with 3×10 mL of water, dried over $MgSO_4$ and concentrated under vacuum. The residue obtained, placed under an argon atmosphere, is dissolved in 1 mL of dioxane then dimethyl acetylenedicarboxylate (77.7 µl, 0.63 mmol) is added to the solution and the mixture is then heated at 50° C. for 12 hours. The solvents are then evaporated off, water is added and the medium is extracted three times with EtOAc. The organic phase is dried over $MgSO_4$, filtered then evaporated. The residue is purified by silica gel column chromatography using a $CH_2Cl_2$—ethanol mixture as eluent (100% to 98/2) in order to produce the expected compound 48 (10 mg, 13%) in the form of a yellow solid; mp 220° C.; $^1H$ NMR ($CDCl_3$): 9.76 (1H, br s), 7.82 (1H, s), 7.28 (1H, dd), 7.23 (2H, d), 6.86 (2H, d), 6.75 (1H, d), 3.98 (3H, s), 3.95 (3H, s), 3.81 (3H, s), 3.69 (3H, s); MS 487 (M+23).

Compound 49: 7-Methoxy-3-(4-methoxyphenyl)-4-morpholinoisoquinolin-1(2H)-one

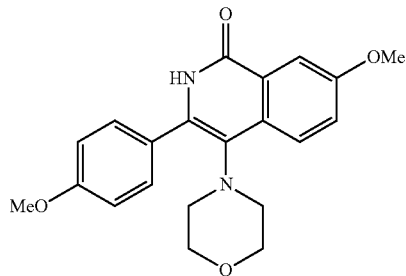 [SMILES: COc1ccc(-c2[nH]c(=O)c3cc(OC)ccc3c2N2CCOCC2)cc1]

and Compound 50: 4-(2-(2-hydroxyethoxy)ethylamino)-7-methoxy-3-(4-methoxyphenyl)isoquinolin-1(2H)-one

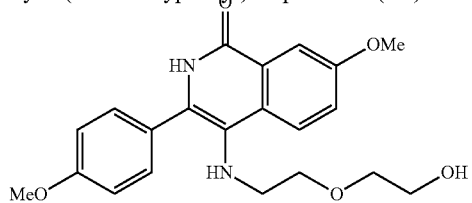

NaIO4 (66 mg, 0.33 mmol) is added to a flask containing 1,4-anhydroerythritol (34 mg, 0.33 mmol) dissolved in a water/CH$_3$CN mixture (1:1; 4 mL) and the mixture is maintained under stirring for 18 hours. 4-amino-7-methoxy-3-(4-methoxyphenyl)isoquinolin-1(2H)-one (compound 1) (100 mg, 0.33 mmol) and NaBH$_3$CN (63 mg, 1 mmol) are then added to the solution of 2,2'-oxybis(acetaldehyde) prepared previously. Then, 3 drops of acetic acid are added and the medium is stirred for 3 hours at ambient temperature. The reaction is stopped by the addition of 10 mL of water. The medium is extracted with 3×10 mL of dichloromethane. The organic phases are washed with 3×10 mL of water, dried over MgSO4 and concentrated under vacuum. The residue is purified by silica gel column chromatography with dichloromethane-ethanol (100/0 to 98/2) as eluent in order to produce successively i) the compound 7-methoxy-3-(4-methoxyphenyl)-4-morpholinoisoquinolin-1(2H)-one 49 (10 mg, 8%) in the form of a white solid, mp>270° C.; $^1$H NMR (CDCl$_3$): 8.18 (1H, br s), 7.99 (1H, d), 7.83 (1H, dd), 7.37 (3H, m), 7.03 (2H, d), 3.97 (3H, s), 3.91 (3H, s), 3.72 (4H, m), 2.90 (2H, m), 2.75 (2H, m); MS 367 (M+H); and ii) the compound 4-(2-(2-hydroxyethoxy)ethylamino)-7-methoxy-3-(4-methoxyphenyl)isoquinolin-1(2H)-one 50 (15 mg, 12%) in the form of a white solid, mp 139° C.; $^1$H NMR (CDCl$_3$): 8.71 (1H, br s), 7.89 (1H, d), 7.82 (1H, s), 7.45 (2H, d), 7.34 (1H, dd), 7.01 (2H, d), 3.94 (3H, s), 3.87 (3H, s), 3.60 (2H, t), 3.49 (2H, t), 3.38 (2H, t), 3.03 (2H, t), 1.75 (1H, br s), MS 385 (M+H).

Compound 56: 4-Chloro-7-hydroxy-3-(4-hydroxyphenyl)isoquinoline-1(2H)-one

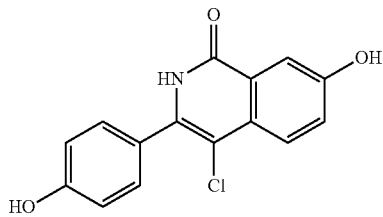 [SMILES: O=c1[nH]c(-c2ccc(O)cc2)c(Cl)c2ccc(O)cc12]

In a Schlenk flask, 7-methoxy-3-(4-methoxyphenyl)-4-nitroisoquinoline-1(2H)-one (compound 6) (150 mg, 0.46 mmol) and benzyltriethylammonium chloride (732 mg, 3.22 mmol) are dissolved in 37% hydrochloric acid (13 mL). The mixture is heated at 130° C. for 20 hours. After evaporation under reduced pressure, water (20 ml) is added and the precipitate formed is filtered, washed with water, dried and chromatographed on a silica gel column using a gradient of CH$_2$Cl$_2$/ethanol: 100/0 to 98/2 as eluent in order to produce compound 56 (6 mg, 4%) in the form of a black solid.

1H NMR (DMSO-d6) δ 11.42 (s, 1H), 10.20 (s, 1H), 9.82 (s, 1H), 7.79 (d, 1H), 7.58 (d, 1H), 7.36 (d, 2H), 7.33 (s, 1H), 6.85 (d, 2H).

Compound 57: 7-Hydroxy-3-(4-hydroxyphenyl)isoquinoline-1(2H)-one

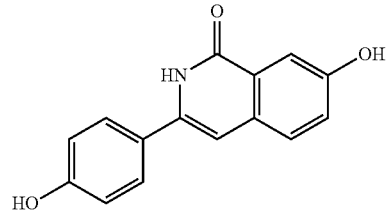

The compound 7-methoxy-3-(4-methoxyphenyl)isoquinoline-1(2H)-one (300 mg, 1 mmol), benzyltriethylammonium chloride (1.68 g, 7 mmol) and 37% hydrochloric acid (20 mL) are introduced into a sealed tube. The medium is heated for 20 hours at 140° C. then the mixture is evaporated to dryness under reduced pressure. After the addition of water (20 mL) to the residue obtained, a precipitate is formed. It is filtered and dried under in order to produce the expected 7-hydroxy-3-(4-hydroxyphenyl)isoquinoline-1(2H)-one 57 (200 mg, 74%) in the form of a brown solid.

1H NMR (DMSO-d6) δ 11.14 (br s, 1H), 9.86 (br s, 1H), 9.74 (br s, 1H), 7.51 (m, 4H), 7.16 (s, 1H), 6.82 (s, 2H), 6.67 (s, 1H); MS 252 [M+H]+;

Anal. Cal. for C$_{15}$H11NO3:
C, 71.14; H, 4.38; N, 5.53. Found: C, 69.77; H, 4.53; N, 5.86.

Compound 58: 6-Methoxy-2-(4-methoxyphenyl)quinoline-4(1H)-one

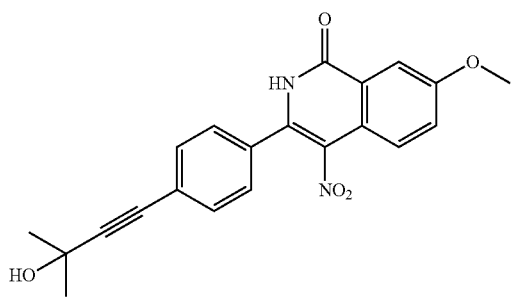 [SMILES: COc1ccc2c([N+](=O)[O-])c(-c3ccc(C#CC(C)(C)O)cc3)[nH]c(=O)c2c1]

In a 100-mL flask, p-anisidine (300 mg, 2.4 mmol) is dissolved in 2-methoxyethanol (20 mL). Ethyl 3-(4-methoxyphenyl)-3-oxopropanoate (459 μl, 2.4 mmol) is added to the previous solution then 3 drops of acetic acid are also added to the reaction medium. The mixture is heated for 24 hours at 120° C. This mixture is then evaporated under reduced pressure and the residue obtained is diluted in diphenyl ether (10 mL) then added to a three-necked 100-mL flask containing boiling diphenyl ether (25 mL). The medium is heated under reflux for 1 hour and the cooled solution is then poured into hexane (100 mL). The precipitate formed is filtered, washed with hexane, dried and chromatographed on a silica gel column using a gradient of $CH_2Cl_2$/ethanol: 100/0 to 98/2 as eluent in order to produce compound 58 (100 mg, 15%) in the form of a brown powder.

1H NMR (DMSO-d6)

δ 11.55 (s, 1H), 7.76 (d, 2H), 7.69 (d, 1H), 7.47 (s, 1H), 7.28 (d, 1H), 7.10 (d, 2H), 6.26 (s, 1H), 3.82 (s, 6H); MS 282 [M+H]+;

Anal. Cal. for $C_{17}H_{15}NO_3 \cdot 0.1H_2O$: C, 72.05; H, 5.36; N, 4.64. Found: C, 71.85; H, 5.27; N, 4.94.

Compound 59: 3-(4-(3,3-dimethylbut-1-ynyl)phenyl)-7-methoxy-4-nitroisoquinolin-1(2H)-one

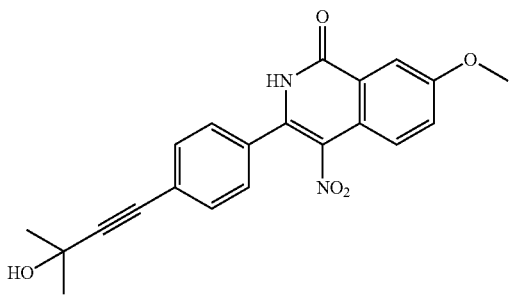 [SMILES: COc1ccc2c([N+](=O)[O-])c(-c3ccc(C#CC(C)(C)O)cc3)[nH]c(=O)c2c1]

Compound 59 is synthesized in the same way as compound 60 but starting from 2-methylbut-3-yn-2-ol and 32 the synthesis of which is indicated above.

$^1$H NMR (300 mHz, DMSO): 12.21 (1H), 7.26 (1H), 7.65 (1H), 7.52 (1H), 7.50 (4H), 5.54 (1H), 3.92 (1H), 1.48 (6H)

Compound 60: 3-(4-(3,3-dimethylbut-1-ynyl)phenyl)-7-methoxy-4-nitroisoquinolin-1(2H)-one

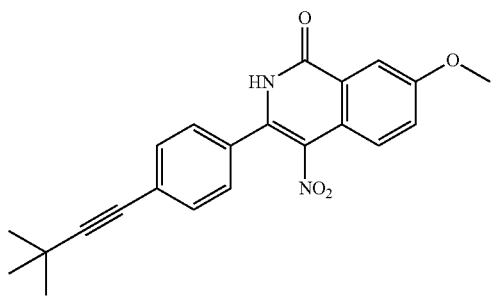 [SMILES: COc1ccc2c([N+](=O)[O-])c(-c3ccc(C#CC(C)(C)C)cc3)[nH]c(=O)c2c1]

Alkyne (87.6 mg, 1.06 mmol, 4.0 eq.) $PdCl_2(PPh_3)$ (15 mg, 0.021 mmol, 0.08 mol %) and CuI (2.0 mg, 0.011 mmol, 0.04 mol %) are added to a solution of 32 (100 mg, 0.26 mmol, 1.0) in a THF/TEA mixture (1 ml/0.75 ml) in a sealed tube. The reaction medium is stirred at 70° C. for 18 hours. After returning to a.t., the reaction medium is concentrated under reduced pressure, diluted in ethyl acetate, filtered on celite and washed with ethyl acetate. The crude is then purified by silica gel chromatography (c-hexane/ethyl acetate. 3:2) in order to obtain 3-(4-(3,3-dimethylbut-1-ynyl)phenyl)-7-methoxy-4-nitroisoquinolin-1(2H)-one 60 in the form of a yellow solid (70 mg, yield=71%).

$^1$H NMR (300 mHz, DMSO): 9.02 (1H), 7.8 (1H), 7.65 (1H), 7.42 (2H), 7.38 (3H), 3.96 (3H), 1.33 (9H)

Compound 61: 2-Amino-7-methoxy-3-(4-methoxyphenyl)isoquinoline-1(2H)-one

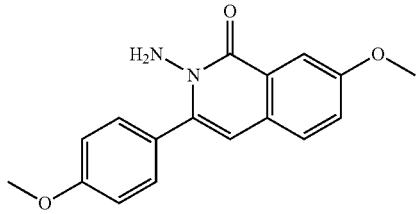

In a 25-mL flask under argon, 7-methoxy-3-(4-methoxyphenyl)isoquinoline-1(2H)-one (100 mg, 0.38 mmol) is dissolved in DMF (5 mL). At 0° C., sodium hydride (60% in oil, 30 mg, 0.76 mmol) is added. After stirring for 30 minutes at 0° C., O-mesitylenesulphonylhydroxylamine (freshly prepared according to the literature (Y. Tamura et al. Synthesis 1977, 1) (82 mg, 0.38 mmol) is added at ambient temperature. Stirring is maintained for 12 hours then water (20 mL) is added to the reaction medium. This medium is extracted with dichoromethane. The organic phases are washed with water, dried over $MgSO_4$ and concentrated under vacuum. The residue obtained is chromatographed on a silica gel column using a gradient of $CH_2Cl_2$/ethanol: 100/0 to 98/2 as eluent in order to produce compound 61 (51 mg, 46%) in the form of an orange solid.

1H NMR CDCl3 δ 7.82 (s, 1H), 7.50 (t, 3H), 7.29 (d, 1H), 7.01 (d, 2H), 6.50 (s, 1H), 5.18 (s, 2H), 3.93 (d, 6H);

MS 297 [M+H]+.

Compound 62: 2-Amino-7-methoxy-3-(4-methoxyphenyl)-4-nitroisoquinoline-1(2H)-one

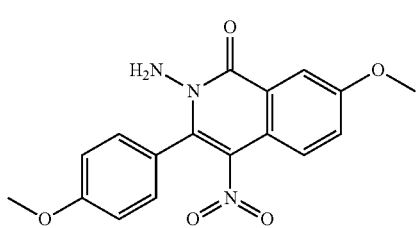

In a 25-mL flask under argon, 7-methoxy-3-(4-methoxyphenyl)-4-nitroisoquinoline-1(2H)-one (compound D5, 150 mg, 0.46 mmol) is dissolved in 5 mL of dimethylformamide. At 0° C., potassium carbonate (317 mg, 2.3 mmol) is added. After stirring for 30 minutes at 0° C., O-mesitylenesulphonylhydroxylamine (freshly prepared according to the literature Y. Tamura et al. Synthesis 1977, 1) (93 mg, 0.46 mmol) is added. Stirring is maintained for 12 hours at ambient temperature. The medium is then neutralized with 20 mL of a N hydrochloric acid solution then extracted with 3×10 mL of dichoromethane. The organic phases are washed with 3×10 ml of $H_2O$, dried over $MgSO_4$ and concentrated under vacuum. The residue obtained is chromatographed on a silica gel column using a gradient of CH$_2$Cl$_2$/ethanol: 100/0 to 97/3 as eluent in order to produce compound 62 (65 mg, 41%) in the form of a yellow solid.

1H NMR CDCl3 δ 7.88 (s, 1H), 7.56 (d, 1H), 7.40 (d, 3H), 7.04 (d, 2H), 5.10 (s, 2H), 3.99 (s, 3H), 3.88 (s, 3H);

MS 342 [M+H]+.

Compound 64: 1,7-Dimethoxy-3-(4-methoxyphenyl) isoquinoline and compound 65, 7-Methoxy-3-(4-methoxyphenyl)-2-methylisoquinoline-1(2H)-one In a 25-mL flask under argon, 7-methoxy-3-(4-methoxyphenyl)isoquinoline-1(2H)-one (200 mg, 0.71 mmol) is dissolved in 5 mL of dimethylformamide. At 0° C., potassium carbonate (491 mg, 3.5 mmol) is added. After stirring for 30 minutes at 0° C., iodomethane (444 µL, 7.1 mmol) is added. Stirring is maintained for 12 hours at ambient temperature. The medium is neutralized with 20 mL of a 1N hydrochloric acid solution then extracted with 3×10 mL of dichoromethane. The organic phases are washed with 3×10 ml of H$_2$O, dried over MgSO$_4$ and concentrated under vacuum. The residue obtained is chromatographed on a silica gel column using a gradient of CH$_2$Cl$_2$/ethanol: 100/0 to 95/5 as eluent in order to produce compound 64 (39 mg, 18%) in the form of a white solid and compound 65 (122 mg, 58%) in the form of a beige solid.

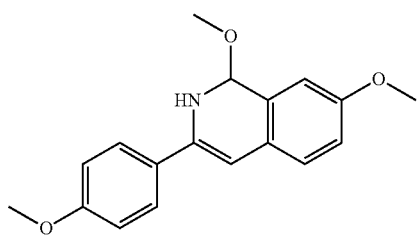

Compound 64

1H NMR CDCl3 δ 8.11 (d, 2H), 7.70 (d, 1H), 7.58 (s, 1H), 7.53 (s, 1H), 7.31 (d, 1H), 7.03 (d, 2H), 4.25 (s, 3H), 3.97 (s, 3H), 3.90 (s, 3H);

MS 296 [M+H]+.

Compound 65: 7-Methoxy-3-(4-methoxyphenyl)-2-methylisoquinoline-1(2H)-one

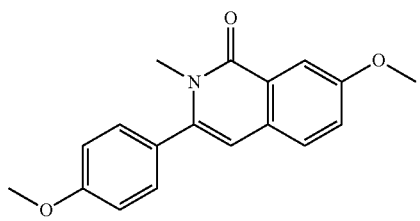

1H NMR CDCl3 δ 7.84 (s, 1H), 7.40 (d, 1H), 7.31 (d, 2H), 7.24 (d, 1H), 6.97 (d, 2H), 6.40 (s, 1H), 3.93 (s, 3H), 3.86 (s, 3H), 3.44 (s, 3H);

MS 296 [M+H]+.

Compound 66: 7-Methoxy-3-(4-methoxyphenyl)-2-methyl-4-nitroisoquinoline-1(2H)-one

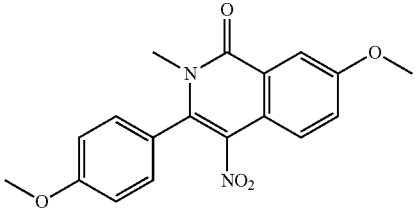

In a 25-mL flask, 7-methoxy-3-(4-methoxyphenyl)-2-methylisoquinoline-1(2H)-one (compound 65, 50 mg, 0.17 mmol) is dissolved in 0.5 mL of ethyl acetate and 1.5 mL of acetic acid. At 0° C., nitric acid (at 52.5%, 380, 0.425 mmol) is added to the medium and stirring is maintained for 3 hours. 10 ml of ice water are added and the yellow precipitate obtained is then filtered, washed with water and dried in order to produce compound 66 (25 mg, 44%) in the form of a yellow solid.

1H NMR CDCl3 δ 7.91 (s, 1H), 7.50 (d, 1H), 7.38 (d, 1H), 7.32 (d, 2H), 7.03 (d, 2H), 3.98 (s, 3H), 3.88 (s, 3H), 3.35 (s, 3H);

MS 341 [M+H]+.

Compound 67: 2-(2-Hydroxyethyl)-7-methoxy-3-(4-methoxyphenyl)isoquinoline-1(2H)-one

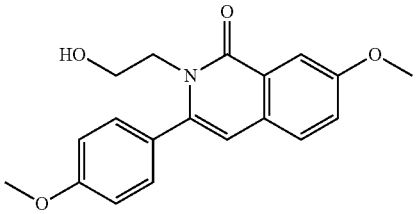

In a 25-mL flask under argon, the compound 7-methoxy-3-(4-methoxyphenyl)isoquinoline-1(2H)-one (300 mg, 1.06 mmol) is dissolved in 10 mL of DMF. Potassium carbonate (737 mg, 5.3 mmol) is then added. After stirring for 30 minutes, 2-bromoethanol (746 µl, 10.6 mmol) is added. Stirring is maintained for 24 hours at 100° C. Once returned to ambient temperature, the medium is neutralized with 20 mL of a N hydrochloric acid solution then extracted with 3×10 mL of dichloromethane. The organic phases are washed with 3×10 mL of H$_2$O, dried over MgSO4 and concentrated under vacuum. The residue is purified by silica gel column chromatography with cyclohexane-ethyl acetate (60/40) as eluent in order to produce 67 (35 mg, 10%) in the form of a white solid.

1H NMR CDCl3 δ 7.98 (d, 2H), 7.68 (d, 1H), 7.54 (d, 2H), 7.32 (d, 1H), 7.02 (d, 2H), 4.84 (d, 2H), 4.23 (br s, 1H), 4.13 (d, 2H), 3.96 (s, 3H), 3.87 (s, 3H),

MS 326 [M+H]+.

Compound 68: 2-(2-Hydroxyethyl)-7-methoxy-3-(4-methoxyphenyl)-4-nitroisoquinoline-1(2H)-one

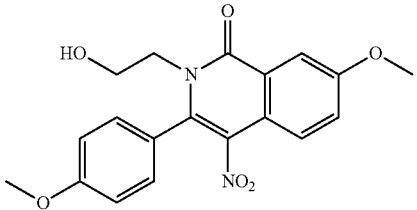

In a 25-mL flask under argon, 7-methoxy-3-(4-methoxyphenyl)-4-nitroisoquinoline-1(2H)-one (compound D5, 150 mg, 0.46 mmol) is dissolved in 5 mL of DMF. Potassium carbonate (317 mg, 2.3 mmol) is then added. After stirring for 30 minutes, 2-bromoethanol (329 µl, 4.6 mmol) is added. Stirring is maintained for 24 hours at 50° C. Once returned to ambient temperature, the medium is neutralized with 20 mL of a 1N hydrochloric acid solution then extracted with 3×10 mL of ethyl acetate. The organic phases are washed with 3×10 ml of H₂O, dried over MgSO₄ and concentrated under vacuum. The residue obtained is chromatographed on a silica gel column using the cyclohexane-ethyl acetate mixture (60/40) as eluent in order to produce the expected 2-(2-hydroxyethyl)-7-methoxy-3-(4-methoxyphenyl)-4-nitroisoquinoline-1(2H)-one 68 (73 mg, 43%) in the form of a yellow solid.
1H NMR CDCl3 δ 7.90 (s, 1H), 7.49 (d, 1H), 7.42 (d, 1H), 7.34 (d, 2H), 7.02 (d, 2H), 4.12 (d, 2H), 3.99 (s, 3H), 3.89 (s, 3H), 3.80 (d, 2H), 2.80 (br s, 1H);
MS 393 [M+Na]+.

Compound 69: 4-Iodo-7-methoxy-1-(4-methoxybenzyloxy)-3-(4-methoxyphenyl)isoquinoline

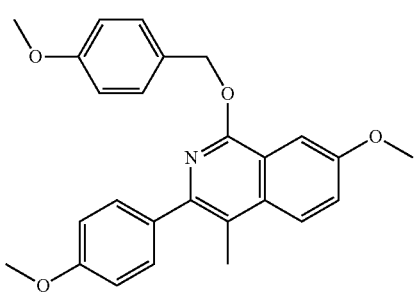

In a 25-mL flask under argon, 4-iodo-7-methoxy-3-(4-methoxyphenyl)isoquinolin 1(2H)-one (500 mg, 1.23 mmol) is dissolved in 15 mL of anhydrous THF. 4-methoxybenzyl alcohol (217 µl, 1.84 mmol), triphenylphosphine (482 mg, 1.84 mmol) and diisopropyl azodicarboxylate (261 µl, 1.84 mmol) are added to the previous solution. After stirring overnight at ambient temperature, the medium is hydrolyzed with 20 mL of water and extracted with 3×20 mL of dichloromethane. The organic phases are washed with 3×10 mL of water, dried over MgSO₄ and concentrated under vacuum. Compound 69 is obtained by recrystallization from ether (358 mg, 55%). 1H NMR CDCl3 δ 7.94 (s, 1H), 7.89 (d, 1H), 7.34 (d, 1H), 6.98 (d, 2H), 6.91 (d, 2H), 6.81 (d, 2H), 6.72 (d, 2H), 5.19 (s, 2H), 3.97 (s, 3H), 3.88 (s, 3H), 3.74 (s, 3H);
MS 528 [M+H]+.

Compound 70: 7-Methoxy-1-(4-methoxybenzyloxy)-3-(4-methoxyphenyl)-4-(trifluoromethyl)isoquinoline

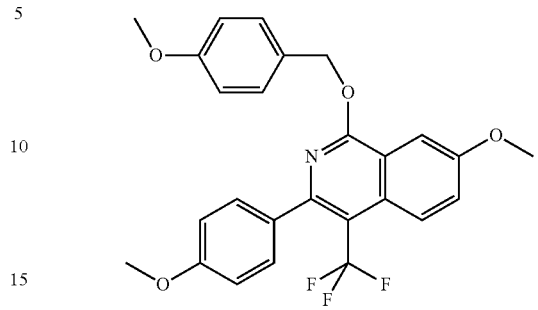

In a 10-mL flask, 4-iodo-7-methoxy-1-((4-methoxybenzyl)oxy)-3-(4-methoxyphenyl)isoquinoline (100 mg, 0.2 mmol) is dissolved in 2 mL of anhydrous DMF. Copper iodide (95.2 mg, 0.5 mmol) and methyl 2,2-difluoro-2-(fluorosulphonyl)acetate (119 µl, 0.94 mmol) are added to the previous solution. After stirring overnight at 80° C., the reaction medium is filtered and washed with 30 mL of dichloromethane. The filtrate obtained is washed with 3×10 mL of water, dried over MgSO₄ and concentrated under vacuum in order to produce the expected compound 70 (75 mg, 80%).
1H NMR CDCl3 δ 7.97 (s, 1H), 7.87 (d, 1H), 7.37 (dd, 1H), 6.98 (d, 2H), 6.85 (d, 2H), 6.80-6.62 (m, 4H), 5.04 (s, 2H), 3.96 (s, 3H), 3.86 (s, 3H), 3.75 (s, 3H);
MS 470 [M+H]+.

Compound 71: 1-Amino-7-methoxy-3-(4-methoxyphenyl)-4-nitroisoquinoline

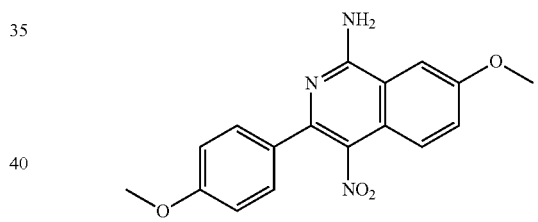

In a 25-mL Schlenk flask, under argon, 1-chloro-7-methoxy-3-(4-methoxyphenyl)-4-nitroisoquinoline (100 mg, 0.43 mmol) is dissolved in 20 mL of a saturated solution of ammonia in ethanol. After stirring for 4 days at 80° C., the medium is concentrated under vacuum then purified by silica gel column chromatography with dichloromethane-ethanol (95/5) as eluent in order to produce the expected amine compound 71 (79 mg, 56%) in the form of a yellow solid. 1H NMR CDCl3 δ 7.81 (d, 1H), 7.60 (d, 2H), 7.45 (d, 1H), 7.07 (s, 1H), 6.99 (d, 2H), 5.44 (s, 2H), 3.99 (s, 3H), 3.87 (s, 3H); MS 326 [M+H]+.

Compound 72: 3-(4-hydroxyphenyl)-7-methoxy-4-nitroisoquinolin-1(2H)-one

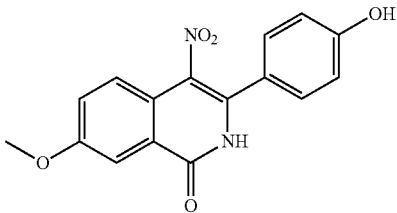 [SMILES: COc1ccc2c([N+](=O)[O-])c(-c3ccc(O)cc3)[nH]c(=O)c2c1]

The molecule was prepared according to the procedure described by Bisagni (Bisagni, E.; Landras, C.; Thirot, S.; Huel, C., *Tetrahedron* 1996, 52 (31), 10427-10440), starting from 2-(4-(benzyloxy)phenyl)ethanoic acid (Mannekens, E.; Tourwe, D.; Lubell, W. D., *Synthesis* 2000, 2000 (09), 1214.1216) and 4-methoxybenzaldehyde. The O-benzylated intermediate is then debenzylated according to the method described by Mannekens (Mannekens, E.; Tourwe, D.; Lubell, W. D., *Synthesis* 2000, 2000 (09), 1214.1216).

$^1$H NMR (300 mHz, CdCl$_3$): δ 12.01 (s, 1H), 10.01 (s, 1H), 7.70 (d, 1H), 7.56 (d, 1H), 7.49 (dd, 1H), 7.31 (d, 1H), 6.86 (d, 2H), 3.91 (s, 3H)

Compound 73: tert-butyl 4-(7-methoxy-4-nitro-1-oxo-1,2-dihydroisoquinolin-3-yl)phenyl carbonate

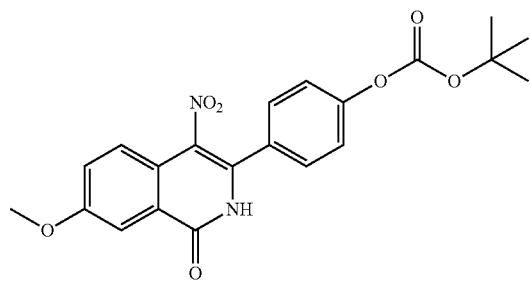 [SMILES: COc1ccc2c([N+](=O)[O-])c(-c3ccc(OC(=O)OC(C)(C)C)cc3)[nH]c(=O)c2c1]

A solution of 3-(4-hydroxyphenyl)-7-methoxy-4-nitroisoquinolin-1(2H)-one (50.0 mg, 0.16 mmol, 1.0 eq.), K$_2$CO$_3$ (22.15 mg, 0.16 mmol, 1.0 eq.), and Boc2 (34.9 mg, 0.16 mmol, 1.0 eq.) in DMF (1 ml) degassed with argon in a sealed tube is stirred at a.t. for 18 hours. The reaction medium is diluted with H$_2$O. The organic phases are extracted with ethyl acetate (twice), washed with a saturated solution of NaCl (twice), dried over MgSO4 then concentrated under reduced pressure, in order to obtain a pure product (yield=100%).

$^1$H NMR (300 mHz, DMSO): δ 12.21 (s, 1H), 7.70 (d, 1H), 7.63 (d, 1H), 7.56 (d, 1H), 7.50 (dd, 1H), 7.33 (d, 1H), 3.92 (s, 3H), 1.51 (s, 9H)

Compound 74: 2-(p-hydroxybenzyl)-3penylisoquinolin-1(2H)-one

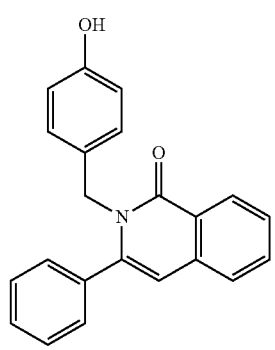 [SMILES: O=c1c2ccccc2cc(-c2ccccc2)n1Cc1ccc(O)cc1]

NaOtBu (68.23 mg, 0.71 mmol, 3.0 eq.), Xantphos (6.8 mg, 0.012 mmol, 5 mol %), Pd$_2$ dba$_3$ (10.8 mg, 0.012 mmol, 5 mol %) are added to a flask dried under vacuum. The reagents are dissolved in toluene distilled with CaH$_2$ under argon (0.8 ml). The red solution is degassed under argon with sonication for 30 seconds. A solution of (Z)-1-bromo-2-(2-bromo-2-phenylvinyl)benzene (80 mg, 0.24 mmol, 1.0 eq) and p-methoxybenzyl amine (114 mg, 0.83 mmol, 3.5 eq.) in toluene distilled with CaH$_2$ under argon (0.8 ml) is added to the catalytic system. After addition, the reaction medium is degassed with argon, and stirred for 1 hour 30 minutes at 55° C. Then, the reaction medium is degassed with carbon monoxide (in a flask, 1 atm.) for 25 minutes at 55° C. Then, the reaction medium is stirred at 90° C. for 16 hours. After cooling down to a.t., the reaction medium is quenched with a 1N HCl solution (5 ml). The organic phases are extracted with dichloromethane (twice), washed with a saturated solution of NaCl (twice), dried over MgSO4 then concentrated under reduced pressure. The crude is then purified by silica gel chromatography (pentane/diethyl ether (7/3)) in order to obtain 2-(4-methoxybenzyl)-3-phenylisoquinolin-1(2H)-one (45 mg, yield=54%) in the form of a yellowish solid.

$^1$H NMR (300 mHz, CdCl$_3$): δ 8.49 (d, 1H), 7.67 (t, 1H), 7.50 (m, 2H), 7.44-7.35 (m, 3H), 7.22 (d, 2H), 6.83 (d, 2H), 6.69 (d, 2H), 5.20 (s, 2H), 3.76 (s, 3H)

$^{13}$C NMR (75 mHz, CdCl$_3$): δ 163.2 (CO); 158.6 (C); 143.9 (C); 136.5 (C); 136.0 (C); 132.5 (CH); 129.8 (CH); 129.3 (CH); 128.8 (CH); 128.4 (CH); 128.3 (CH, CH); 126.7 (CH); 125.6 (CH); 125.3 (C); 113.7 (CH); 108.2 (CH); 55.2 (—OMe); 48.0 (—CH$_2$—)

A solution of BBr$_3$ (170 L of a (1M) solution in CH$_2$Cl$_2$) is added to a solution of 2-(4-methoxybenzyl)-3-phenylisoquinolin-1(2H)-one obtained above (30 mg, 0.087 in CH$_2$Cl$_2$ (1 ml) at −78° C. The orange solution is stirred from 0° C. to ambient temperature over 1 hour. TLC (cyclohexane/ethyl acetate/triethyleamine 1%) indicates a complete reaction. EtOH (2 ml), a saturated aqueous solution of NaHPO$_4$ and CH$_2$Cl$_2$ (2 ml) are added. After extraction, the collected organic phases are dried (MgSO$_4$) and evaporated under vacuum. The residue obtained is purified by chromatography on an SiO$_2$ column (cyclohexane-ethyl acetate, 1:1). 25 mg of 74 (93%) is obtained.

$^1$H NMR (CDCl$_3$, 300 MHz): 9.27 (S, H); 8.41 (d, 1H, J=14); 7.66-7.52 (m, H); 7.50-7.40 (m, 1H); 7.46-7.32 (m, 3H); 7.26-7.21 (m, 2H); 6.72 (d, J=7, 1H); 6, (d, J=7, 1H); 6.46 (s, 1H).

Example 14

Modulation of Chemoresistance to Paclitaxel by the Compounds of the Invention

As described in "Kyu-Ho Han et al., Modulation of drug resistance by α-tubulin in paclitaxel-resistant human lung cancer cell lines European Journal of Cancer 2000 36 (12): 1565-1571", clones of the NCI-H460 line (ATCC # HTB-177, human large cell pulmonary carcinoma), resistant to Paclitaxel are selected and designated NCI-H460/R.

These resistant cells, as well as "normal" NCI-H460 cells are seeded in 96-well plates (1000 per well) and incubated with different concentrations of compound 6 or paclitaxel or vinblastine (from 0.01 nM to 100 μM), for 5 days (120 hours).

At the end of this incubation, Hoechst 33342 (1 μg/ml) is added to the culture medium and the living cells are counted under a fluorescence microscope (Zeiss Axiovert 200M), in order to evaluate the concentration reducing the number of cells at 120 hours by 50% with respect to the control, for each compound tested.

Example 15

Evaluation of the Anti-Inflammatory Activity of the Compounds of the Invention

In order to induce inflammatory oedema of a rat or mouse paw, an intradermal injection of carrageenan (CAR) (1%, v/v)

is carried out and evaluated according to the method of Winter, C. A., Risley E. A. and Nuss G. W. (Carrageenan-induced edema in the hindpaw of rats as an assay for anti-inflammatory drugs. Proc. Soc. Axp. Biol. Med, 1962, v. 111: pp 544-7).

The compounds of the invention are given orally 1 to 6 hours before the injection of CAR. A 1% solution of CAR in a saline solution is injected by s. c. route into the sub-plantar part of the rat's (mouse's) right hindpaw. Then, the volume of the inflammatory reaction is measured by plethysmography between 1 and 5 hours after the injection of CAR. The volume of the inflammatory reaction is compared with that of the control (CAR injection without treatment or after treatment with the vehicle).

The invention claimed is:

1. A method for the treatment of mammals suffering from pathological angiogenesis or benign or malignant tumours, comprising administering to said mammal an effective amount of at least one compound of formula (I)

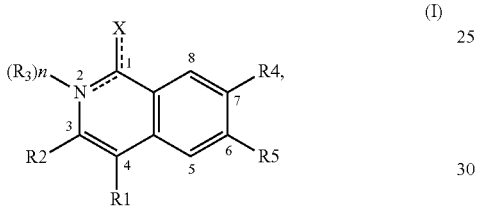

wherein,
the bond between carbon 1 and the X group is single or double, and the bond between nitrogen 2 and carbon 1 is single or double, it being understood that:
a) when the bond between X and carbon 1 is double, then the bond between nitrogen 2 and carbon 1 is single, and
b) when the bond between X and carbon 1 is single, then the bond between nitrogen 2 and carbon 1 is double, and formula I corresponds to an aromatic system of formula I-A:

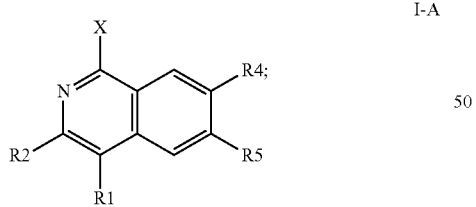

n represents 0 or 1;
X represents:
a) when n=1, then X represents O, or S,
b) when n=0, then X represents $OPO_3H_2$, OPO—(O—($C_1$-$C_2$)alkyl)$_2$, the alkyl being optionally substituted by one or more fluorines, O—($C_1$-$C_6$) alkyl, the alkyl being optionally substituted by one or more fluorines, NH—($C_1$-$C_6$)alkyl, S($C_3$-$C_6$)cycloalkyl;
R1 represents:
OH, $OPO_3H_2$, OPO—(O—($C_1$-$C_2$) alkyl)$_2$, the alkyl being optionally substituted by one or more fluorines, $CF_3$, $CH_2OR'$, R' representing H or ($C_1$-$C_6$) alkyl, the alkyl being optionally substituted by one or more fluorines, CHO,
$CONR_cR_d$, $R_c$ and $R_d$ representing independently of each other: H or a $C_1$-$C_6$ alkyl, and $NR_cR_d$ represents an amino acid bound by its amine function, a $C_3$-$C_6$ cycloalkyl, or $R_c$ and $R_d$ represent together a $C_2$-$C_6$ alkyl,
$NO_2$, $N_3$, ≡, C(=N)$NH_2$, $SO_3H$, $SO_2NH_2$, $SO_2NHCH_3$, $NHSO_2CH_3$, $CH_2SO_2NR_cR_d$, $CH_2NHSO_2Rc$, $SO_2$—$NRaRb$, $SO_2$-imidazole,
$NR_aR_b$, where $R_a$ and $R_b$ represent independently of each other: H, a $C_1$-$C_6$ alkyl, a $C_3$-$C_6$ cycloalkyl, or
$R_a$ is H, a $C_1$-$C_6$ alkyl, a $C_3$-$C_6$ cycloalkyl, and $R_b$=$COR_f$, $COOR_f$ or $CONR_eR_f$, $R_f$ and $R_e$ representing H, a $C_1$-$C_6$ alkyl, a $C_3$-$C_6$ cycloalkyl or an amino acid chain, or $R_a$ and $R_b$ represent together a $C_2$-$C_6$ alkyl, $R_a$ and $R_b$ can form a $C_5$ to $C_7$ ring, or a substitute or unsubstituted heteroaryl;
R2 represents:
a phenyl substituted by one to three substituents selected from the group consisting of:
a halogen, OH, NHRa,
ORe, Re representing a benzyl, a methylene triazole, substituted or not by a $C_1$-$C_6$ alkyl,
$OPO_3H_2$, OPO—(O—($C_1$-$C_2$)alkyl)$_2$, the alkyl being optionally substituted by one or more fluorines, $NH_2$,
an NH—CORc group in which Rc represents H, a $C_1$-$C_6$ alkyl, a $C_3$-$C_6$ cycloalkyl or an amino acid chain,
an O—($C_1$-$C_6$)alkyl, the alkyl being optionally substituted by one or more fluorines,
an O—$COR_1$ where $R_1$ represents O—($C_1$-$C_6$)alkyl, or NRiRii, Ri and Rii being able to be $C_1$-$C_6$ alkyl,
a $C_2$-$C_4$ alkyl group, the alkyl group being optionally substituted by one or more fluorines, a $C_2$-$C_4$ alkenyl group, substituted or not, a $C_2$-$C_4$ alkynyl group, substituted or not, a heteroaryl, substituted or not,
a cyclohexyl, a piperazine, a morpholine, a thiomorpholine, a piperidine,
a 4-($NH_2$—($CH_2$—$CH_2$O)p)Ph group in which p is an integer from 1 to 6;
R3 represents: H, ($C_1$-$C_6$)alkyl, the alkyl being optionally substituted by one or more fluorines, ($C_3$-$C_6$) cycloalkyl, O—($C_1$ to $C_6$) alkyl, $NH_2$, a propargyl group, $CH_2CN$;
R4 and R5 represent independently of each other:
H, OH, $OPO_3H_2$, OPO—(O—($C_1$-$C_2$)alkyl)$_2$, the alkyl being optionally substituted by one or more fluorines, an O—($C_1$-$C_6$)alkyl, the alkyl being optionally substituted by one or more fluorines, a $C_1$-$C_6$ alkyl, the alkyl being optionally substituted by one or more fluorines, a $C_3$-$C_6$ cycloalkyl, a halogen, or
R4 and R5 represent together a ($C_1$-$C_2$) alkenyl dioxy optionally substituted by one or more fluorines,
or a pharmaceutically acceptable salt.

2. The method of claim 1, wherein the compound of formula (I) functions as a protein phosphatase 1 inhibitor, vascular-disrupting agent and antiproliferative agent.

3. The method of claim 1, wherein the compound of formula (I) functions as a tubulin polymerization inhibitor, vascular-disrupting agent and antiproliferative agent.

4. The method of claim 1, wherein the compound of formula (I) functions as a protein phosphatase 1, tubulin polymerization inhibitor, vascular-disrupting agent and antiproliferative agent.

5. The method according to claim 3, wherein the R1 group of formula (I) is NO₂ or pyrrole.

6. The method of claim 1, wherein said mammals are suffering from a retinopathy.

7. The method according to claim 1, wherein the R2 group of formula (I) represents a phenyl substituted by a group of high steric hindrance.

8. The method according to claim 1, wherein the R2 group of formula (I) represents a phenyl substituted in the para position by said ORe, a halogen, or a C2-C4 alkyne group, substituted or not.

9. The method according to claim 1, wherein the R1 group of formula (I) is NO₂ or pyrrole and the R2 group of formula (I) is a phenyl substituted by a group of high steric hindrance.

10. The method according to claim 1, wherein the R1 group of formula (I) is NO₂ or pyrrole and the R2 group of formula (I) is a phenyl substituted in the para position by said ORe, a halogen, or a C2-C4 alkyne group, substituted or not.

11. The method according to claim 10, wherein the R3 group of formula (I) is H.

12. The method according to claim 1, wherein the compound of formula (I) is selected from the group consisting of:

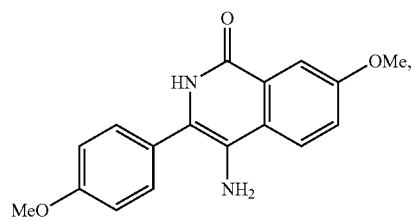
1

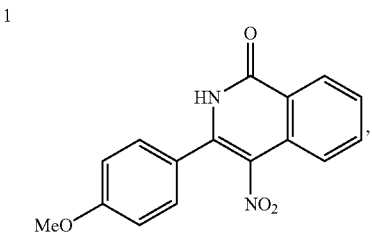
7

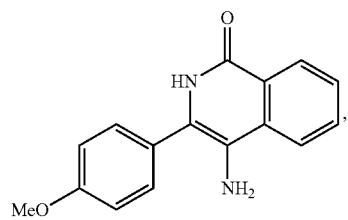
8

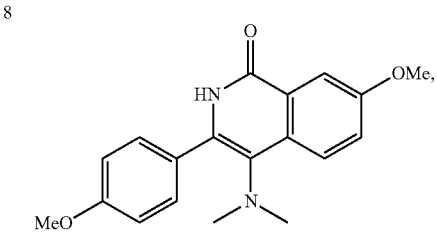
23

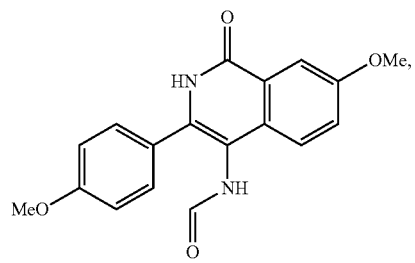

24

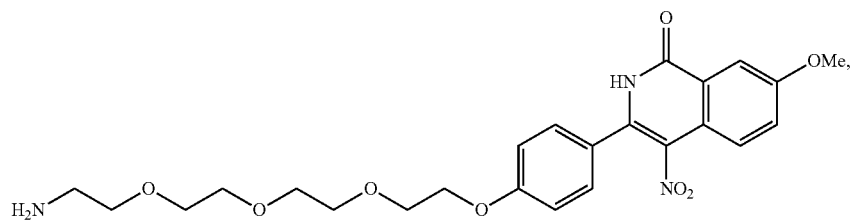
37

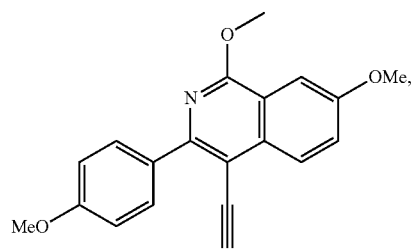
38

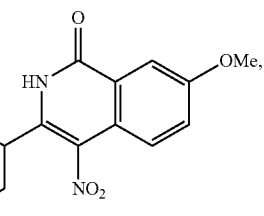

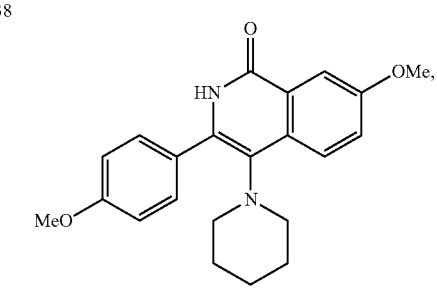
40

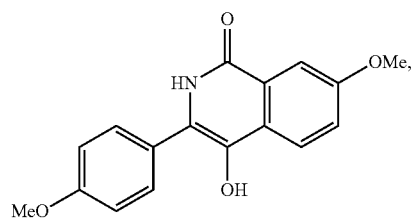
41
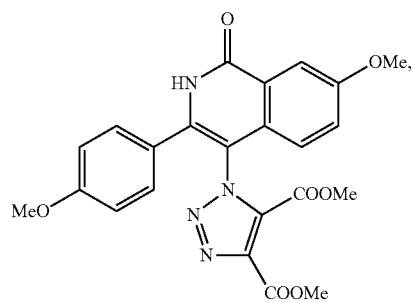
48
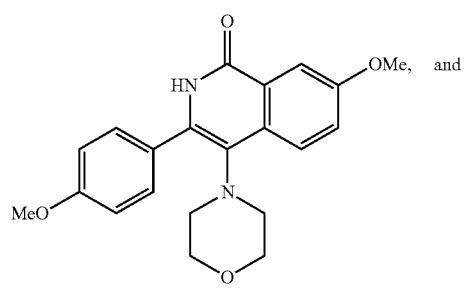
49
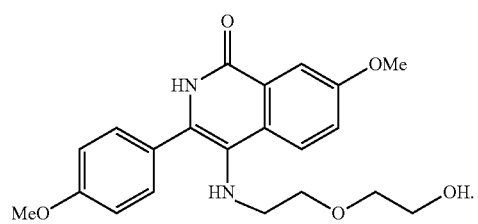
50
13. The method according to claim 1, wherein the compound of formula (I) is selected from the group consisting of:
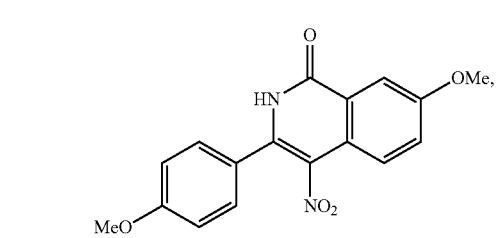
6
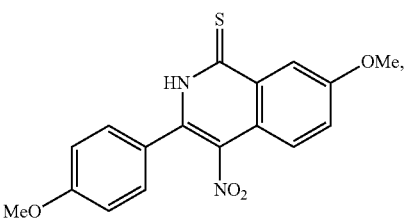
18
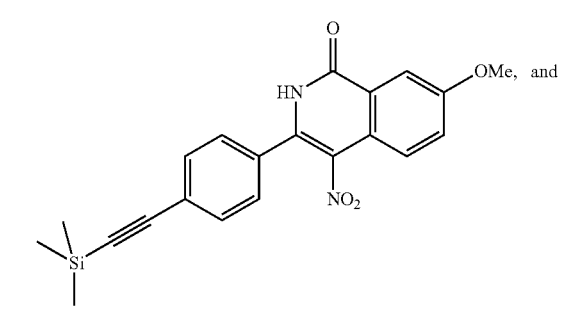
35
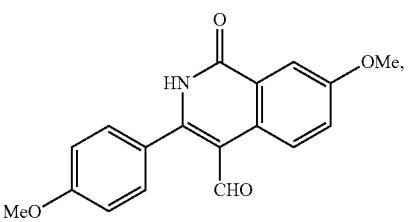
25
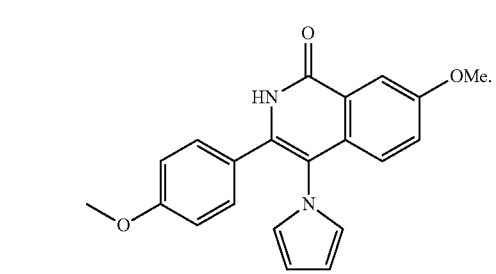
39
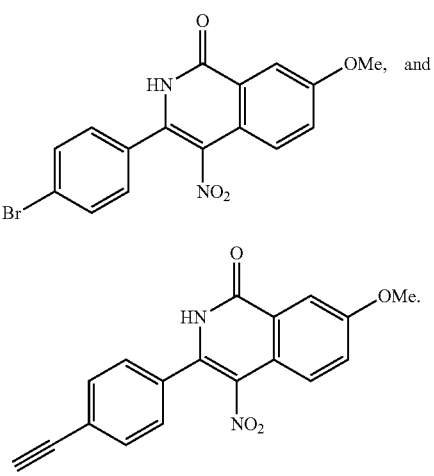
34
36
14. The method according to claim 1, wherein the compound of formula (I) is selected from the group consisting of:
15. The method according to claim 1, wherein the compound of formula (I) is selected from the group consisting of:

107
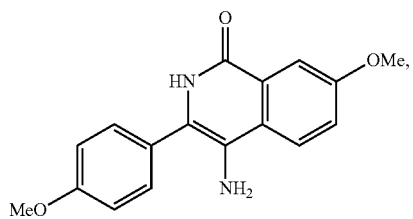
1
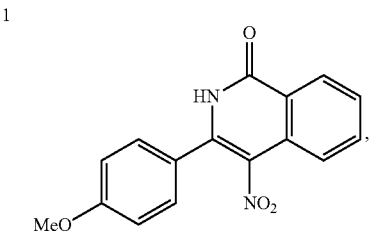
7
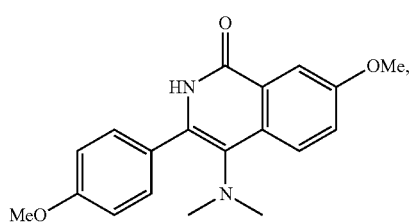
23
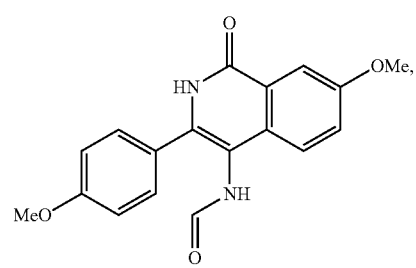
24
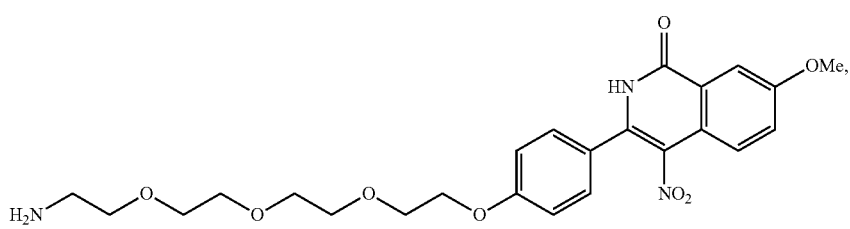
37
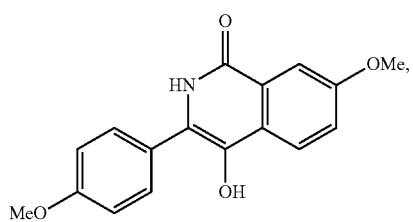
41
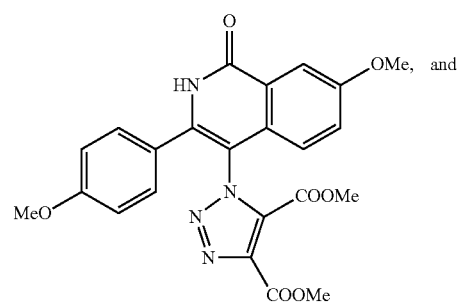
48
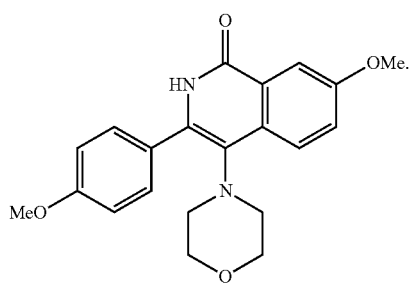
49
108
and 16. The method according to claim 1, wherein the compounds of formula (I) are selected from the group consisting of:

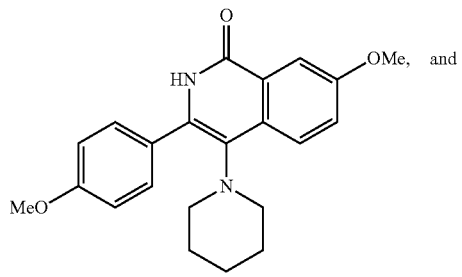

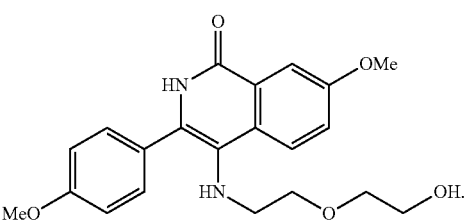

17. The method according to claim 1, wherein said compound possesses no anti-inflammatory properties.

18. The method according to claim 1, wherein said compound is administered by oral route, at a dose of from approximately 1 mg/kg to approximately 200 mg/kg.

19. The method according to claim 1, wherein said compound is administered by parenteral, intravenous, route at a dose of from approximately 0.1 mg/kg/d to approximately 100 mg/kg/d.

20. The method according to claim 1, wherein said compound is administered in combination with an antitumour drug selected from the group consisting of: abraxane, abarelix, aldesleukin, alemtuzumab, alitretinoin, allopurinol, altretamine, anastrozole, arsenic trioxide, asparaginase, azacitidine, bevacizumab, bexarotene, bicalutamide, bleomycin, bortezomib, intravenous busulphan, oral busulphan, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, 5-fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, taxol, taxotere, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

21. A pharmaceutical composition comprising as active ingredient a compound of formula I, as defined in claim 1, in combination with a pharmaceutically acceptable vehicle.

22. The pharmaceutical composition according to claim 21, comprising
a compound of formula I, wherein:
when n=0, then the bond between carbon 1 and the X group is single and X is $OCH_2$, or
when n=1, then the bond between carbon 1 and the X group is double, X=O or S, and R2 represents a phenyl substituted in position 4 by OH, $OCH_2$, O-benzyl, Br, a $C_2$-$C_4$ alkynyl group substituted or not, a tert-butyl, a hydroxy-2-propyl or an isopropyl; and
an antitumour drug selected from the group consisting of: abraxane, abarelix, aldesleukin, alemtuzumab, alitretinoin, allopurinol, altretamine, anastrozole, arsenic trioxide, asparaginase, azacitidine, bevacizumab, bexarotene, bicalutamide, bleomycin, bortezomib, intravenous busulphan, oral busulphan, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, 5-fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, taxol, taxotere, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

23. The pharmaceutical composition according to claim 21, comprising, in combination with a pharmaceutically acceptable vehicle, as an active ingredient, a compound selected from the group consisting of:

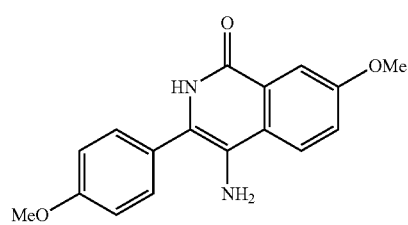

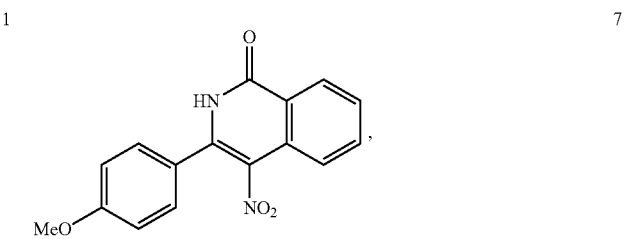

-continued
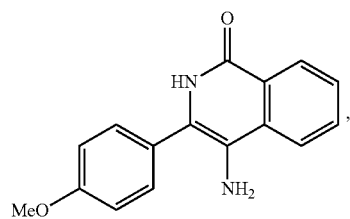
8
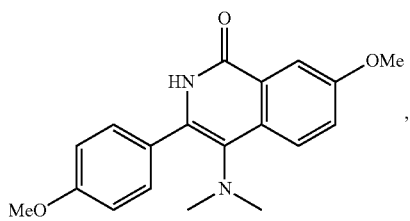
23
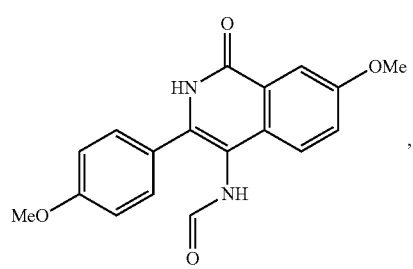
,
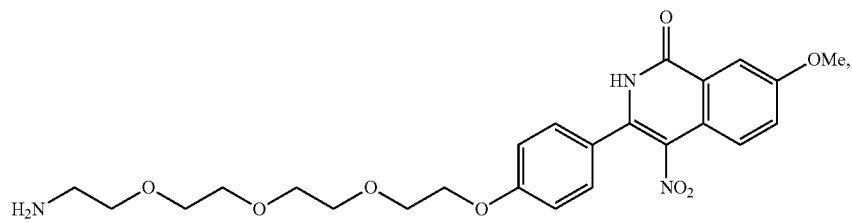
37
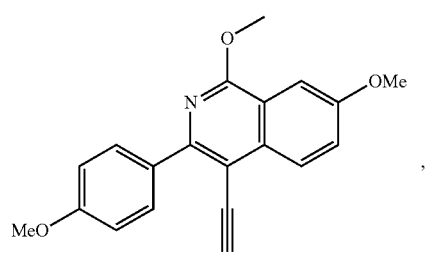
38
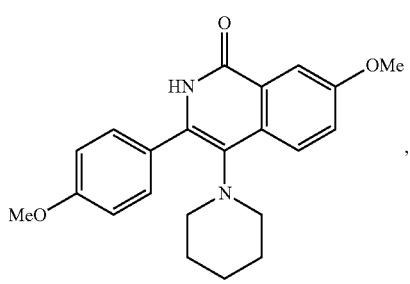
40
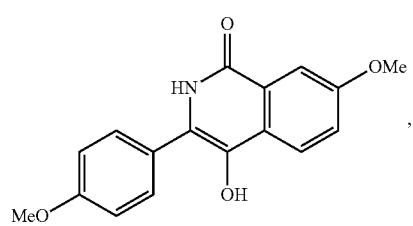
41
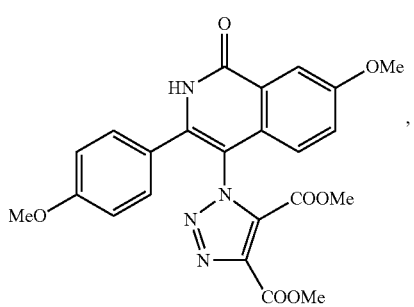
48
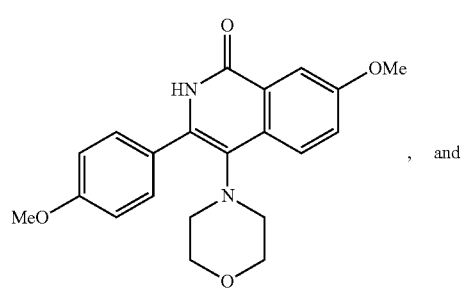
49 , and
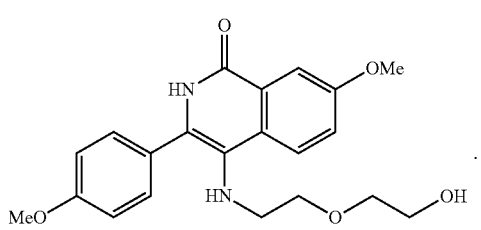
50 .

24. The pharmaceutical composition according to claim 21, comprising, in combination with a pharmaceutically acceptable vehicle, as an active ingredient, a compound selected from the group consisting of:

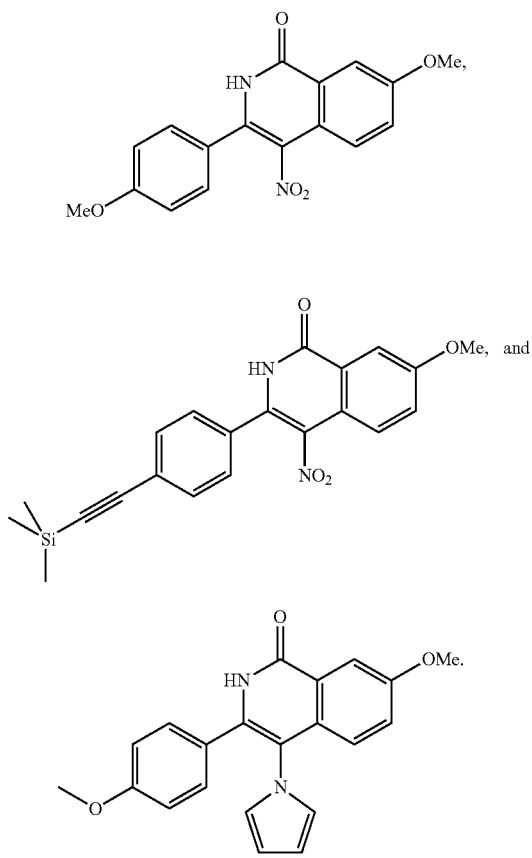

25. The pharmaceutical composition according to claim 21, comprising, in combination with a pharmaceutically acceptable vehicle, as an active ingredient, a compound selected from the group consisting of:

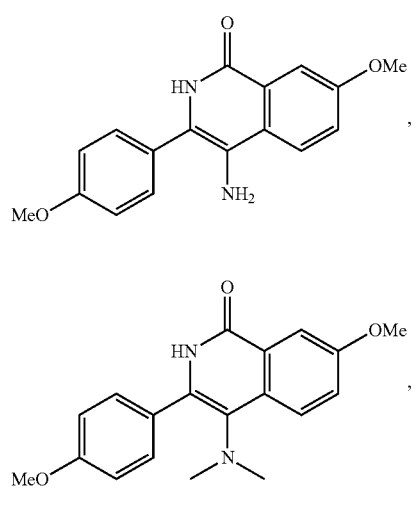

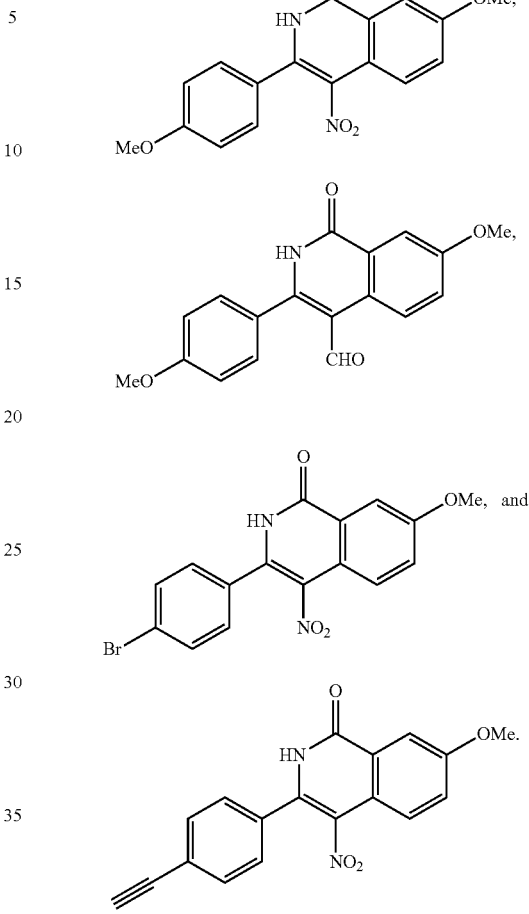

26. The pharmaceutical composition according to claim 21, comprising, in combination with a pharmaceutically acceptable vehicle, as an active ingredient, a compound selected from the group consisting of:

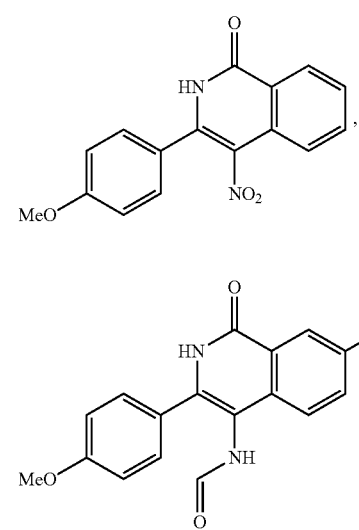

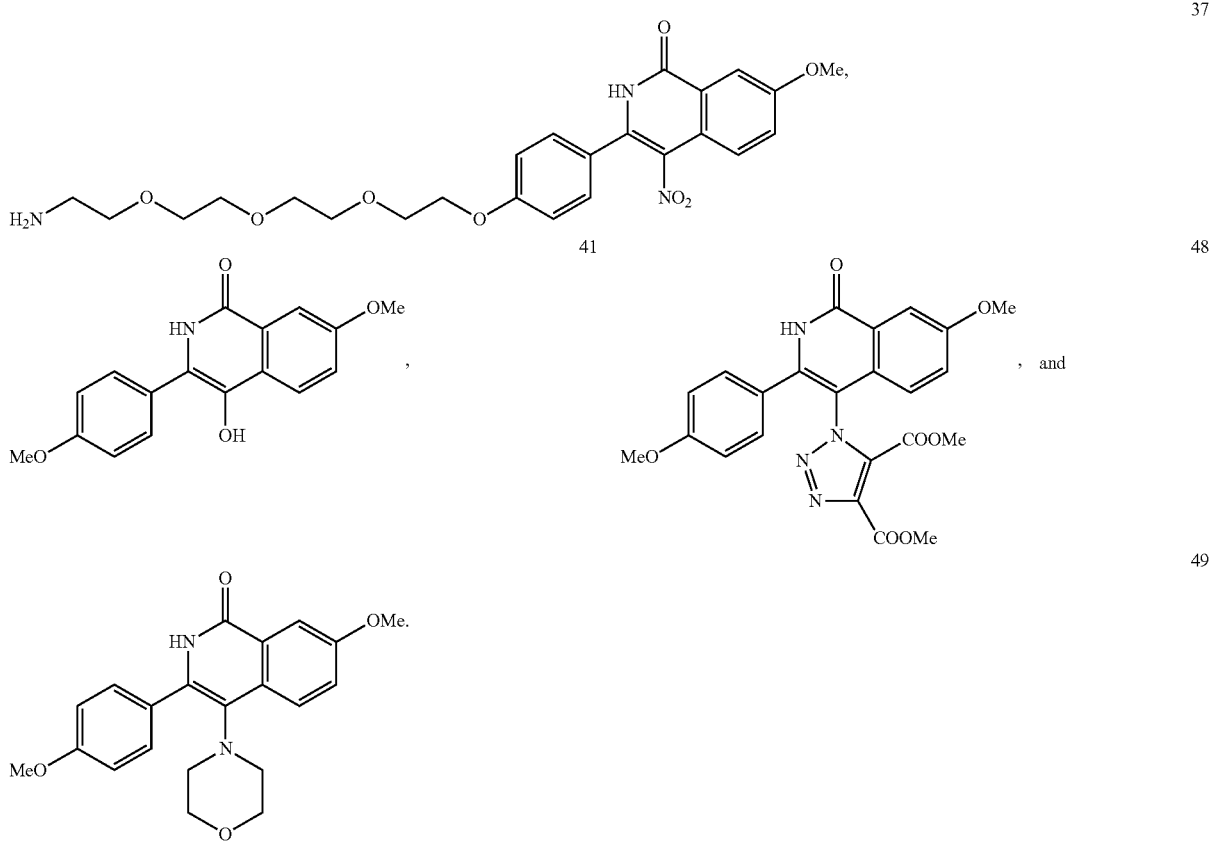

27. The pharmaceutical composition according to claim 21, comprising, in combination with a pharmaceutically acceptable vehicle, as an active ingredient, a compound selected from the group consisting of:

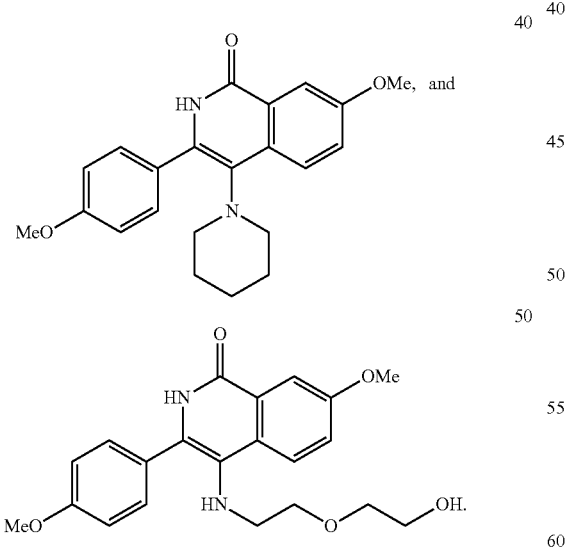

28. The pharmaceutical composition according to claim 21, administrable by oral route at a dose of from approximately 1 mg/kg to approximately 200 mg/kg.

29. The pharmaceutical composition according to claim 21, administrable by intravenous route at a dose of from approximately 0.1 mg/kg/d to approximately 100 mg/kg/d.

30. A compound of formula (I):

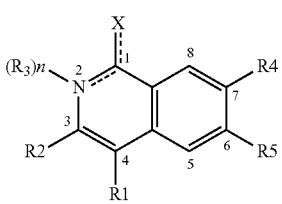

wherein:

1) the bond between carbon 1 and the X group is single or double, the bond between nitrogen 2 and carbon 1 can be single or double, it being understood that:
   a) when the bond between X and said carbon 1 is double, then the bond between nitrogen 2 and carbon 1 is single, and,
   b) when the bond between X and said carbon 1 is single, then the bond between nitrogen 2 and carbon 1 is double and formula I corresponds to an aromatic system of formula I-A:

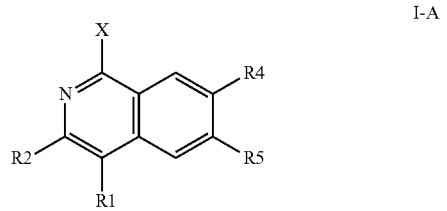

2) n represents 0 or 1,
3) X represents:
   a) when n=1: X represents O, or S,
   b) when n=0: X represents $OPO_3H_2$, OPO—(O—($C_1$-$C_2$)alkyl)$_2$, the alkyl being optionally substituted by one or more fluorines, O—($C_1$-$C_6$)alkyl, the alkyl being optionally substituted by one or more fluorines, NH—($C_3$-$C_6$) cycloalkyl, or S($C_3$-$C_6$)cycloalkyl,
4) R1 represents:
   $OPO_3H_2$, OPO—(O—($C_1$-$C_2$)alkyl)$_2$, the alkyl being optionally substituted by one or more fluorines,
   $CF_3$, $CH_2OR'$, R' representing H or ($C_1$-$C_6$) alkyl, the alkyl being optionally substituted by one or more fluorines, CHO,
   $CONR_cR_d$, $R_c$ and $R_d$ representing independently of each other: H, a $C_1$-$C_6$ alkyl, and $NR_cR_d$ represents an amino acid bound by its amine function, a $C_3$-$C_6$ cycloalkyl, or R, and $R_d$ represent together a $C_2$-$C_6$ alkyl,
   $NO_2$, $N_3$, ≡, C(=N)$NH_2$, $SO_3H$, $SO_2NH_2$, $SO_2NHCH_3$, $NHSO_2CH_3$, $CH_2SO_2NR_cR_d$, $CH_2NHSO_2Rc$, $SO_2$—$NRaRb$, $SO_2$-imidazole, $NR_aR_b$, where:
   $R_a$ and $R_b$ represent independently of each other: H, CHO, a $C_1$-$C_6$ alkyl, a $C_3$-$C_6$ cycloalkyl, or
   Ra is H, a $C_1$-$C_6$ alkyl, a $C_3$-$C_6$ cycloalkyl, and Rb=$COR_f$, $COOR_f$ or $CONR_fR_f$, $R_f$ and $R_f$ representing H, a $C_1$-$C_6$ alkyl, a $C_3$-$C_6$ cycloalkyl or an amino acid chain, or
   $R_a$ and $R_b$ represent together a $C_2$-$C_6$ alkyl, or $R_a$ and $R_b$ can form a $C_5$ to $C_7$ ring,
   a heteroaryl, substituted or not,
5) R2 represents:
   a phenyl substituted by one to three substituents chosen from:
   a halogen, an OH, NHRa,
   ORe, Re representing a benzyl, a methylene triazole, substituted or not,
   $OPO_3H_2$, OPO—(O—($C_1$-$C_2$)alkyl)$_2$, the alkyl being optionally substituted by one or more fluorines, an $NH_2$,
   an NH—CORc group in which Rc represents H, a $C_1$-$C_6$ alkyl, a $C_3$-$C_6$ cycloalkyl or an amino acid chain (such as CH($CH_2OH$)$NH_2$ for serine),
   an O—($C_1$-$C_6$)alkyl, the alkyl being optionally substituted by one or more fluorines,
   an O—COR1 where R1 represents O—($C_1$-$C_6$)alkyl, or NRiRii, Ri and Rii being able to be $C_1$-$C_6$ alkyl,
   a $C_2$-$C_4$ alkyl group, the alkyl group being optionally substituted by one or more fluorines,
   a $C_2$-$C_4$ alkenyl group, substituted or not,
   a $C_2$-$C_4$ alkynyl group, substituted or not,
   a heteroaryl, substituted or not,
   a cyclohexyl, a piperazine, a morpholine, a thiomorpholine, a piperidine,
   a 4-($NH_2$—($CH_2$—$CH_2O$)p)Ph group in which p is an integer from 1 to 6,
6) R3 represents:
   H, ($C_1$-$C_6$)alkyl, the alkyl being optionally substituted by one or more fluorines, ($C_3$-$C_6$)cycloalkyl, O—($C_1$-$C_6$)alkyl, a propargyl group, $CH_2CN$,
7) R4 and R5 represent independently of each other:
   H, OH, $OPO_3H_2$, OPO—(O—($C_1$-$C_2$)alkyl)$_2$, the alkyl being optionally substituted by one or more fluorines, an O—($C_1$-$C_6$)alkyl, the alkyl being optionally substituted by one or more fluorines, a $C_1$-$C_6$ alkyl, the alkyl being optionally substituted by one or more fluorines, a $C_3$-$C_6$ cycloalkyl, a halogen, or R4 and R5 represent together a ($C_1$-$C_2$) alkenyl dioxy optionally substituted by one or more fluorines,
with the exclusion of the following compounds:
when X=O, R3=H, and the bond between carbon 1 and the X group is double:
   a) R1=$NH_2$, R2=4-methoxy-phenyl, R4=$OCH_3$ and R5=H,
   c) R1=$NO_2$, R2=4-methoxy-phenyl, R4=$OCH_3$ and R5=H,
   d) R1=$NO_2$, R2=4-methoxy-phenyl, R4=H and R5=H,
   e) R1=$NH_2$, R2=4-methoxy-phenyl, R4=H and R5=H,
   h) R1=$NH_2$, R2=4-OH-phenyl, substituted or not, R4=H, OH, an O—($C_2$-$C_6$)alkyl, a $C_2$-$C_6$ alkyl, a $C_3$-$C_6$ cycloalkyl, and R5=H, OH, an O—($C_2$-$C_6$) alkyl, a $C_2$-$C_6$ alkyl, a $C_3$-$C_6$ cycloalkyl,
   i) the compounds in which one of R4 and R5 represents a halogen.

31. The compound according to claim 30, wherein:
when n=0, the bond between carbon 1 and the X group is single, X is $OCH_3$, and R1 is $NO_2$, or
when n=1, the bond between carbon 1 and the X group is double, X=O or S and R2 represents a phenyl substituted in position 4 by a group chosen from OH, $OCH_2$, O-benzyl, Br, a $C_2$-$C_4$ alkynyl group, substituted or not.

32. The compound according to claim 30, selected from the group consisting of:

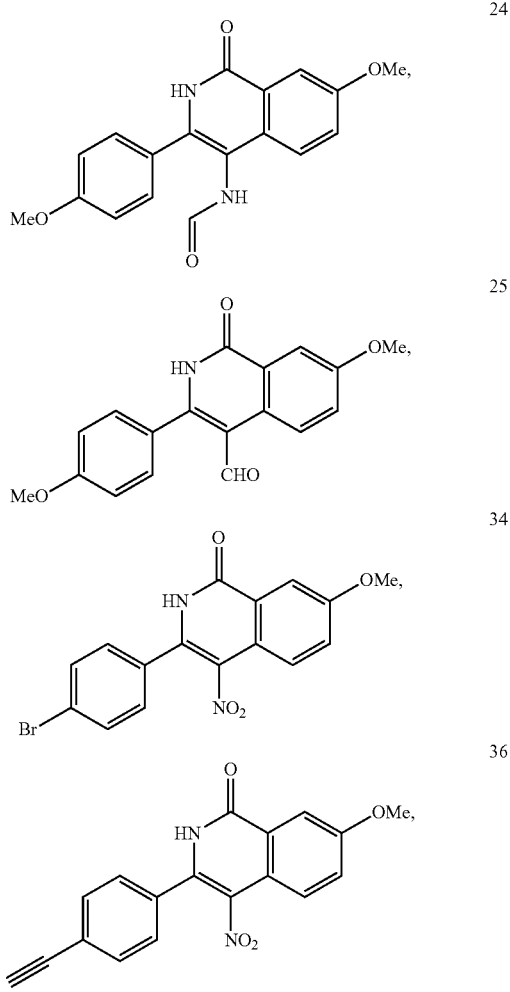

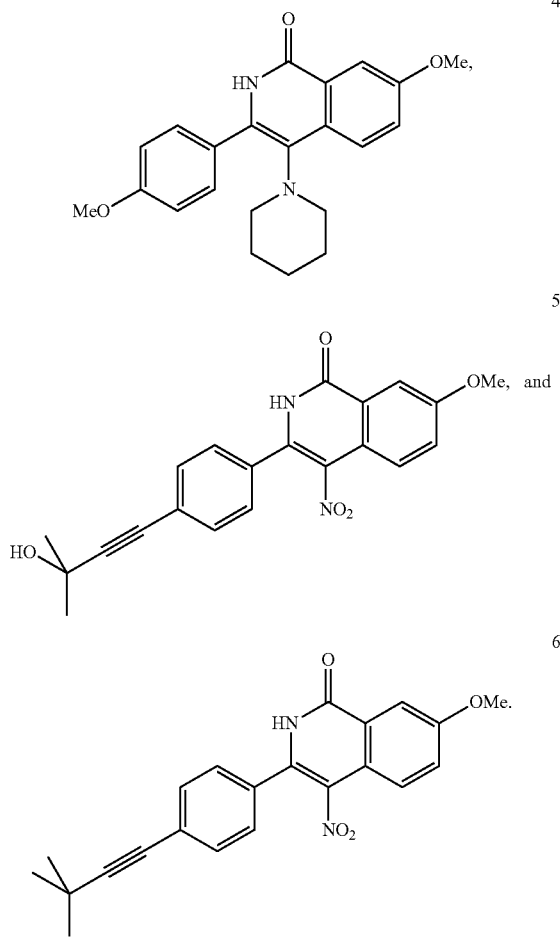

33. A product, comprising a first pharmaceutical preparation of formula (I), according to claim 1, and a second pharmaceutical preparation comprising at least one antitumor drug, as combined preparation for a simultaneous, separate or sequential use in the treatment of mammals suffering from benign or malignant tumours.

34. The product according to claim 33, wherein said antitumor drug is selected from the group consisting of: abraxane, abarelix, aldesleukin, alemtuzumab, alitretinoin, allopurinol, altretamine, anastrozole, arsenic trioxide, asparaginase, azacitidine, bevacizumab, bexarotene, bicalutamide, bleomycin, bortezomib, intravenous busulphan, oral busulphan, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, 5-fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, taxol, taxotere, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

\* \* \* \* \*